(12) United States Patent
Smilansky

(10) Patent No.: US 8,442,773 B2
(45) Date of Patent: May 14, 2013

(54) PROTEIN SYNTHESIS MONITORING (PSM)

(75) Inventor: Zeev Smilansky, D.N. Emek Soreq (IL)

(73) Assignee: Anima Cell Metrology, Bernardsville, NJ (US)

( * ) Notice: Subject to any disclaimer, the term of this patent is extended or adjusted under 35 U.S.C. 154(b) by 0 days.

(21) Appl. No.: 12/872,736

(22) Filed: Aug. 31, 2010

(65) Prior Publication Data

US 2010/0317121 A1  Dec. 16, 2010

Related U.S. Application Data

(63) Continuation-in-part of application No. 10/537,071, filed as application No. PCT/IL03/01011 on Nov. 27, 2003, now Pat. No. 7,807,349.

(60) Provisional application No. 60/429,532, filed on Nov. 29, 2002.

(51) Int. Cl.
*C12Q 1/68* (2006.01)
*G01N 33/48* (2006.01)
*G01N 33/53* (2006.01)

(52) U.S. Cl.
USPC .............................. 702/19; 702/20; 435/6.1

(58) Field of Classification Search ........................ None
See application file for complete search history.

(56) References Cited

U.S. PATENT DOCUMENTS

| 5,626,058 | A | 5/1997 | Karpowich et al. ............... 74/489 |
| 5,777,079 | A | 7/1998 | Tsien et al. ........................ 530/350 |
| 5,922,858 | A | 7/1999 | Rothschild et al. ............ 536/24.1 |
| 6,210,941 | B1 | 4/2001 | Rothschild et al. ............. 435/183 |
| 2004/0023256 | A1* | 2/2004 | Puglisi et al. ....................... 435/6 |
| 2004/0023874 | A1* | 2/2004 | Burgess et al. ................... 514/12 |

FOREIGN PATENT DOCUMENTS

| WO | WO 01/16375 A2 | 3/2001 |
| WO | WO 03/064604 A2 | 8/2003 |
| WO | WO 2004/050825 A2 | 6/2004 |

OTHER PUBLICATIONS

Akerman et al., "Nanocrystal targeting in vivo," Proc Natl Acad Sci USA, 99(20):12617-12621 (2002).
Bain et al., "Site-Specific Incorporation of Nonnatural Residues during In Vitro Protein Biosynthesis with Semisynthetic Aminoacyl-tRNAs," Biochemistry 30(22):5411-5421 (1991).
Bakin et al., "Spatial Organization of Template Polynucleotides on the Ribosome Determined by Fluorescence Methods," J. Mol. Biol. 221(2):441-453 (1991).
Bastiaens et al., "Fluorescence lifetime imaging microscopy: spatial resolution of biochemical processes in the cell," Trends in Cell Biology 9(2): 48-52 (1999).

(Continued)

*Primary Examiner* — Michael Borin
(74) *Attorney, Agent, or Firm* — Winston & Strawn LLP

(57) ABSTRACT

A method and a device are disclosed for monitoring the synthesis of proteins by the ribosome, wherein the ribosome is bound to a first label, for example a donor fluorophore, and a tRNA and/or amino acid are is bound to a second label, for example an acceptor fluorophore, wherein the first and second labels together form a FRET pair. As the ribosome mechanism processes the mRNA and tRNA molecules and synthesizes a polypeptide chain, a light source illuminates the ribosome, exciting the donor fluorophores and thereby the acceptor fluorophores whenever these are in sufficient proximity to a donor. The resulting signals are detected and used as a key for database searching and identification of the protein being synthesized.

16 Claims, 16 Drawing Sheets

OTHER PUBLICATIONS

Baubet et al., "Chimeric green fluorescent protein-aequorin as bioluminescent Ca2+ reporters at the single-cell level," Proc Natl Acad Sci USA 97(13):7260-7265 (2000).

Braslavsky et al., "Sequence information can be obtained from single DNA molecules," Proc Natl Acad Sci USA 100(7):3960-3964 (2003).

Campagnola et al., "Second-harmonic imaging microscopy for visualizing biomolecular arrays in cells, tissues and organisms," Nature Biotechnology 21(11):1356-1360 (2003).

Cload et al., "Development of improved tRNAs for in vitro biosynthesis of proteins containing unnatural amino acids," Chemistry & Biology 3(12):1033-1038 (1996).

Cornish et al., "Site-specific incorporation of biophysical probes into proteins," Proc. Natl. Acad. Sci. USA 91(8):2910-2914 (1994).

De Angelis, "Why FRET over genomics?," Physiol. Genomics 1(2):93-99 (1999).

Deniz et al., "Single-molecule protein folding: Diffusion fluorescence resonance energy transfer studies of the denaturation of chymotrypsin inhibitor 2," Proc Natl Acad Sci USA 97(10):5179-5184 (2000).

Denk et al., "Two-Photon Laser Scanning Fluorescence Microscopy," Science 248(4951):73-76 (1990).

Dirks et al., "Methods for visualizing RNA processing and transport pathways in living cells," Histochemistry and Cell Biology 115(1):3-11 (2001).

Dubertret et al., "In Vivo Imaging of Quantum Dots Encapsulated in Phospholipid Micelles," Science 298(5599):1759-1762 (2002).

Emptage, "Fluorescent imaging in living systems," Current Opinion in Pharmacology 1(5):521-525 (2001).

Ha et al., "Probing the interaction between two single molecules: Fluorescence resonance energy transfer between a single donor and a single acceptor," Proc. Natl. Acad. Sci. USA 93(13):6264-6268 (1996).

Ha, "Single-Molecule Fluorescence Resonance Energy Transfer," Methods 25(1):78-86 (2001).

Ha, Single Molecules, 2(4):283-284 (Dec. 5, 2001).

Harms et al., "Single-Molecule Imaging of L-Type $CA^{2+}$ Channels in Live Cells," Biophysical Journal 81(5):2639-2646 (2001).

Heinze et al., "Simultaneous two-photon excitation of distinct labels for dual-color fluorescence crosscorrelation analysis," Proc. Natl. Acad. Sci. USA 97(19):10377-10382 (2000).

Ilegems et al., "Monitoring mis-acylated tRNA suppression efficiency in mammalian cells via EGFP fluorescence recovery," Nucleic Acids Research 30(23):3128 (2002).

Jaiswal et al., "Long-term multiple color imaging of live cells using quantum dot bioconjugates," Nat Biotechnol 21(1):47-51 (2003).

Jia et al., "Nonexponential kinetics of a single $tRNA^{Phe}$ molecule under physiological conditions," Proc. Natl. Acad. Sci. USA 94(15):7932-7936 (1997).

Jovin, "Quantum dots finally come of age," Nat Biotechnol. 21(1):32-33 (2003).

Kenworthy, "Imaging Protein-Protein Interactions Using Fluorescence Resonance Energy Transfer Microscopy," Methods 24(3):289-296 (2001).

Klostermeier et al., "RNA Conformation and Folding Studied with Fluorescence Resonance Energy Transfer," Methods 23(3):240-254 (2001).

Kukhanova et al., "Peptidyl-tRNA with a Fluorescent Label: Ribosome Substrates in Peptide Bond Formation," Molecular Biology Reports 1:397-400 (1974).

Mascarenhas et al., "Specific polar localization of ribosomes in *Bacillus subtilis* depends on active transcription," EMBO Reports 2(8):685-689 (2001).

Medintz et al., "Self-assembled nanoscale biosensors based on quantum dot FRET donors," Nature Materials 2(9):630-638 (2003).

Meissner et al., "Development of an inducible pol III transcription system essentially requiring a mutated form of the TATA-binding protein," Nucleic Acids Research 29(8):1672-1682 (2001).

Miyawaki et al., "Lighting up cells: labelling proteins with fluorophores," Nat Cell Biol. Suppl:S1-S7 (2003).

Odom et al., "Distances Between 3' Ends of Ribosomal Ribonucleic Acids Reassembled into *Escherichia coli* Ribosomes," Biochemistry 19(26):5947-5954 (1980).

Odom et al., "Relaxation Time, Interthiol Distance, and Mechanism of Action of Ribosomal Protein S1," Archives of Biochemistry and Biophysics 230(1):178-193 (1984).

Odom et al., "Fluorescence Labeling and Isolation of Labeled RNA and Ribosomal Proteins," Methods in Enzymology 164:174-187 (1988).

Odom et al., "Movement of tRNA but Not the Nascent Peptide during Peptide Bond Formation on Ribosomes," Biochemistry 29:10734-10744 (1990).

Plumbridge et al., "Characterization of a new, fully active fluorescent derivative of *E. coli* $tRNA^{Phe}$," Nucleic Acids Research 8(4):827-843 (1980).

Paulsen et al., "tRNA Topography during Translocation: Steady-State and Kinetic Fluorescence Energy-Transfer Studies," Biochemistry 25:2749-2756 (1986).

Sako et al., "Single-molecule visualization in cell biology," Nat Rev Mol Cell Biol. Suppl:SS1-SS5 (2003).

Sako et al., "Total Internal Reflection Fluorescence Microscopy for Single-molecule Imaging in Living Cells," Cell Structure and Function 27(5):357-365 (2002).

Schlege et al., "The turnover of tRNAs microinjected into animal cells," Nucleic Acids Research 5(10):3715-3729 (1978).

Schwille et al., "Analyzing single protein molecules using optical methods," Current Opinion in Biotechnology 12:382-386 (2001).

Sei-lida et al., "Real-time monitoring of in vitro transcriptional RNA synthesis using fluorescence resonance energy transfer," Nucleic Acids Research 28(12):e59 (2000).

Selvin, "The renaissance of fluorescence resonance energy transfer," Nature Structural Biology 7(9):730-734 (2000).

Shimizu et al., "Cell-free translation reconstituted with purified components," Nature Biotechnology 19(8): 751-755 (2001).

Smilansky, "Automatic registration for images of two-dimensional protein gels," Electrophoresis 22(9): 1616-1626 (2001).

Sytnik et al., "Peptidyl Transferase Center Activity Observed in Single Ribosomes," Journal of Molecular Biology 285(1):49-54 (1999).

Terpe, "Overview of tag protein fusions: from molecular and biochemical fundamentals to commercial systems," Appl Microbiol Biotechnol 60:523-533 (2003).

Toomre et al., "Lighting up the cell surface with evanescent wave microscopy," Trends in Cell Biology 11(7):298-303 (2001).

Vanzi et al., "Protein synthesis by single ribosomes," RNA 9(10):1174-1179 (2003).

Weiss, "Fluorescence Spectroscopy of Single Biomolecules," Science 283(5408):1676-1683 (1999).

Zhuang et al., "Correlating Structural Dynamics and Function in Single Ribozyme Molecules," Science 296:1473-1476 (2002).

Zipfel et al., "Nonlinear magic: multiphoton microscopy in the biosciences," Nature Biotechnology 21(11):1369-1377 (2003).

International Search Report, Application No. PCT/IL03/01011, Oct. 19, 2004.

U.S. Appl. No. 60/351,919, filed Jan. 25, 2002.

Ha et al., (1999) Ligand-induced conformational changes observed in single RNA molecules. PNAS USA 96(16):9077-82.

Singh KK. et al., (1999) Rapid kinetic characterization of hammerhead ribozymes by real-time monitoring of fluorescence resonance energy transfer (FRET). RNA 5(10):1348-56.

* cited by examiner

Fig. 14a
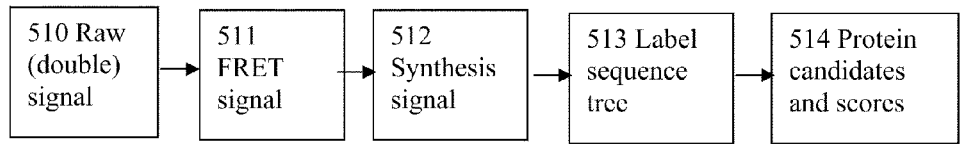
Fig. 14b
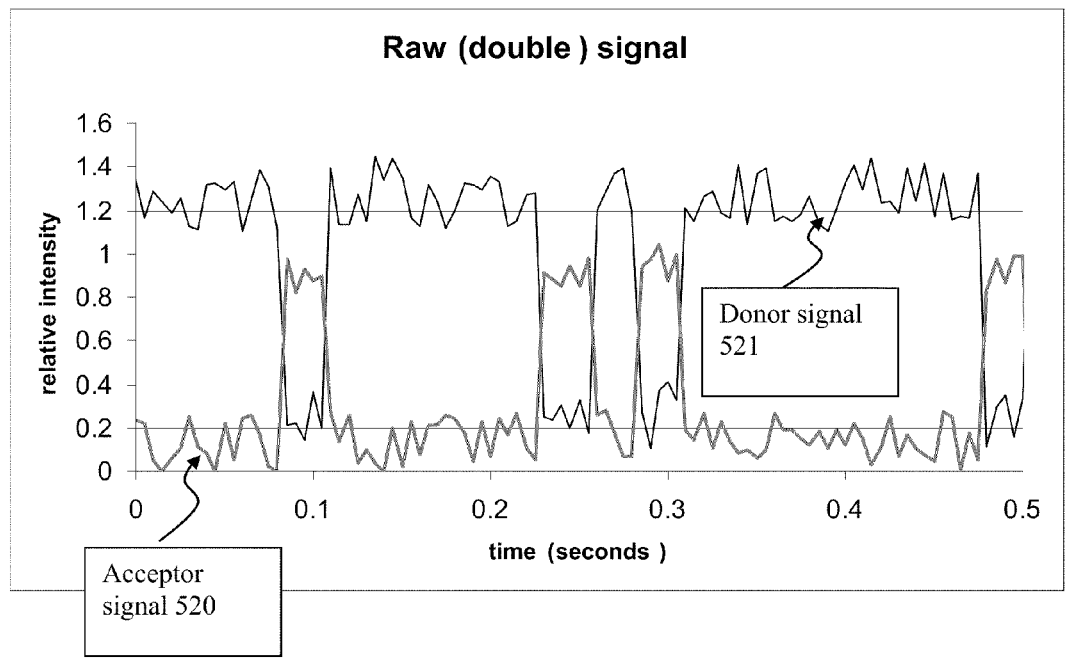
Fig. 14c
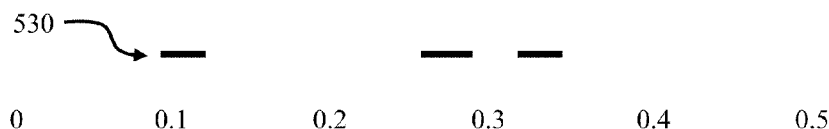
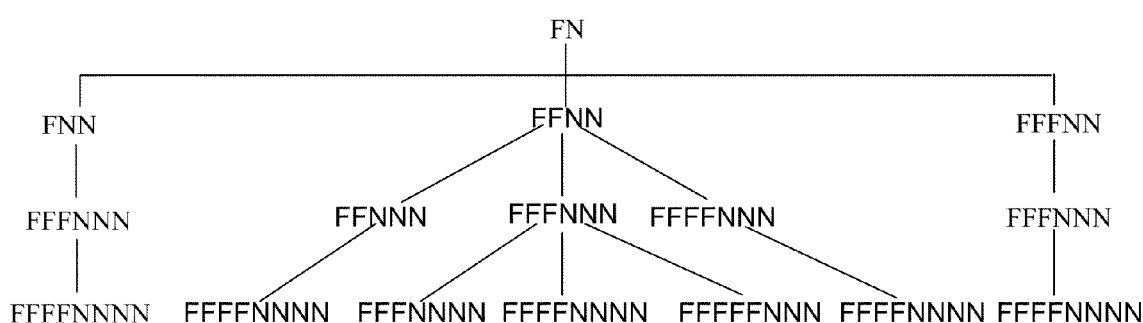
Fig. 14d

PROTEIN SYNTHESIS MONITORING (PSM)

CROSS REFERENCE TO RELATED APPLICATIONS

This application is a continuation-in-part application of U.S. application Ser. No. 10/537,071 filed Jan. 9, 2006, now U.S. Pat. No. 7,807,349 which is the U.S. national phase application of PCT application No. PCT/IL2003/001011, International filing date Nov. 27, 2003, which claims the benefit of U.S. application No. 60/429,532 filed Nov. 29, 2002.

FIELD OF THE INVENTION

The present invention relates to the monitoring of protein synthesis by ribosomes, and in particular to such monitoring being performed in real time.

BACKGROUND OF THE INVENTION

The study of proteins is a key endeavor of current biological research, as well as a focus of pharmaceutical research and development. The information revealed by sequenced genomes increases the pace and activity of protein research, for example for the development of a cell-based assay, analysis of a pathway, study of a single receptor, or the application of proteomics. Current technologies fail at several key points: they can miss entire protein families; fail to identify protein pathways; focus on a single protein at a time; and they are expensive, difficult and slow. Importantly, no current technology provides information on protein dynamics. In fact, results of current large-scale and high-throughput protein analysis are often delayed by days or weeks following an experiment, and are usually restricted to the form of a catalogue, tabulating those proteins of a database that have been putatively identified from the analyzed sample.

Genomics, Proteomics and the Barriers of Biological Knowledge

Proteomics is an emerging technology that attempts to study proteins on a large scale in high-throughput. It is not by chance that the term resembles "Genomics". In the wake of successful technologies such as whole genome sequencing, DNA chips and SNP cataloging, a search started for similar paradigms in the realm of proteins. This search is worthwhile since proteins are the main vehicles of life processes: they are the biochemical enzymes, form the signal pathways, control the cellular processes, underpin the cell scaffolding, transport molecules and so on. They are also potentially more valuable than DNA in terms of human benefit, due to their importance in human disease: most known drugs are either proteins themselves, or else operate by binding to a protein target. Unfortunately, proteins are also so much more complex and difficult to study than DNA. They are more complex for a number of reasons. For example, there are many more proteins than there are genes; protein expression is complex and has a high dynamic range—from single copies to millions per cell; the proteome of one cell type may be very different than that of another, even though their DNA is identical; and proteins may undergo dramatic changes in their structure—through cleavage, modification, and interaction. Proteins are more difficult to study than DNA, since protein extraction, separation and identification are difficult; there is no amplification technique that parallels PCR; three-dimensional protein structure is hard to obtain and use; protein expression has high dynamic range; protein modifications, cleavages and interactions are to a large extent unknown; and, finally, both as cause and effect, protein databases are thin and sparsely populated, encompassing a small fraction of all theoretical proteins, especially in higher organisms, such as *Homo sapiens*.

In one aspect, though, Proteomics and Genomics are similar: both raised high hopes of creating a paradigm shift, a breakthrough that will yield a new understanding of cellular processes and human disease, and pave the way to a bounty of new drugs and therapeutics. Unfortunately, first for genomics and then for proteomics, it became abundantly clear that though genomic and proteomic data is extremely valuable, it is far from sufficient for achieving the breakthrough that was hoped for (Miklos, G. L. and Maleszka, R., *Protein functions and biological contexts*. Electrophoresis 22:169-178, 2001). So many pieces of the puzzle are still missing that the clear and complete view of cellular machinery remains hidden. One important piece of this puzzle is protein synthesis data—which proteins are produced at which times, under which conditions, and in which amounts. The ability to study and monitor this type of data would be a major breakthrough for all life science related research.

Proteomics Practice Today

Mainstream proteomic analysis today includes the processes of protein purification from culture, separation with two-dimensional gel or other chromatographic techniques, mass-spectrometry, and analysis of the resulting spectra for protein identification and characterization.

The extraction of proteins from bacterial or cell culture invariably involves lysis (and therefore death) of the cells. The procedure involves several stages and usually takes hours (Branca M A, Sannes L J. *Proteomics: A Key Enabling Tool for Genomics*? Cambridge Healthtech Institute's Genomic Reports. April 1999; Humphery-Smith I., Cordwell S. J., Blackstock W. P., *Proteome research: complementarity and limitations with respect to the RNA and DNA worlds*, Electrophoresis 18 (1997) 1217-1242). Protein separation with two-dimensional gels requires at least 24 hours and an expert human operator; their analysis is often much more difficult, even with modern software (Smilansky, Z. *Automatic registration for images of two-dimensional protein gels*, Electrophoresis 2001, 22, 1616-1626). Even worse, two-dimensional gel technology is not applicable to very acidic or very basic proteins, to many membranal proteins, and most importantly, to proteins that are expressed in low amounts.

It is usually taken for granted that proteins that are expressed at less than 1000-10,000 copies per cell cannot be visualized in two-dimensional gels (Gygi, S. P., Rist, B., Gerber, S. A., Turecek, F., Gelb, M. H., Aebersold, R., *Quantitative analysis of complex protein mixtures using isotope-coded affinity tags*. Nat. Biotechnol. 1999, 17 (10): 994-9). Almost no protein kinases, phosphatases, transcription factors, GPCRs, ion channels, or nuclear hormone receptors are found in standard human proteomic analyses, even though more than 5000 of these proteins are encoded by the human genome (Miklos, G. L., Maleszka, R. *Protein functions and biological contexts*, Electrophoresis 22:169-178, 2001). Thus, the proteins that can be analyzed by this method are only the most common ones.

Besides separating the sample, two-dimensional gel technology can measure three important protein parameters: mass, pI, and quantity. However, all three are hopelessly inaccurate. As for protein quantity, the most that may be obtained from gel technology is relative quantitation, and even that at accuracies worse than 50% error—so that only proteins with very strong up- or down-regulation can be identified. Moreover, quantitation at best means quantity of protein in the extracted, processed sample, such as in a gel spot or in a chromatographic fraction; estimation of protein copies in a cell at any given time is not even attempted today.

Following protein separation, MS analysis may be performed, either with a MALDI-TOF or with an LC-MS-MS machine (Humphery-Smith I., Cordwell S. J., Blackstock W. P., *Proteome research: complementarity and limitations with respect to the RNA and DNA worlds*, Electrophoresis 18 (1997) 1217-1242; Yates J. R., *Database searching using mass spectrometry data*. Electrophoresis 1998, 19 (6): 893-900). The main stages are spot picking from the gel followed by destaining, or alternatively chromatographic prefractionation, followed by protein digestion with a protease (almost invariably trypsin), mass-spectrometric analysis, and finally database searching, which is performed, surprisingly, only as a semi-automatic procedure with expert supervision and decision making—as in the stages of peak extraction and candidate selection.

All in all, the standard technique for identifying proteins in a cell culture takes from weeks to months, is suitable for only a small part of the proteome, does a bad job of quantitating protein amounts, and provides no clue as to proteome dynamics.

Additional and Emerging Proteomics Technologies

An important older method for protein analysis is Edman degradation, a chemical analysis method where the C-terminal amino acids of a polypeptide are cleaved and analyzed one by one. The procedure requires a full day and provides no quantitative or dynamic information.

The shortcomings of two-dimensional gel technology have led many researchers to look for alternatives. Two important developments of the last few years are the techniques of ICAT (Gygi, S. P., Rist, B., Gerber, S. A., Turecek, F., Gelb, M. H., Aebersold, R., *Quantitative analysis of complex protein mixtures using isotope-coded affinity tags*. Nat. Biotechnol. 1999, 17 (10): 994-9) and MudPIT (Washburn, M. P., Wolters, D., Yates J R 3rd. *Large-scale analysis of the yeast proteome by multidimensional protein identification technology*. Nat. Biotechnol. 2001 Mar. 19 (3): 242-7), which involve MS analysis of whole sample digestion products. The two methods allow better identification of rare proteins, and the first one even allows computation of differential expression. However, they are still difficult and expensive to carry out, require cell lysis, take days for complete analysis, and provide no dynamic information.

Protein chips are being developed in several labs (Jenkins, R. E. and Pennington, S. R. *Arrays for protein expression profiling: towards a viable alternative to two-dimensional gel electrophoresis?* Proteomics. 2001 Jan. 1 (1):13-29). They generally fall into one of three classes: surface chemistry chips, antibody chips, or protein chips for determining protein-protein interactions. All of these may aid protein analysis in some way, but none of them provides the data that the disclosed method provides.

Yeast-two-hybrid technique (Y2H) is a feat of bioengineering that helps discover protein-protein interactions (Legrain, P. and Selig, L., *Genome-wide protein interaction maps using two-hybrid systems*. FEBS Lett. 2000 Aug. 25; 480 (1):32-6). The method is indirect in that the interactions occur in yeast or in bacteria, rather than in the original cells being analyzed. It is known to generate a large number of false-positives and also cannot generate dynamic information. Thus, there are clearly a number of significant differences between the present invention and the disclosed method.

High Throughput Screening and Cell Based Assays

High throughput Screening (HTS) is the standard route for drug discovery in the pharmaceutical industry. Traditionally, HTS relies on a simple assay, such as receptor binding or enzyme activity. The assay itself measures a single parameter, e.g. receptor binding. This measurement is initially the only information available on the suitability of the candidate compound as a potential drug. The rest of the required information—ADME-TOX for example—is either presumed to be known or else its acquisition is delayed till later stages in the process (see also next section).

In contrast with simple assays, cell-based assays are newer to the pharmaceutical industry. They are usually used for lead optimization and predictive toxicology. To construct a cell-based assay, a measurable cell characteristic has to be developed: this can be a fluorescent-tagged protein, an antibody based marker, or some measurable phenotypic characteristic of the cell. Modern examples include cancer-specific dyes (http://www.zetiq.com/site/cama.html) and genetically engineered cell lines (Shen-Orr, S. S., Milo, R., Mangan, S., and Alon, U., *Network motifs in the transcriptional regulation network of Escherichia coli*. Nat Genet 2002, 31 (1): 64-8; http://www.cellomics.com/).

Cell based assays have many advantages over receptor binding assays. Cells offer better representations of a disease. By screening against disease pathways in whole cells, no prior assumptions are made about what makes a good target. However, cell based screening suffers from certain disadvantages. These disadvantages include the need to engineer a specific cell line with the required reporting capability, and the lack of information about the would-be protein target. In both assay types, standard and cell-based assays, high-throughput screening provides a minimal amount of information on a large number of compounds. This of course limits the scope of information obtainable, and the entire cascade of events following administration of the compound under analysis remains hidden from the researcher.

Improved solutions for the above problems are clearly required, for example for pharmaceutical research and development. Despite the huge increase in investment and the enormous contributions of genomics and related technologies, the main difference between the pharmaceutical pipeline today and a decade ago is in the number of targets, while the number of successful drugs entering the market has more or less stayed the same. More discouraging yet is the fact that while advances in high-throughput screening, chemical compound library design and bioinformatics have helped multiply the number of "hits" in HTS assays, the number of "leads" has not increased at all. Thus, the pharmaceutical pipeline today has an abundance of targets on the one side and an abundance of candidate compounds on the other, but attempts to combine this information has yielded little.

Though there is more than one reason for this failure, one important point is that though the numbers of targets and candidates is huge, the complexity of the cellular machinery, not to mention tissue and whole organism, is on a grander scale still. Thus, a better view of function and context of a protein target in the cell, as well as the complex effects, side effects, and after effects of a drug compound on the cell, are all clearly missing.

In today's paradigm of drug development, once a target is found and a compound that binds to it is identified, drug development starts to proceed toward towards regulatory approval and market acceptance. While the process is long and very expensive, it is narrow in the sense that relatively little is known about the target protein, its function, its isoforms and look-alikes, its roles in disease and in health. Even less is known about the drug candidate, how it affects proteins other than its specified target, how it affects other tissues, its immediate effects and its long term effects. Thus, information that may indicate that a compound cannot become a suitable drug candidate is revealed only at later stages and at a high cost—sometimes only after being distributed on the market. Among the medications which had to be recalled after market approval are the nighttime heartburn drug Propulsid (removed because of fatal heart rhythm abnormalities), diabetes drug Rezulin (removed after causing liver failure), and irritable-bowel-syndrome treatment Lotronex (removed for causing fatal constipation and colitis). All three were taken off the market in 2000.

SUMMARY OF THE INVENTION

The present invention provides a method and apparatus for monitoring protein synthesis in a protein synthesis system, which enables determining the identity of one or more proteins being synthesized at a given instant in a single ribosome. The method of the present invention is also referred to herein as "PSM" (protein synthesis monitoring). Protein synthesis is monitored by using a marker or a set of markers for protein synthesis in the system, which causes electromagnetic radiation to be emitted. The emitted electromagnetic radiation is then detected, captured and analyzed to determine the identity of the synthesized proteins. The present invention may optionally be performed qualitatively, but is preferably performed quantitatively. The marker preferably comprises a fluorescence resonance energy transfer (FRET) donor/acceptor pair or a set of one donor and several types of acceptors (each one with a different emission wavelength), or a set of several donor types and one acceptor, or several donors and acceptor types In a currently preferred embodiment, the present invention comprises a method of monitoring protein synthesis by a single ribosome. However, the invention may optionally be performed for hundreds of single ribosomes simultaneously.

In the present invention, the ribosome is engineered to carry a donor fluorophore, and tRNA and/or amino acids are engineered to carry one or more acceptor fluorophores; or alternately, the ribosome carries an acceptor fluorophore, and tRNA and/or amino acids carry one or more donor fluorophores. Donors and acceptors are selected so that a donor can transfer energy to the acceptor when the donor is excited and the acceptor is in close proximity to the donor. As the ribosome mechanism reads mRNA information, processes tRNA molecules and synthesizes a polypeptide chain, a light source illuminates the ribosome so as to excite the donor fluorophore attached thereto or attached to a closely located tRNA or amino acid, and thereby transfer energy to an acceptor fluorophore which is within sufficient proximity. The resulting signals are detected by appropriate optical apparatus and collected by a computerized analysis system as digital data. This digital data is used as a key for database searching and identification of the protein being synthesized.

According to a first aspect, the present invention provides a method for identifying one or more proteins synthesized in a protein synthesis system, the method comprising:

binding at least one first label to at least one ribosome or a fragment thereof in the protein synthesis system binding at least one second label to at least one tRNA or to at least one amino acid in the protein synthesis system; wherein one of the first label and the second label is a donor fluorophore, and the other is an acceptor fluorophore, and wherein the donor fluorophore and the acceptor fluorophore together form a fluorescence resonance energy transfer (FRET) pair;

detecting FRET signals emitted from a single ribosome when the first and second labels are in proximity;

compiling a key from the detected FRET signals; and interrogating a protein-specific database with said key;

thereby identifying the one or more proteins being synthesized in the system.

In a particular embodiment, the first label is a donor fluorophore and the second label is an acceptor fluorophore. In a particular embodiment, the first label is an acceptor fluorophore and the second label is a donor fluorophore. In a particular embodiment, the method comprises binding a donor fluorophore to a ribosome or a fragment thereof, and binding an acceptor fluorophore to a tRNA. In a particular embodiment, the method comprises binding a donor fluorophore to a ribosome or a fragment thereof, and binding an acceptor fluorophore to an amino acid. In a particular embodiment, the method comprises binding an acceptor fluorophore to a ribosome or a fragment thereof, and binding a donor fluorophore to a tRNA. In a particular embodiment, the method comprises binding an acceptor fluorophore to a ribosome or a fragment thereof, and binding a donor fluorophore to an amino acid. In a particular embodiment, the method comprises binding one donor fluorophore to a ribosome or a fragment thereof, and binding at least two different acceptor fluorophores to two different tRNAs.

In a particular embodiment, the binding to a ribosome comprises binding to a ribosomal protein selected from the group consisting of ribosomal protein L1, ribosomal protein L11, S1, ribosomal protein S21, and a combination thereof.

In a particular embodiment, the protein synthesis system comprises at least one cell. In a particular embodiment, the protein synthesis system comprises at least one of a cell-line or a cell culture. In a particular embodiment, the protein synthesis system comprises a bacterium or bacterial culture.

In a particular embodiment, the protein synthesis system comprises a cell-free protein translation system (in-vitro translation system).

In a particular embodiment, the FRET pair comprises at least one of a fluorescent protein, a fluorescent dye, a quantum dot or a luminescent substance. In a particular embodiment, the luminescent substance comprises a luminescent protein or portion thereof.

In a particular embodiment, the binding of the first label and of the second label independently comprise covalently binding. In a particular embodiment, the binding of the first label and of the second label independently comprise non-covalently binding.

In a particular embodiment, the binding of the first label to the ribosome is at a location on the ribosome at or near at least one of the A site, the P site, the E site or the peptide exit channel site. In a particular embodiment, the location is significantly nearer to one of the A site, the P site, the E site or the peptide exit channel site, relative to the distances between said label and each of the other three sites. In a particular embodiment, the first label is bound to the ribosome at a location that is at a distance of within 5 nm or less from one of the A site, the P site, the E site or the peptide exit channel site, and at a distance of at least 10 nm from each of the other three sites. In a particular embodiment, the location is significantly nearer to the A site, relative to the distances between said label and each of the P site, the E site and the peptide exit channel site. In a particular embodiment, the location is significantly nearer to the P site, relative to the distances between said label and each of the A site, the E site and the peptide exit channel site. In a particular embodiment, the location is significantly nearer to the E site, relative to the distances between said label and each of the A site, the P site and the peptide exit channel site. In a particular embodiment, the location is significantly nearer to the peptide exit channel site, relative to the distances between said label and each of the A site, the P site and the E site.

In a particular embodiment, the binding of the first label to the ribosome comprises binding to an amino acid of the ribosome.

In a particular embodiment, the detecting is performed following a step of irradiating the system with electromagnetic radiation.

In a particular embodiment, the detecting comprises detecting emitted FRET signals with a microscope. In a particular embodiment, the microscope is selected from the group consisting of a confocal microscope and a wide-field microscope.

In a particular embodiment, the detecting comprises detecting FRET signals emitted from the first and second labels in proximity at a single ribosome.

In a particular embodiment, the density of labeled ribosomes in the system is less than about 10 labeled ribosomes per cubic micron. In a particular embodiment, the density of labeled ribosomes in the system is less than about 5 labeled ribosomes per cubic micron. In a particular embodiment, the density of labeled ribosomes in the system is about 0.1 labeled ribosomes per cubic micron. In a particular embodiment, the density of labeled ribosomes in the system is at most 0.1 labeled ribosomes per cubic micron. In a particular embodiment, the density of labeled ribosomes in the system is less than about 0.1 labeled ribosomes per cubic micron. In a particular embodiment, the density of labeled ribosomes is less than about 0.02 labeled ribosomes per cubic micron.

In a particular embodiment, the detecting comprises detecting signals emitted from a single FRET pair. In a particular embodiment, the detecting comprises detecting emitted signals in a single-molecule microscopy system.

In a particular embodiment, the single-molecule microscopy system has a resolution limit of up to 1.0 micron ($\mu$). In a particular embodiment, the single-molecule microscopy system has a resolution limit in the range from 0.1 to 1.0$\mu$. In a particular embodiment, the single-molecule microscopy system has a resolution limit in the x-axis and in the y-axis of up to 0.5$\mu$, and a resolution limit in the z-axis of up to 1.0$\mu$.

In a particular embodiment, the single-molecule microscopy system has an observed volume of at least 0.2$\mu^3$. In a particular embodiment, the single-molecule microscopy system has an observed volume in the range from 0.2 to 1.0$\mu^3$.

In a particular embodiment, the single-molecule microscopy system has a sampling rate of at least 2 frames per second. In a particular embodiment, the sampling rate is at least 5 frames per second.

In a particular embodiment, the density of labeled ribosomes in the single-molecule microscopy system is no greater than 0.1 per pixel. In a particular embodiment, the density of labeled ribosomes is less than 0.04 per pixel. In a particular embodiment, the density of labeled ribosomes is less than 0.02 per pixel.

In a particular embodiment, the detecting comprises detecting FRET signals emitted from a plurality of ribosomes in a single-molecule microscopy system. In a particular embodiment, the detecting is performed in real time.

In a particular embodiment, the detecting comprises measuring at least one of: the sequence of emitted FRET signals, and the timing of emitted FRET signals.

In a particular embodiment, the detecting comprises measuring a parameter selected from the group consisting of: duration of emitted FRET signals; amplitude of donor fluorophore signals; amplitude of acceptor fluorophore signals; amplitude of FRET signals, and a combination thereof.

In a particular embodiment, the detecting comprises measuring emitted FRET signals through at least two optical channels of an optical instrument.

In a particular embodiment, the detecting comprises: detecting a plurality of protein synthetic processes in a single ribosome over a period of time. In a particular embodiment, the plurality of protein synthetic processes comprise a plurality of interactions between a ribosome and a plurality of different tRNA molecules.

In a particular embodiment, the compiling a key comprises detecting at a single location consecutive packets of data, and collecting such data to form a sequence of data packets (SDP). In a particular embodiment, the single location is a single pixel In a particular embodiment, the protein-specific database comprises data based on at least one of labeling sequences; timing sequences; timing sequences with variance; tRNA sequences; protein amino acid sequences, protein amino acid subsequences and mRNA sequences.

In a particular embodiment, the protein-specific database comprises data based on the entire proteome of an organism; the proteome of a specific cell type, tissue or organ; or the proteome of a sub-cellular organelle. In a particular embodiment, the specific cell type is selected from the group consisting of fibroblast, kidney, neuron, astrocyte, myocyte, retinal photoreceptor, CHO, HELA, mesenchymal stem cell and plasma cell.

In a particular embodiment, the sub-cellular organelle is selected from the group consisting of mitochondrion, endoplasmic reticulum, Golgi apparatus, chloroplast and ribosome.

In a particular embodiment, the interrogating a protein-specific database comprises providing a likelihood that a protein entry in the database corresponds to the SDP. In a particular embodiment, the interrogating a protein-specific database comprises aligning the measured sequence of data packets (SDP) to database sequences, and identifying the database entry that best matches the SDP.

In a particular embodiment, the aligning comprises a method selected from the group consisting of sequence alignment using dynamic programming; local sequence alignment; local sequence alignment with complex scores; sequence alignment using Hidden Markov Models; and suboptimal alignment. In a particular embodiment, the protein-specific database comprises labeling information, and the aligning is performed by local sequence alignment with complex scores.

In a particular embodiment, the protein-specific database comprises data based on all of labeling sequences, timing sequences, and timing sequences with variance, and the aligning is performed by local sequence alignment.

In a particular embodiment, the protein-specific database comprises data based on tRNA sequences, and the aligning is performed by sequence alignment using Hidden Markov Models.

In a particular embodiment, the protein-specific database comprises subsequences of protein sequences, wherein each subsequence entry is linked to a set of proteins that contain the subsequence, and the interrogating comprises identifying the subsequence most likely to have produced the measured SDP.

According to another aspect, the present invention provides an apparatus for identifying one or more proteins synthesized in a protein synthesis system, the apparatus comprising:

a container for containing a plurality of components of the system, wherein the components comprise at least one first label bound to at least one ribosome or a fragment thereof; at least one second label bound to at least one tRNA or to at least one amino acid; wherein one of the first and second label is a donor fluorophore, and the other is an acceptor fluorophore, and wherein the donor fluorophore and the acceptor fluorophore together form a fluorescence resonance energy transfer (FRET) pair;

a detection system for measuring FRET signals emitted from a single ribosome in the system during protein synthesis when the first label and the second label are in proximity; and a computational device for compiling a key from the detected FRET signals; and further for interrogating a protein-specific database with said key.

In a particular embodiment, the first label is a donor fluorophore and the second label is an acceptor fluorophore. In a particular embodiment, the first label is an acceptor fluorophore and the second label is a donor fluorophore. In a particular embodiment, a donor fluorophore is bound to a ribosome or a fragment thereof, and an acceptor fluorophore is bound to a tRNA. In a particular embodiment, a donor fluorophore is bound to a ribosome or a fragment thereof, and an acceptor fluorophore is bound to an amino acid. In a particular embodiment, an acceptor fluorophore is bound to a ribosome or a fragment thereof, and a donor fluorophore is bound to a tRNA. In a particular embodiment, an acceptor fluorophore is bound to a ribosome or a fragment thereof, and a donor fluorophore is bound to an amino acid. In a particular embodiment, one donor fluorophore is bound to a ribosome or a fragment thereof, and at least two different acceptor fluorophores are bound to two different tRNAs.

Embodiments of the protein synthesis system and of the FRET pair include those hereinbefore disclosed.

In a particular embodiment, either or both of the first label and the second label are covalently bound. In a particular embodiment, either or both of the first label and the second label are non-covalently bound.

In a particular embodiment, the first label is bound to the ribosome at a location on the ribosome at or near at least one of the A site, the P site, the E site or the peptide exit channel site. In a particular embodiment, the location is significantly nearer to one of the A site, the P site, the E site or the peptide exit channel site, relative to the distances between said label and each of the other three sites. In a particular embodiment, the location is at a distance of within 5 nm or less from one of the A site, the P site, the E site or the peptide exit channel site, and at a distance of at least 10 nm from each of the other three sites.

In a particular embodiment, the location is significantly nearer to the A site, relative to the distances between said label and each of the P site, the E site and the peptide exit channel site. In a particular embodiment, the location is significantly nearer to the P site, relative to the distances between said label and each of the A site, the E site and the peptide exit channel site. In a particular embodiment, the location is significantly nearer to the E site, relative to the distances between said label and each of the A site, the P site and the peptide exit channel site. In a particular embodiment, the location is significantly nearer to the peptide exit channel site, relative to the distances between said label and each of the A site, the P site and the E site.

In a particular embodiment, the first label is bound to an amino acid of the ribosome. In a particular embodiment, the first label is bound to a ribosomal protein selected from the group consisting of ribosomal protein L1, ribosomal protein L11, S1, ribosomal protein S21, and a combination thereof.

In a particular embodiment, the detection system comprises a radiation source for irradiating the system with electromagnetic radiation.

In a particular embodiment, the detection system comprises a microscope. In a particular embodiment, the microscope is selected from the group consisting of a confocal microscope and a wide-field microscope.

In a particular embodiment, the density of labeled ribosomes in the system is less than about 10 labeled ribosomes per cubic micron. In a particular embodiment, the density of labeled ribosomes in the system is less than about 5 labeled ribosomes per cubic micron. In a particular embodiment, the density of labeled ribosomes in the system is about 0.1 labeled ribosomes per cubic micron. In a particular embodiment, the density of labeled ribosomes in the system is at most 0.1 labeled ribosomes per cubic micron. In a particular embodiment, the density of labeled ribosomes in the system is less than about 0.1 labeled ribosomes per cubic micron. In a particular embodiment, the density of labeled ribosomes is less than about 0.02 labeled ribosomes per cubic micron.

In a particular embodiment, the detection system is for detecting emitted radiation occurring from a single FRET pair. In a particular embodiment, the detection system comprises a single-molecule microscopy system. Embodiments of the single-molecule microscopy system are as herein before described.

In a particular embodiment, the single-molecule microscopy system is for detecting FRET signals emitted from a plurality of ribosomes.

In a particular embodiment, the detection system is for measuring the sequence of FRET signals emitted from the first and second labels when in proximity. In a particular embodiment, the detection system is for measuring at least one of: the sequence of emitted FRET signals, and the timing of emitted FRET signals. In a particular embodiment, the detection system is for measuring a parameter selected from the group consisting of: duration of emitted signals; amplitude of donor fluorophore signals; amplitude of acceptor fluorophore signals; amplitude of FRET signals, and a combination thereof.

In a particular embodiment, the detection system is for measuring emitted FRET signals through at least two optical channels. In a particular embodiment, the detection system is for detecting a plurality of protein synthetic processes in a single ribosome over a period of time.

In a particular embodiment, the computational device is for detecting consecutive packets of data at a single location, and collecting such data as a sequence of data packets (SDP). In a particular embodiment, the single location is a single pixel.

Embodiments of the protein-specific database include those hereinbefore disclosed.

In a particular embodiment, the computational device is for providing a likelihood that a protein entry in the database corresponds to the SDP. In a particular embodiment, the computational device is for aligning the measured sequence of data packets (SDP) to the database sequences, and identifying the database entry that best matches the SDP.

In a particular embodiment, the aligning comprises an alignment method selected from the group consisting of sequence alignment using dynamic programming; local sequence alignment; local sequence alignment with complex scores; sequence alignment using Hidden Markov Models; and suboptimal alignment.

According to another embodiment, there is provided a method for analyzing a chemical compound library, the method comprising: individually administering a plurality of compounds from the chemical compound library to a protein translation system; measuring a response of the system according to the method described above; so as to provide information on the effect of each tested compound on protein translation.

According to another embodiment of the present invention, there is provided an apparatus for analyzing a chemical compound library, comprising: a well array plate comprising a plurality of wells; a robot for placing a protein synthesis system into the wells; a robot for administering chemical compounds into the wells; and an apparatus as previously described to analyze protein synthesis by the system.

According to still another embodiment of the present invention, there is provided a method for determining cellular protein pathways, comprising: selecting a cellular or bacterial culture; placing the culture in a plurality of sample containers; subjecting the culture to at least one condition in each of the containers; measuring protein synthesis in each of the containers as previously described; and analyzing protein expression patterns in all containers to determine protein pathways.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 14A-14D describe a simulation of an illustrative method for signal processing according to the present invention.

DETAILED DESCRIPTION OF THE INVENTION

Abbreviations and Definitions

Figure 1A:
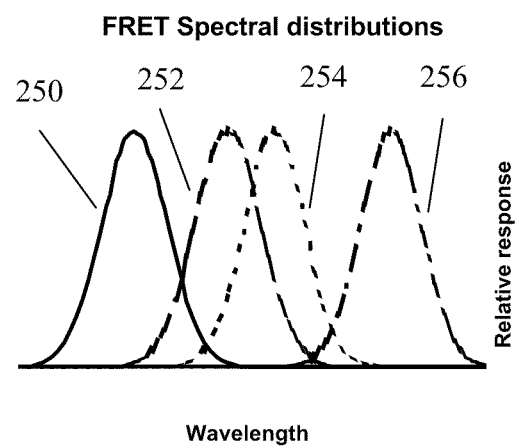
FIGS. 1A-1B describe the properties of a FRET pair and the dependence of the FRET effect on pair distance.

ADME-TOX: A set of parameters relevant to drug candidates that should be measured prior to clinical trials (Absorption, Distribution, Metabolism, and Excretion) and TOX (Toxicity)

APD: Avalanche photodiode, a sensitive detector of faint optical energy.

CCD: Charge coupled device, a photo sensitive semiconductor device usually arranged as a one- or two-dimensional array of photo sensitive cells.

CHO: Chinese hamster ovary cell line.

CSOM: Confocal scanning optical microscope.

FRET: Fluorescence Resonance Energy Transfer, refers to the transfer of energy between molecules without photon exchange which occurs under suitable conditions. In this phenomenon, a donor fluorophore excited by incident light transfers at least some of its energy to a nearby acceptor. A necessary condition is that the emission spectrum of the donor must overlap with the excitation spectrum of the acceptor. FRET may be used, inter alia to determine molecular distances of the order of few nanometers using appropriate fluorophores.

FWHM: Full width half maximum, a measure of signal resolution in spectrometry.

GPCR: Cell surface receptors that are coupled to heterotrimeric G-proteins (GTP-binding proteins).

HTS: High throughput screening, a method used in drug discovery by which a large library of chemical compounds is assayed for binding to a specific receptor.

ICAT: a method of sample tagging that allows relative quantitation of proteins in two samples using LC-MS-MS.

LC-MS: a mass spectrometer that is directly coupled to a liquid chromatography column, and where ionization commonly is achieved with the electrospray method.

LC-MS-MS: a mass spectrometer of the LC-MS type where ions are further fragmented and the mass spectrum of the fragments is measured. Often used to identify sequences of tryptic peptides.

MALDI-TOF: mass spectrometer that ionizes the sample with the technique of matrix-assisted laser desorption ionization, and measures masses using a time-of-flight mass analyzer.

NA: numerical aperture (of a lens).

ORF: Open reading frame. A putative protein-encoding gene.

PCR: Polymerase chain reaction, a method for in-vitro amplification of DNA.

PEG: polyethylene glycol, a surface treatment agent that aids in immobilization of biomolecules for optical analysis.

PMT: photomultiplier tube, a sensitive photodetector.

PSM: Protein synthesis monitoring, an acronym for at least some aspects of the present invention.

tRNA: transfer RNA, the adaptor molecule that delivers amino acids to the ribosome.

mRNA: messenger RNA, the sequence of messenger RNA nucleic acids according to which a protein is translated.

rRNA: ribosomal RNA, one of the RNA strands that are part of the ribosome.

SHIM: Second harmonic imaging microscopy.

TIR: Total internal reflection, a microscopy illumination method that illuminates a very volume at the interface of two materials with different refractive indices.

TIR-FM: total internal reflection fluorescent microscopy.

TPE: two photon excitation, an illumination method for special microscopy applications.

TPM: Two photon microscopy, a microscopy system that uses TPE illumination.

Y2H: A method for detecting protein-protein interaction in-vivo in *Saccharomyces cerevisiae*.

The term "labeling sequence" as used herein refers to a sequence of numerical identifiers, based on both (i) the amino acid sequence of a protein, or its corresponding mRNA sequence, or a tRNA sequence as defined below, and (ii) a labeling strategy in which one or more amino acids or tRNAs are modified by attachment of a label(s). To produce the labeling sequence, numerical identifiers assigned to each type of labeled amino acid or tRNA ("sequence element") are sequentially arranged according to the sequence element expected to be processed by a ribosome in accordance with the amino acid sequence of the protein. The labeling sequence additionally includes numerical identifier(s) indicating the absence of a sequence element.

The term "timing sequence" as used herein refers to the sequence of expected time differences between signals emitted from differently spaced fluorophores as a polypeptide chain is synthesized by the ribosome. A timing sequence may be measured from a single experiment, compiled from multiple experiments, or obtained from a mathematical model.

The term "timing sequence with variance" as used herein refers to a timing sequence as above, with its variance, based either on a measurement or a model-based prediction.

The term "sequence of emitted FRET signals" as used herein refers to the order of a series of FRET signals measured over the course of a FRET assay.

The term "timing of emitted FRET signals" as used herein refers to the temporal characteristics of a series of FRET signals measured over the course of a FRET assay, The term "amino acid sequence" as used herein refers to the sequence of amino acid residues of a protein.

The term "tRNA sequence" as used herein refers to a sequence of tRNA molecules, denoted by a sequence of $X_i$ identifiers, that is expected to be used for the processing of a particular mRNA by a ribosome during the synthesis of a particular protein. In humans, 49 specific tRNA molecules exist (including that carrying selenocysteine), wherein 1 to 5 different tRNA molecules may be charged with a specific amino acid. The combination of a particular amino acid, and the specific tRNA molecule which is charged with that amino acid is denoted herein as $X_i$, wherein X is the single letter identification of the amino acid and i identifies the specific tRNA molecule used for that amino acid, wherein $1 \leq i \leq 5$.

The term "packet of data" as used herein refers to an entire collection of digital data measured and recorded from a single FRET signal.

The term "key" as used herein refers to a sequence of measured digital data which may be used for example, for interrogating a database.

The term "compiling" and grammatical variations thereof as used herein refers to a process of accumulating and arranging digital data.

The term "proteome" as used herein refers to the total array of proteins expressed or capable of expression in a particular organism, organelle, cell type, tissue, metabolic state, disease state, stage of development or combination thereof.

The term "near" as used herein in reference to the distance between the site or location on a ribosome at which a fluorophore label is bound and a different site on the same ribosome, means a distance within about 5 nm or less.

The term "significantly nearer" as used herein in reference to a site or location on a ribosome at which a fluorophore label is bound and its distance in relation to one or more different sites on the same ribosome, means that the distance between the label and a first particular site is 50% or less than the distance between the label and a second particular site.

The term "labeled ribosome" as used herein refers to a ribosome comprising a fluorophore label bound thereto.

In order to better describe the disclosure, current technologies that the invention may optionally use are briefly explained. It should be noted that all references given in this application are hereby incorporated by reference as if fully set forth herein.

Fluorescent Resonance Energy Transfer (FRET)

Fluorescence resonance energy transfer—FRET—has been known for over 50 years (Ha, T., *Single-molecule Fluorescence resonance energy transfer*, Methods 25, 78-86 (2001), review; DeAngelis, D. A., *Why FRET over genomics*? Physiol. Genomics 1999, 31; 1 (2): 93-9; Selvin, P. R., *The renaissance of fluorescence resonance energy transfer*, Nat. Struct. Biol. 2000 September; 7 (9):730-4; Kenworthy, A. K., *Imaging Protein-Protein Interactions Using Fluorescence Resonance Energy Transfer Microscopy*, Methods. 2001 July; 24 (3):289-96). The technology allows measurement of distances in the nanometer scale up to about 10 nanometers. It relies on a quantum-mechanical principle where, under suitable conditions, energy is transferred between molecules without photon exchange. For FRET to occur, a donor fluorophore is excited by incident light while an acceptor fluorophore is nearby. The emission spectrum of the donor must overlap with the excitation spectrum of the acceptor. In this configuration, some of the energy is transferred from donor to acceptor without generation of photons. This causes the excitation of the acceptor molecule, and consequently the emission of a fluorescent photon in the natural fluorescent frequency of the acceptor. Thus, when FRET occurs, donor emission decreases and acceptor emission increases as the distance between them diminishes. The energy transfer efficiency obeys the relationship $E \propto [1+(R/R_0)^6]^{-1}$, where R is the distance between donor and acceptor and $R_0$ is a constant that depends on donor-acceptor configuration and characteristics.

In particular embodiments of the invention, the first label is bound to the ribosome at a site or location on the ribosome that is at or near at least one of the A site, the P site, the E site or the peptide exit channel site. This is to ensure sufficient proximity between the first label and the second label for FRET to occur at optimally detectable levels during the protein translation process. Since the second label is bound to a tRNA or an amino acid, and those molecular components are brought into association with the ribosome during the translation initiation, elongation and termination steps, the first and second labels approach each other at decreasing distances during that cycle. Accordingly, the first label is preferably localized on the ribosome so as to optimize the relationship described above.

Thus, the first label is bound to the ribosome at a location that is significantly nearer to one of the A site, the P site, the E site or the peptide exit channel site, relative to the distances between said label and each of the other three sites. In a currently preferred embodiment, the first label is bound to the ribosome at a location that is at a distance of within 5 nm or less from one of the A site, the P site, the E site or the peptide exit channel site, and at a distance of at least 10 nm from each of the other three sites.

In a particular embodiment, the location is significantly nearer to the A site, relative to the distances between said label and each of the P site, the E site and the peptide exit channel site. In an alternate embodiment, the location is significantly nearer to the P site, relative to the distances between said label and each of the A site, the E site and the peptide exit channel site. In a still alternate embodiment, the location is significantly nearer to the E site, relative to the distances between said label and each of the A site, the P site and the peptide exit channel site. In a different embodiment, the location is significantly nearer to the peptide exit channel site, relative to the distances between said label and each of the A site, the P site and the E site.

Figure 1B:
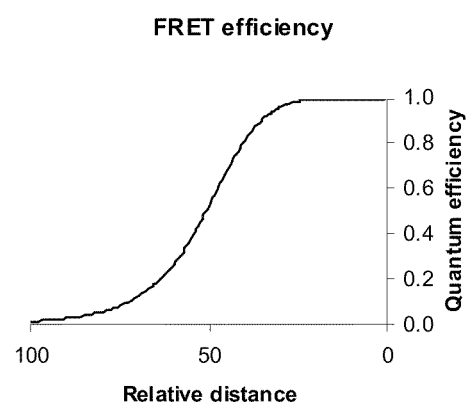

FIGS. 1A-1B show a diagram of FRET pair configuration. In FIG. 1A the spectral graphs of donor excitation 250, donor emission 252, acceptor excitation 254 and acceptor emission 256 are shown. Note the overlap between the spectral responses of donor emission and acceptor excitation. In FIG. 1B the efficiency of energy transfer is shown as a function of donor-acceptor normalized distance ($R_0$ is equivalent to 50 in this chart).

In particular embodiments of the invention, the detection step involves measurement of one or more of: the sequence of emitted FRET signals; the timing of emitted FRET signals; duration of emitted FRET signals; amplitude of emitted FRET signals; amplitude of donor fluorophore signals; amplitude of acceptor fluorophore signals, and a combination thereof.

In FRET assays, three signal channels may be measured, namely, (i) the donor channel, by excitation of donor fluorophore and measurement of donor fluorophore signal emission; (ii) the acceptor channel, by excitation of acceptor fluorophore and measurement of acceptor fluorophore signal emission; and (iii) the FRET channel (also referred to as the "sensitized emission" channel), by excitation of donor fluorophore and measurement of acceptor fluorophore signal emission. Is general, all three of these independent signal channels are used for sensitive and reliable detection of the FRET signals. In some cases however, a subset of the three channels may be used, always including at least the FRET channel.

FRET has been recently used to sequence DNA (Bralaysky, I., *Sequence information can be obtained from single DNA molecules*, Proc Natl Acad Sci USA., 2003 Apr. 1; 100 (7):3960-4), monitor cellular events in live cells (Zlokrnik et al., *Quantitation of transcription and clonal selection of single living cells with beta-lactamase as reporter*, science 1998 Jan. 2; 279 (5347):84-8)), create sensitive biochemical sensors (Medintz et al., *Self-assembled nanoscale biosensors based on quantum dot FRET donors*, Nat. Mater. 2003 September; 2 (9):630-8), perform real time sequencing of DNA or RNA (PCT application WO 01/16375 to Schneider and Rubens) and monitor protein-protein interactions or protein kinetics (Jia et al., *Nonexponential kinetics of a single tRNA-Phe molecule under physiological conditions*. Proc Natl Acad Sci USA. 1997 Jul. 22; 94 (15):7932-6). Numerous ingenious variants of the technique have been used successfully both in-vitro and in-vivo, both in bulk and in single molecule setting. One common application is the real-time monitoring of inter-molecular distances. Indeed, using FRET, it is becoming common nowadays to observe dynamics of single molecular events, in real time, in living cells.

In one preferred embodiment, FRET architecture makes use of a donor-quencher pair rather than a donor-acceptor architecture; for this optional embodiment, the donor-quencher pair forms the marker. This implementation is a more robust architecture, allowing the use of metal and other particles instead of fluorescent biomolecules. In this embodiment, the signal measured is in fact the donor signal, interrupted by periods of quenching.

The Ribosome and the Mechanism of Translation

The structure of the ribosome and the mechanism of translation, as have been revealed by recent work, are reviewed herein (Alberts, B., Johnson, A., Lewis, J., Raff. M., Roberts, K., and Walter, P., *Molecular Biology of the Cell*, 4th ed, 2002, Garland Science, N.Y.; Ramakrishnan, V., *Ribosome Structure and the Mechanism of Translation*, 2002, Cell 108 557-572; Schlunzen, F. et al., *Structural basis for the interaction of antibiotics with the petidyl transferase center in eubacteria*, 2001, Nature 413 814-821; Sytnik, A. et al., *Peptidyl Transferase Center Activity Observed in Single Ribosomes*, 1999, J. Mol. Biol. 285, 49-54; Nyborg, J., and Liljas, A., *Protein biosynthesis: structural studies of the elongation cycle*, 1998, FEBS letters 430, 95-99).

The ribosome itself is composed of two subunits, termed 30S and 50S (there are differences between bacterial and eukaryotic ribosomes—henceforth in this discussion the ribosome is presumed to come from *E. coli*, although this assumption is made for the purposes of description only and without any intention of being limiting in any way). The large unit is composed of a pair of large RNA molecules (5S and 23S), the small subunit of a single RNA molecule (30S). Each unit has several dozen small proteins attached to it (Alberts, B., Johnson, A., Lewis, J., Raff. M., Roberts, K., and Walter, P., *Molecular Biology of the Cell*, $4^{th}$ ed, 2002, Garland Science, N.Y.). The ribosome reads the code on mRNA molecules and synthesizes the encoded protein through the mediation of tRNA molecules. The process is performed in three stages: initiation, elongation and termination.

Figure 2A:
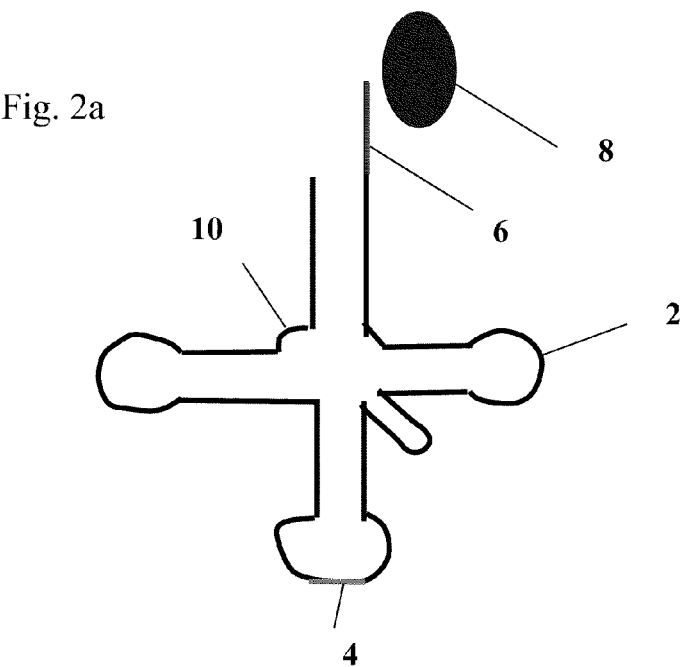
FIG. 2A describes the tRNA molecule.

The ribosome uses an adaptor molecule—transfer RNA, or tRNA. These molecules are a special type of RNA. At one end, they have the anticodon part that binds to the RNA codon. At the other end, they carry the amino acid corresponding to that codon. FIG. 2A shows a tRNA molecule 2, with the anticodon loop 4, the amino acid arm 6, and a loaded amino acid 8. The tRNA molecules have a cycle of being charging with amino acid and discharging. Charging, or attachment of amino acids to the tRNA molecules, is performed by the aminoacyl-synthetase enzyme family. Discharging is performed by the ribosome, serving as a ribozyme (RNA enzyme).

When tRNA is tagged (as for example with a fluorescent label), the tRNA should continue to function normally during the processes of becoming charged with an amino acid, attaching to the elongation factors, and traveling through the ribosome. Several tagging schemes have made use of the shoulder 10 of the molecule in order to create fluorescent labeling schemes that are efficient on the one hand and result in a fully functional tRNA molecule on the other hand. Several studies have shown that *E. coli* tRNAs (tRNA molecules) can be efficiently labeled at position 8, which has in many cases a 4-thiouridine base, and at position 47, which has in several cases an amine-reactive X-base (see table below; it should be noted that these position numbers are given according to a standard numbering system for tRNA molecules). tRNA functionality requires that the molecule interact properly with the aminoacyl synthetases on the one hand, and with the ribosomal machinery (including the elongation factors) on the other. tRNA recognition by aminoacyl synthetases is known to be particularly dependent on the anticodon part and the amino acid arm locus.

Figure 2B:
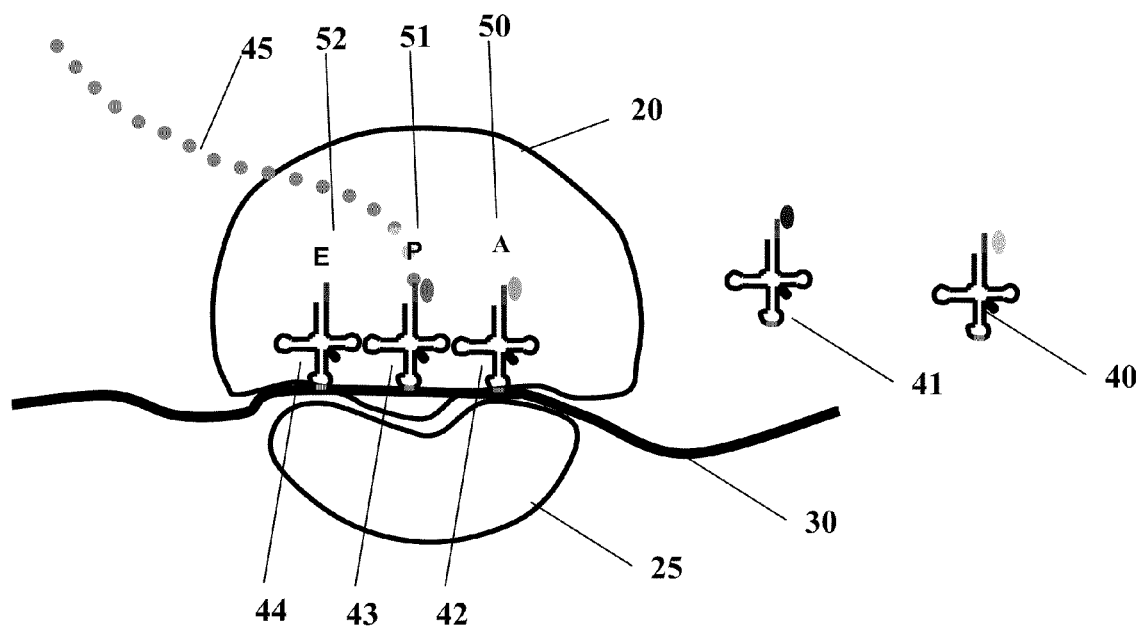
FIG. 2B describes the basic structure of a ribosome and the elongation cycle.

There are three important stages in translation: initiation, elongation and termination. For monitoring protein synthesis, where protein identification is a preferred motivation, the important stage is elongation. FIG. 2B shows a schematic description of bacterial ribosome structure with the larger (50S) subunit 20, smaller (30S) subunit 25, aminoacyl (A) site 50 where tRNAs dock initially, peptidyl (P) site 51 where the growing polypeptide chain is docked, and exit (E) site 52 from where the deacylated tRNA is removed once the cycle is complete. Also shown are tRNAs that are undocked yet 40 and 41 to show that the cycle may continue further, mRNA being decoded 30 and the nascent polypeptide chain being synthesized 45. The ribosome itself is made up of large folded rRNA chains with ribosomal proteins. The larger subunit 20 contains two folded rRNAs, known as 23S and 5S. The smaller subunit 25 contains one folded rRNA, 30S (not shown). On the folded rRNA chains more than 50 ribosomal proteins are docked (not shown). They are customarily denoted by L1, L2 etc for the approximately 36 ribosomal proteins attached to the large subunit, and by S1, S2 etc for the approximately 21 ribosomal proteins attached to the small subunit (numbers given are correct for *E. coli* ribosomes).

Three docked tRNAs are seen in FIG. 2B. The first 42 is in the A (Aminoacyl) site; the second 43 in the P (Peptidyl) site, and the amino acid it carries is at this point connected to the nascent peptide; the third 44 is in the E (exit) site, it has been discharged from the amino acid and will be ejected shortly from the ribosome. The heavy line 30 indicates the mRNA being translated, and the dotted line 45 represents the polypeptide being synthesized, tied into the Peptidyl position.

The main stages of elongation are as follows. Stage 1: Codon recognition. A tRNA molecule carrying an amino acid binds to a vacant A-site, while the nascent polypeptide is attached to the P-site. Stage 2: Peptide bond creation. A new peptide bond is created and the polypeptide chain is moved to the A-site. Stage 3: Translocation. The ribosome translocates a distance of 3 nucleotides with respect to the mRNA, the two tRNA units and the polypeptide chain. Stage 4: the cycle repeats itself until a stop codon is reached.

Figure 3A:
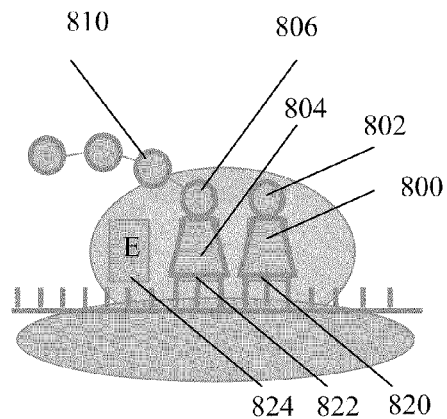
FIGS. 3A-3C describe the stages of the elongation cycle.
Figure 3B:
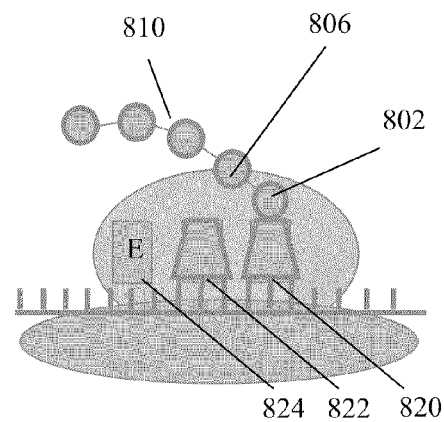
Figure 3C:
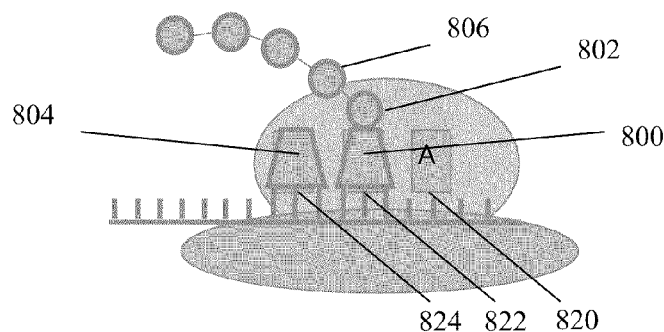

This cycle is shown as schematic diagrams in FIGS. 3A-3C. Stage 1—Codon recognition—is shown in FIG. 3A. A tRNA molecule 800 carrying an amino acid 802 binds to a vacant A-site 820, while the growing polypeptide chain 810 is attached to amino acid 806 on tRNA 804 that is docked in the P-site 822. At this stage E site 824 is shown as empty. Stage 2, peptide bond formation, is shown in FIG. 3B. A new peptide bond is created between amino acid 806 and amino acid 802, and the polypeptide chain 810 is moved to the A-site 820. Stage 3, translocation, is shown in FIG. 3C. The ribosome translocates 3 nucleotides with respect to the mRNA, the two tRNA units 800 and 804, and the polypeptide chain 810. Stage 4: the cycle repeats itself until a stop codon is reached.

Single Molecule Detection

In recent years, the technology of single molecule detection by fluorescent spectroscopy has advanced considerably. This has been aided by novel microscopy methods; improved radiation sources, cameras and detectors; novel, highly efficient fluorescent labels in the visible range; and novel labeling techniques. The achievements of single molecule fluorescent spectroscopy are numerous. It has allowed us to measure dynamic behavior and reaction kinetics of individual biological molecules inside living cells, and provided a direct way to quantify, with a high spatial and temporal resolution, biological events inside cells at the single-molecule level. Kinetics of a single molecule have been demonstrated (Zhuang et al., *Correlating structural dynamics and function in single ribozyme molecules. Science.* 2002 May 24; 296 (5572):1473-6), individual ion channels have been studied in-vivo (Harms, G. S. et al., *Single-Molecule Imaging of L-Type Ca2+ Channels in Live Cells,* 2001, Biophysical Journal 81, 2639-2646), DNA sequencing has been performed using optical methods with single DNA molecules (Braslaysky et al., *Sequence information can be obtained from single DNA molecules*, Proc Natl Acad Sci USA. 2003 Apr. 1; 100 (7):3960-4) translation by single ribosomes has been observed and measured (Vanzi et al., *Protein synthesis by single ribosomes*, RNA (2003), 9:1174-1179), Ribosome activity was measured in single ribosomes (A. Sytnik et al., *Peptidyl Transferase Center Activity Observed in Single Ribosomes*, J. Mol. Biol. 285, 49 (1999), protein denaturation has been studied (Deniz, A. A., et al., *Single-molecule protein folding: Diffusion fluorescence resonance energy transfer studies of the denaturation of chymotrypsin inhibitor 2,* 2000, PNAS 97 (10), 5179-5184). Numerous additional applications have been reported: direct observation of the motions of molecular motors, enzymatic reactions, structural dynamics of proteins and DNA-protein interactions in-vitro; single lipid molecules in a lipid bilayer have been visualized, ligand-receptor reactions and lipid molecule movements have been visualized as single molecules on the surface of living cells. The technique has been reviewed extensively, as, for example, in the following references, incorporated herein in their entirety as if fully set forth: Sako, Y., and Yanagida, T, Single-molecule visualization in cell biology, Nat Rev Mol Cell Biol. 2003 September; Suppl:SS1-5. Review; Schwille, P. and Kettling, U., *Analyzing single protein molecules using optical methods,* 2001, Current Opinion Biotech., 12:382-386; Weiss, S., *Fluorescence Spectroscopy of Single Biomolecules,* 1999, Science 283, 1676-1683.

Most important for the present invention is the technology of single molecule FRET detection (single pair FRET—spFRET). In this technique, FRET pairs are attached to the biomolecules of interest, whether in-vitro or in-vivo, and observed by a single-molecule microscopy system. If the FRET pairs are separated by distances that are within the resolution limit of the imaging device, single interactions can be observed. Thus, FRET technique combines naturally with single molecule detection methods. A good practical review of the technology and its usage can be found in Ha, T, *Single-molecule fluorescence resonance energy transfer,* METHODS 25, 78-86 (2001).

There are several parameters which are important for single molecule detection in general, and single pair FRET in particular. One is the reduction of background noise and background fluorescence. Both in-vitro and in-vivo, the molecules to be detected are surrounded by a complex molecular environment that emits radiation at any recorded frequency. The solution to this background noise involves reduction of the observed volume. This can be achieved in several ways. Confocal microscopy limits the observed volume to the order of $10^{-15}$ L, which is sufficient for many applications. Total internal reflectance is an illumination mode that uses the phenomenon of evanescent wave (Toomre D, and Manstein D J, *Lighting up the cell surface with evanescent wave microscopy*, Trends Cell Biol. 2001 July; 11 (7): 298-303). With this illumination mode only a slab whose thickness is just about a hundred nanometers above the slide surface is illuminated. Another method that is becoming widespread is two-photon microscopy. With two-photon microscopy, the illumination radiation has approximately half the required excitation energy (i.e., half the frequency or double the wavelength). Only when the fluorophore interacts simultaneously with two photons will it be excited. This reaction requires a very high photon intensity, which occurs only in the focus of the illumination beam, thus allowing drastic reduction of the excitation volume while bringing the background fluorescence to practically zero.

Another important parameter for our application is the sampling rate, or frame rate of the system. In prokaryotes, the ribosome synthesizes polypeptides at the rate of about 20 amino acids per second. In eukaryotes the rate is about an order of magnitude lower. If the FRET signal is assumed to be "on" for about half the synthesis cycle, and if at least 4-5 samplings are required for reliable detection, then a sampling rate of about 200 frames per second is required for prokaryotes.

It is preferable that the system be able to monitor a number of active ribosomes simultaneously. A ribosome has a diameter of about 20 nM, and the distance between two ribosomes (on the same mRNA strand) is on the order of 40 nM. The resolution of standard optical microscopes, at their diffraction limit, is about 180 nM, and for practical resolution of active PSM signals we should assume a distance at least 4 times larger. Thus, a realistic computation assumes one PSM signal per square micron. In a system with pixel size 0.1 micron and field of 1000×1000 pixels, the field of view is 100 microns square, which typically holds 100 eukaryotic cells and can resolve hundreds and even thousands of ribosomes.

Another important point is photobleaching of the fluorophores. When a fluorescent dye is excited it is susceptible to oxidation or photobleaching. With standard fluorophores such as naturally fluorescent proteins or small organic dyes, bleaching can be minimized both by eliminating as far as possible the sample exposure to oxygen, and on the other hand employing an enzymatic oxygen scavenger system. Singlet oxygen is presumed to be the main culprit in photobleaching, and in some cases oxygen removal has a considerable effect on reducing photobleaching (cf. T. Ha, METHODS 25, 78-86 (2001)). If the system in use is two-photon microscopy, than photobleaching is reduced considerably compared to confocal microscopy, especially because of the significant or even near complete reduction in background excitation. Another configuration that helps lengthen the signal generation time is the use of quantum dots, which are practically immune to bleaching. When quantum dots are used as donors, and if the excitation radiation is well outside the excitation spectrum of the acceptor, very long monitoring times can be expected.

In a particular embodiments of the invention, emitted FRET signals are detected in a single-molecule microscopy system. In exemplary embodiments, the single-molecule microscopy system has a resolution limit of up to 1.0 micron ($\mu$), such as in the range from 0.1 to 1.0$\mu$. In other particular embodiments, the single-molecule microscopy system has a resolution limit in the x-axis and in the y-axis of up to 0.5$\mu$, and a resolution limit in the z-axis of up to 1.0$\mu$.

In other particular embodiments, the single-molecule microscopy system has an observed volume of at least 0.2$\mu^3$, such as in the range from 0.2 to 1.0$\mu^3$. As used herein, the term "observed volume" refers to the region in space imaged by a single pixel.

In still other particular embodiments, the single-molecule microscopy system has a sampling rate of at least 2 frames per second, or least 5 frames per second.

In yet other particular embodiments, the density of labeled ribosomes in the single-molecule microscopy system is no greater than 0.1 per pixel. For example, the density of labeled ribosomes may be less than 0.04 per pixel, or less than 0.02 per pixel.

Novel Fluorescent Technology—Natural Proteins, Organic Dyes and Quantum Dots

Over the last years, important advances have been made in fluorescent marker technology. First, a large variety of naturally fluorescent proteins have been found. These enable a wide variety of in-vivo labeling strategies (cf. Miyawaki, A., Sawano, A. and Takako, K. *Lighting up cells: labeling proteins with fluorophores*. Nat Cell Biol. 2003 September; Suppl:S1-7. Review.). Fluorescent proteins can be found with excitation peaks from 382 nm (BFP—blue fluorescent protein)) to 590 nm (HcRed1), and emission peaks between 448 and 618 nm for these proteins, respectively. Naturally fluorescent proteins are particularly useful for in-vivo labeling in the form of fusion proteins. Fusion proteins are engineered proteins whose amino acid sequence includes two parts: the first part contains the sequence of the fluorescent marker protein and the second part contains the protein of interest to which the fluorescent marker is attached. Fusion proteins with naturally fluorescent proteins can be generated using the method of Baubet et al. (Proc. Natl. Acad. Sci. USA 97:7260-5, 2000, herein incorporated by reference).

Green fluorescent protein (GFP) and its derivatives include a chromophore built of amino acids located in the center of the molecule. GFP excels in being photostable as well as having numerous variants with a choice of excitation and emission wavelengths (U.S. Pat. Nos. 5,626,058 and 5,777,079; Herzenberg et al., Clin Chem. 2002 October; 48 (10): 1819-27; Hailey et al., Methods Enzymol. 2002; 351:34-49). GFP can be attached to a ribosomal protein through the method of generation of a fusion protein, by well-known recombinant techniques as explained, for example, in *Molecular Cloning, A Laboratory Manual*, cold Spring Harbor Laboratory, Cold Spring Harbor, N.Y., chapter 17, 1989, herein incorporated by reference. A cell that is engineered to produce this fusion protein can produce ribosomes that include the engineered ribosomal protein as required. A comprehensive treatment of green fluorescent protein is Chalfie, M. & Kain, S. (1998) *Green fluorescent protein: properties, applications, and protocols*, eds. Chalfie, M. & Kain, S. (Wiley-Liss, New York), herein incorporated by reference.

Another relevant technology is that of semiconductor quantum dots, which has matured sufficiently to be used routinely to label biomolecules (Jovin, T. M., *Quantum dots finally come of age*, Nat. Biotechnol. 2003 January; 21 (1): 32-3 and references therein, Medintz, I. L. et al., *Self-assembled nanoscale biosensors based on quantum dot FRET donors*, Nat. Mater. 2003 September; 2 (9):630-8). Quantum dots are currently manufactured as colloidal inorganic semiconductor nanocrystals consisting of a CdSe core and a ZnS cap. The absorption spectra of these dots are very wide, while the emission is very narrow (20-40 nm FWHM). The emission spectrum can be controlled by the size of the dot, where larger dots emit longer wavelengths. Most importantly, quantum dots are practically immune to photobleaching, such that monitoring can optionally be performed for minutes or even hours, in contrast with traditional probes, that may bleach out after a few seconds. This is important for this optional application since a protein synthesis monitoring system should be able to monitor protein production over a period of hours.

The application of quantum dots to biomolecules labeling was hampered by several technical difficulties which were recently overcome. Powerful applications of quantum dots have been recently published. In Jaiswal et al., Nat. Biotechnol. 21, 47-51 (2003), HeLa cells labeled by endocytosis of quantum dots coated with DHLA retained the internalized dots and continued to grow for more than a week. In Wu et al., Nat. Biotechnol. 21 41-46 (2003), successful targeting of quantum dots to a cell surface receptor, cytoskeletal components and nuclear antigens were demonstrated. In Medintz, I. L. et al., "*Self-assembled nanoscale biosensors based on quantum dot FRET donors*", Nat. Mater. 2003 September; 2 (9):630-8, a hybrid inorganic-bioreceptor sensor has been produced, where the quantum dot serves as FRET donor and an organic dye as a quencher. The use of a quantum dot as a FRET donor is an important optional application for the present invention, as discussed below.

Several techniques for In-vivo labeling with quantum dots have been developed, including endocytic uptake and selective labeling of cell surface proteins with quantum dots conjugated to antibodies are described in (Jaiswal et al., ref above). Quantum dots, individually encapsulated in phospholipid block-copolymer micelles have been injected into *Xenopus* embryo cells, and the embryo development has been followed for several days (Dubertret et al., "*In-vivo imaging of quantum dots encapsulated in phospholipid micelles*", Science. 2002 Nov. 29; 298 (5599):1759-62).

Quantum dots are commercially available from Quantum Dot Corporation, Hayward, Ca. These are available ready for use in biological assays, with several surface treatments—biotinylated, conjugated with strepavidin, or conjugated to Protein A. Several spectral profiles are offered for each product.

Last, new techniques of in-vivo labeling allow the use not only of naturally fluorescent proteins, but also of quantum dots and organic dyes (cf. Miyawaki et al., reference above) to study parameters of live cells. One example of a novel technique for labeling proteins with small organic fluorophores within live cells uses bi-arsenic fluorophore labeling of proteins that have been genetically altered to contain tetra-cysteine motifs (Griffin et al., *specific covalent labeling of recombinant protein molecules inside live cells*", Science 281, 269-272 (1998)). The protein to be labeled is genetically fused to a short peptide containing a CCXXCC motif The fluorescent label, FlAsH, is a derivative of fluorescein that contains two arsenoxide groups. The FlAsH label is membrane-permeant and non-fluorescent, acquiring fluorescence only on binding to the CCXXCC motif.

There are numerous suppliers, catalogs and on-line resources that help in selection of fluorescent probes, FRET pairs, and attachment reagents. Some well known suppliers include Molecular Probes (now Life Technologies), Bio-Rad Corporation and Pierce.

Numerous other methods exist for fluorescent labeling or dyeing a protein for fluorescent applications, as explained, for example in Allan, V. J. (ed), *Protein Localization by Fluorescence Microscopy, A Practical Approach*, Oxford University Press, herein incorporated by reference.

Cell-Free Translation Systems

Cell free translation systems are well known. Recently a synthetic system, built entirely from purified recombinant factors, and that has a high protein synthesis yield, was described (Shimizu et al., *Cell-free translation reconstituted with purified components*. Nat. Biotechnol. 2001 August; 19 (8):751-5). Kits and detailed instructions can be obtained from vendors such as Promega (Madison, Wis.). These systems are used for several applications, such as ORF validation and functional analysis of gene products. The systems contain ribosome-rich media with the required tRNAs and amino acids, and little or no mRNA. When mRNA is introduced, the ribosomes begin translation and proteins are produced. Often the proteins are produced radiolabeled. This enables the researcher to verify that the required proteins were in fact produced. The optional, exemplary system disclosed here is easier to assemble in-vitro than in-vivo, since labeling techniques are more readily available and easier to implement.

Translation of in-vitro transcribed mRNAs: In-vitro translation can be performed using kits such as the nuclease-treated rabbit reticulocyte lysate available from Promega, (Madison, Wis.). Before in-vitro translation, cellular mRNAs are heated at 67° C. for 10 min to unfold secondary structures that would eventually affect the efficiency of mRNA translation. Reactions are then assembled as recommended by the supplier in the presence of 20 mCi of [$35^S$]methionine (ICN Biochemicals). Protein synthesis occurs during incubation at 30° C. Customarily, the resulting proteins are purified and analyzed by radiolabeling. The procedure requires centrifugation, rinsing and immune-precipitation followed by separation on SDS-polyacrylamide gels. Following electrophoresis, gels are exposed to film or Phosphor B1 screens, and the bands corresponding to the synthesized protein verified. For PSM applications, radiolabeling of protein products may optionally be performed but is not required.

With the present invention, cell-free translation systems could optionally produce one protein or many proteins, and their identification and production rates could be measured, controlled, and optimized in real time. This can lead to new protein production methods that are easier to control than the customary methods of bio-production in reactors with bacteria, yeast or CHO-cells, for example. Since the in-vitro translation system is fully controllable, and since it also allows co- and post-translational modifications, this method is an attractive alternative to current technologies.

When single molecule detection is required in in-vitro translation systems, the molecules need to be immobilized. There are several approaches to immobilization of biomolecules. Biomolecules can be attached specifically or non-specifically, and in either case, either ribosomes or mRNA templates can be immobilized.

For non-specific immobilization, DNA or RNA can be attached to a charged surface such as an aminopropylsilane-coated surface via electrostatic interaction, as described in 8. Ha, T. et al., (1996) Proc. Natl. Acad. Sci. USA 93, 6264-6268. Even though this method avoids DNA aggregation and works in water, this immobilization method may interfere with the properties or activity of the ribosome.

Another nonspecific immobilization method successfully used for single-molecule fluorescence study is trapping molecules inside polyacrylamide pores (Dickson, R. M., et al., (1996) *Science* 274, 966-969) or agarose gel (Lu, H. P., et al., (1998) *Science* 282, 1877-1882, Dickson, R. M., et al., (1997) *Nature* 388, 355-358). While gel immobilization has the merit of not requiring any special modification of the biomolecule, it has some disadvantages. First, the concentration of other small molecules such as enzyme substrates and ions is difficult to change in a short time. Sudden changes in the buffer conditions are necessary for a certain type of single-molecule studies. Second, because of limited molecular diffusion, it is not easy to study interactions between macromolecules in gel.

Specific immobilization requires a well-defined modification of the biological molecule. For instance, a biotin or a digoxigenin can be attached to an mRNA, rRNA or ribosomal protein, to immobilize them to streptavidin- or antidigoxigenin-coated surfaces respectively. Alternatively, histidine tags that are typically introduced to help the purification of recombination proteins can be used to immobilize a ribosomal protein on a Ni-NTA-coated surface. A detailed procedure for preparing a mini-flow cell to immobilize biotinylated nucleic acids is described in Ha, T., Methods 25, 78-86 (2001).

A surface can be densely coated by polyethylene glycol (PEG). PEG is known to reject protein adsorption to a surface if it forms a dense coating. Bifunctional PEG can be used immobilize nucleic acids specifically to a surface while rejecting protein adsorption. mRNA can be optionally immobilized on a polyethylene glycol (PEG) coated surface with biotin-streptavidin linker, and the ribosomes allowed to process the immobilized mRNA. The mRNA preferably features 3'-end biotin labeling. Since protein synthesis may not end normally because of the linked 3' end, it is advisable to ensure that the template mRNA continues for at least 20 codons beyond the stop codon. In another approach, a ribosomal protein can be labeled with biotin and immobilized on a fused glass slide. The other ribosomal components can then be reconstituted around the immobilized protein.

Ribosomal complexes can also be bound to a mica surface, which is transparent and flat on a molecular size scale. Ribosomes, either labeled or unlabeled, undergo binding to mica in a few seconds, allowing the detection of single fluorescence images in aqueous buffer. A large excess of ribosomes and a short incubation period are employed for single molecule detection. The mica-bound ribosomes retain their activities, as shown in Sytnik et al., J. Mol. Biol. (1999), 285, 49-54, where detailed protocols are provided. Preparation of the mica cells and adsorption of ribosomes to these cells is also described in Vanzi et al., *Protein synthesis by single ribosomes*, RNA (2003), 9:1174-1179.

DETAILED DESCRIPTION OF SEVERAL EMBODIMENTS

The present invention provides an apparatus and method for monitoring protein synthesis in a protein synthesis system, by using a marker for protein synthesis, which optionally comprises at least one photo-active component, and preferably causes electromagnetic radiation to be emitted. The method provides single molecule fluorescence analysis of a protein synthesis system, for example of a single ribosome, or may alternatively provide single molecule fluoresence analysis of a plurality of ribosomes in parallel.

According to the principles of the invention, the emitted electromagnetic radiation is detected and analyzed to monitor protein synthesis. The present invention may optionally be performed qualitatively, but is preferably performed quantitatively. As used herein, "monitoring" may also optionally include at least the initial detection of a protein synthetic act or process, such as an interaction between a tRNA and a ribosome for example, preferably in real time. Optionally and preferably, monitoring includes identification of the tRNA or tRNA species, amino acid or amino acid species, codon or codon species that are being processed. Preferably, monitoring includes detecting a plurality of such synthetic acts, such as a plurality of interactions between a ribosome and a plurality of different tRNA molecules. Monitoring optionally and more preferably includes identifying the protein being synthesized. The protein synthesis system optionally and more preferably includes a single ribosome or a plurality of ribosomes, with tRNA or tRNA species and/or other protein synthetic components as required, optionally in vivo or in vitro.

The present invention enables detection of which tRNA is currently being processed by a ribosome, which mRNA codon is being read, or which amino acid is currently being added to the nascent protein. The procedure can optionally be performed simultaneously for hundreds of single ribosomes, optionally in vitro or in vivo and so provide, for the first time in biology, a tool for dynamic monitoring of protein synthesis.

Optionally, as described in greater detail below, the present invention may be implemented with a cell that is stably engineered, for example through genetic engineering, to form a stable cell culture and/or cell line. Alternatively or additionally, the cell may optionally be transiently altered or engineered; optionally a combination of these techniques may be employed, for a single cell or a plurality of cells.

Optionally and preferably, the present invention is used for performing a screening assay by detecting or monitoring the protein synthetic act. Optionally, the screening assay is for detecting a pathological condition in a subject, such as cancer. The present invention may also optionally be used for pathway elucidation by detecting or monitoring the protein synthetic act. The present invention may also optionally be used for cell state analysis by detecting or monitoring protein synthetic act, for example by identifying the synthesis of proteins related to apoptosis, heat shock, DNA damage repair, budding, or any other cell state.

The present invention provides many advantages, including but are not limited to, real-time, optionally in-vitro and in-vivo, monitoring of protein synthesis, unprecedented sensitivity, highly accurate quantitation, the ability to monitor cellular events through protein synthesis, the ability to complement other methods such as protein tagging for monitoring protein localization and degradation, elucidation of protein pathways and interactions, and support of protein function analysis. The present invention can also be used to monitor protein production and assist in process optimization and control.

The present invention also has the advantage of providing an assay for protein synthesis which is optionally cell based. Cell based assays have many advantages over receptor binding assays. Cells offer better representations of a disease. By screening against disease pathways in whole cells, no prior assumptions are made about what makes a good target. However, cell based screening assays, as for other screening assays, provide only a binary, or yes/no answer, for a given compound. This type of answer limits the scope of information obtainable, and causes the entire cascade of events following administration of a test compound under analysis to remain hidden from the researcher. These limitations are in strong contrast to the PSM assay method of the present invention that is disclosed herein, where upon administration of a test compound, no special preparations are required (besides optionally using cells that were prepared for PSM), no assumptions are required, and protein synthesis processes can be followed to gain a more complete understanding of the cell's response to the chemical or environmental stimulus that was applied.

The present invention has a number of other, additional advantages over background art techniques. For example, the present invention provides comprehensive information about protein production in the cell, showing precisely how, when, in what order and in what amounts does the cell respond to the compound following administration. The target itself can be seen in the context of other proteins that are co-synthesized with it, before it, or after it; connections with other proteins can be identified. Similarly, the compound can be seen in the context of other compounds that elicit a similar response, allowing SAR and QSAR analyses to be performed.

Furthermore, apart from the hitherto unavailable information that the present invention provides, the technique holds the important promise of both widening and shortening the drug development process by early removal of compounds from the pipeline, by providing a much larger amount of information about a candidate drug much earlier in the process, and by allowing more compounds and targets to enter this process. Thus, the present invention has the potential to produce many more drugs in shorter time and with smaller expenditure.

Another important application of the present invention is as a tool for process optimization, process control and quality control of protein production, either in bio-reactors using bacteria or cell culture, or else in cell free translation systems. In these situations, the present invention can provide indispensable information about the amounts of the target protein being produced, as well as on the precise structure of the proteome backdrop to this manufacturing, ensuring that the desired protein is produced in precisely the required environment. This level of control, unavailable today, can create a revolution in the way proteins and protein drugs are produced and certified. This can lead to new protein production methods that are easier to control than current ones.

The present invention enables analysis of the effects of drug candidate compounds on target proteins, such as by causing their up- or down-regulation. In addition, a sequence of events can be determined, for example, protein pathways can be identified by interpretation of the changing translation patterns, noting which proteins are just beginning to be translated and which are ceasing to be translated. Moreover, rare, hydrophobic, and heavy proteins can be identified at the same efficiency as any other protein; cell-free translation systems can be monitored in real-time and protein production processes can be monitored and optimized. These procedures may optionally be performed in seconds rather than days, with a single type of engineered cell (from a given cell-line) that is as near to a natural, non-engineered cell as possible, and with the benefit that performing a PSM assay with this cell-line may provide a huge amount of information on the compound being tested. These capabilities are in strong contrast with the multitude of specialty, heavily engineered cell types that are required today. Indeed, the present invention may optionally provide a "universal assay" for drug discovery and development on the one hand, as well as an indispensable tool for basic and applied scientific biological and pharmaceutical research and production.

Illustrative, optional methods for monitoring of protein synthesis are now described in detail below. The method will be described in several variants and several applications by way of an example, and it should be recognized that the illustrated embodiments should not be taken as a limitation on the scope of the disclosure. The following sections describe various aspects and details of the new invention.

Section I

Illustrative Embodiments of the Present Invention

DD1 Strategies for Synthesis Monitoring (R-T, R-A, R-R, and Multicolor)

Overview

An optional, exemplary but preferred method of the present invention is now described for synthesis monitoring. The ribosome of a live bacterium, cell, or an in-vitro translation mechanism is tagged with a donor fluorophore. One or more types of acceptor fluorophores are placed on some of the tRNAs and/or on some of the amino acids and/or on another part of the ribosome. As the ribosome goes through the elongation cycle, a FRET signal is generated when labeled tRNAs, labeled amino acids or appropriate codons are processed. Since only some and not all species of tRNA or amino acids or codons are designed to generate a signal, the resulting signal is a characteristic of the protein being translated, and so, with an appropriate method of signal analysis, this protein may optionally be identified.

One exemplary flow of operation is now described. An optical apparatus monitors a marked protein synthesis system (a system featuring at least one marker according to the present invention), optionally by directing electromagnetic radiation of the required wavelength and energy onto the marked system, thereby exciting the donor fluorophores. The acceptor fluorophores on the tRNAs and/or amino acids and/or on the ribosome, whether engineered or natural, respond to this energy with the FRET effect whenever donor and acceptor are in sufficient proximity, indicating the progress of the elongation cycle of said synthesis system. Fluorescence radiation emitted from the acceptor fluorophores is detected by the optical apparatus and the event is recorded by a computerized analysis unit. Since only some of the elongation cycles but not all of them generate a signal, the resulting sequence of detection events is a characteristic of the protein being synthesized. In computer science terminology this signal sequence may optionally be described as a bit stream with zeroes and ones. The stream contains some uncertainty as to the number of bits in each field, as well as other elements of uncertainty. The signal is subsequently used to interrogate a database of signals computed from a relevant database of protein sequences. The method disclosed herein describes how to use this signal to identify the protein that is most likely to have produced the signal.

The method is preferably able to consider the precise nature of the uncertainty in the detected signal sequence, in order to provide a scoring function that is able to compute the measure of likelihood, for each protein in the database, that this protein species is the one whose synthesis produced the signal sequence that was detected.

There are a number of optional basic strategies for PSM labeling (for adding a marker to the protein synthesis system, optionally through covalent or non-covalent binding, for example to a tRNA and/or ribosome or portion thereof), a few examples of which are described below.

Ribosome-tRNA (R-T) Labeling

Figure 4:
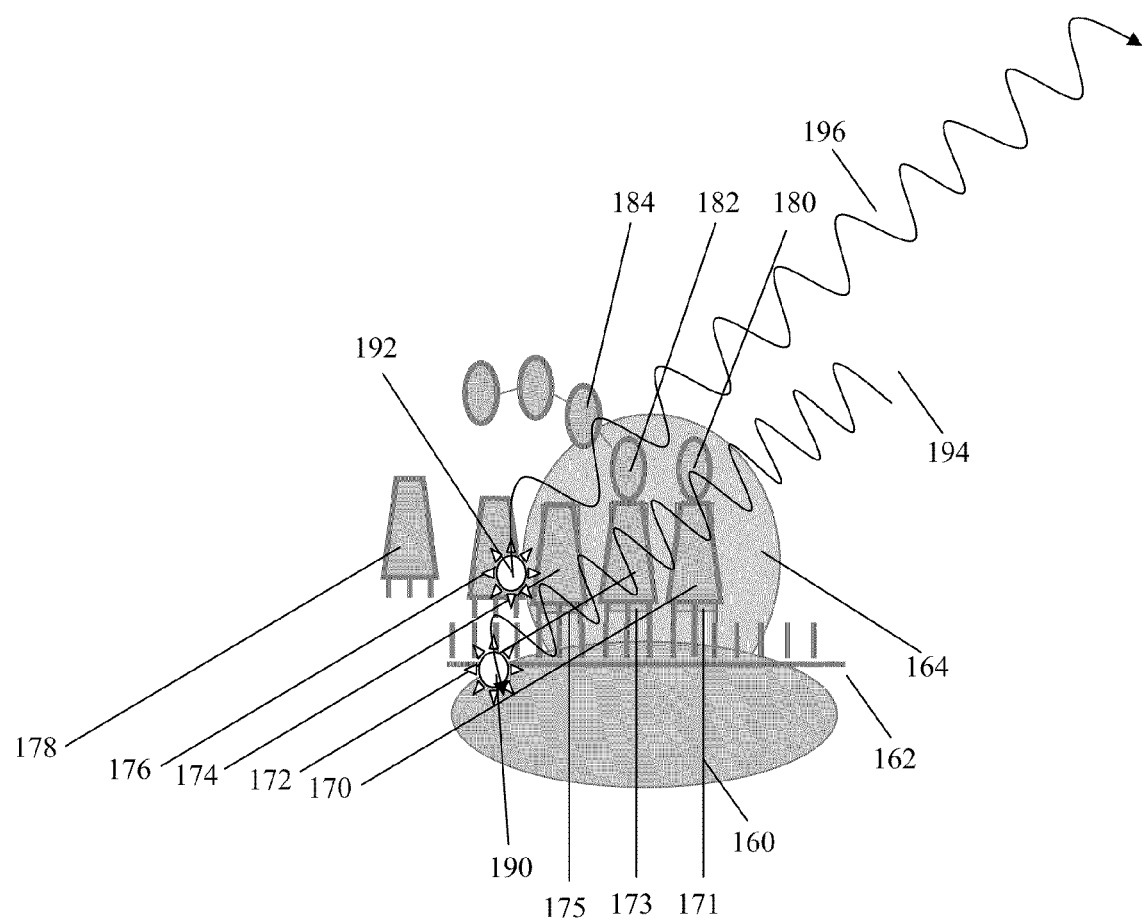
FIG. 4 describes the embodiment of the R-T tag strategy.

This optional, exemplary labeling strategy calls for a donor label on the ribosome and an acceptor label on tRNA, or vice versa. R-T tagging or labeling may optionally include a fluorescent labeling method in which the ribosome and tRNA form a FRET pair and/or other type of donor/acceptor pair and/or fluorescent/quencher pair. FIG. 4 shows a specific example of this strategy.

In this optional embodiment of the present invention, R-T tagging involves placing a donor on the ribosome and an acceptor on some of the tRNAs. Methods of tagging tRNAs and ribosomes are discussed below. The tag can be placed either near the A, the P, or the E site. In one preferable embodiment a ribosomal locus near the E site is tagged. This ensures that the tRNA is identified after the proofreading stage. In one preferable embodiment ribosomal proteins are tagged. Several ribosomal proteins are known to be near the E site, such as ribosomal proteins L1, S1 and S21. Experiments have shown that these proteins can be efficiently tagged while retaining ribosome functionality. Such experiments are described, for example, in Mascarenhas et al., *Specific polar localization of ribosomes in Bacillus subtilis depends on active transcription*. EMBO Rep. 2001 August; 2 (8):685-9, in which ribosomal protein L1 was labeled with blue fluorescent protein (BFP) and proven to retain its functionality; and in Odom et al., "*Relaxation time, intethiol distance, and mechanism of action of ribosomal protein S1*", Archiv. Biochem. Biophys. 1984, 230 (1) 178-193, in which ribosomal protein S1 was labeled through its two cysteines.

FIG. 4 shows one exemplary embodiment of the R-T tagging strategy. Ribosome large subunit 160 and small subunit 164 are attached to an mRNA 162 being processed. tRNA 170 (with amino acid 180) is in A site 171, tRNA 172 (with amino acid 182) in P site 173, tRNA 174 in E site 175. tRNA 176 has just been ejected out of the E site and tRNA 178 is already free of the ribosomal-mRNA complex. The growing polypeptide chain 184 is also shown. Donor fluorophore 190 is located preferably and optionally on ribosomal protein L1, which is attached to large ribosome subunit 160, just outside the mRNA exit channel (not shown), in proximity to the E site. tRNA 176 in this Figure is labeled with a fluorescent label 192 and therefore is in close proximity to the donor fluorophore 190. The donor fluorophore emission spectrum overlaps the excitation spectrum of acceptor fluorophore 192. Radiation energy 194 is made to impinge on donor fluorophore 190 and excite it, causing part of the energy to transfer to acceptor fluorophore 192, exciting it and causing emission of FRET signal 196 of a lower energy and therefore higher wavelength. When tRNA 192 is not of a tRNA species that has been labeled, a FRET signal is not emitted. Thus, as the ribosome processes the mRNA, an on-off signal is detected by the system that corresponds to the tRNA labeling scheme being used and therefore characterizing the protein being synthesized, allowing the identification of the protein being synthesized.

R-A Labeling

R-A tagging or labeling is another optional embodiment of the present invention, in which the ribosome and an amino acid form a FRET pair and/or other donor/acceptor pair and/or fluorescent/quencher pair. In another exemplary, optional embodiment of the present invention, the donor tag is placed near the peptide exit channel, and so is able to excite the acceptor fluorophores on the amino acids, either natural or engineered. In this embodiment, the detected FRET signal correlates with the amino acid sequence of the protein being synthesized; however, the proteins include labeled amino acids and are therefore no longer completely natural, a fact which may influence the functioning of the cellular mechanism.

Figure 5:
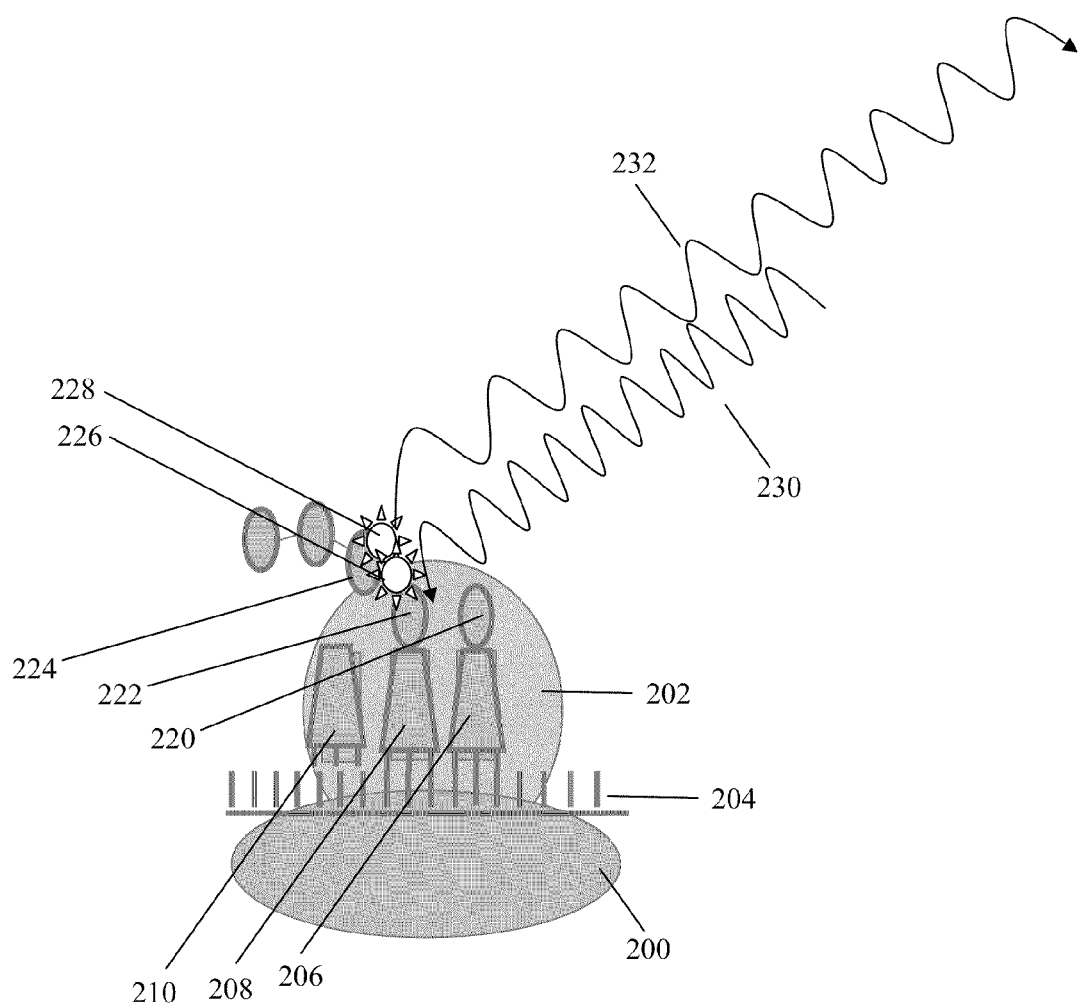
FIG. 5 describes the embodiment of the R-A tag strategy.

In FIG. 5 an example of this type of embodiment is depicted. Ribosome small subunit 200 and large subunit 202 are attached to mRNA 204 being processed. tRNA 206 is docked in the A site and carries amino acid 220. tRNA 208 is docked in P site and carries amino acid 222. tRNA 210 is docked in the E site and its amino acid has already been removed. Donor fluorophore 226 is attached to the ribosome in a location near the exit location of the peptide channel (not shown). Donor fluorophore 226 is illuminated with electromagnetic radiation 230 of a frequency compatible with its excitation frequency. Emission frequency of donor fluorophore 226 overlaps the excitation frequency of acceptor fluorophore 228. Acceptor fluorophore can be either natural, as in the amino acids tyrosine, tryptophan and phenylalanine for example, or else can be artificially labeled as explained below. In any case, if the amino acid 224 is appropriately labeled with acceptor fluorophore 228, then a FRET 232 signal is generated when acceptor fluorophore 228 passes sufficiently close to donor fluorophore 226. When unlabeled amino acids are in this position, a FRET signal is not generated. Thus, as the ribosome synthesizes the protein, an on-off signal is generated that is characteristic of the protein being synthesized, allowing it to be identified.

R-R Labeling

R-R tagging or labeling is another optional embodiment of the present invention in which two locations on the ribosome, optionally covalently bound or non-covalently associated moieties, form a FRET pair and/or other donor/acceptor pair, and/or fluorescent/quencher pair.

In another exemplary, optional embodiment of the present invention, both donor and acceptor tags are attached to the ribosome; the combination of both tags may optionally be described as a marker for the present invention. One tag ("base") is preferably located on a fixed part of the ribosome, which makes it static. The other ("lever") is preferably an appendage engineered to be attached to the ribosome, covalently or non-covalently, and is capable of moving in one prescribed direction—towards or away from the location of the mRNA as it exits the ribosome. In one optional embodiment, the lever mimics a tRNA molecule in order to recognize exiting mRNA codons. The lever is preferably constructed to bind weakly to a specific nucleotide triplet or pair, as in the case of codon-anticodon recognition rules. If, for example, the lever is designed to recognize the nucleotide pair GC, whenever the mRNA sequence contains a GC in the appropriate position, the lever goes "down" and binds to GC, preferably causing a fluorescent signal to be generated or quenched (or optionally a combination, if a plurality of fluorescent moieties is present). For other pairs, the lever stays "up" and this signal is not generated or quenched (or the combination is not generated). The FRET or other type of signal thus marks the advance of the mRNA with a bimodal response. This embodiment has the important benefits of leaving the translation mechanism almost entirely natural—tRNAs and amino acids are completely natural, only an external part of the ribosome has been tampered with.

Figure 6A:
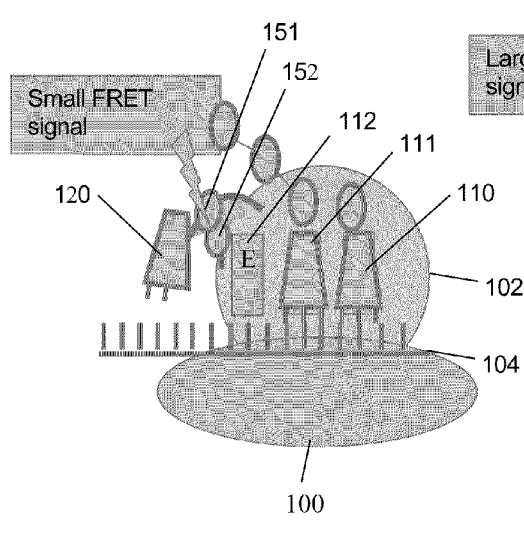
FIGS. 6A-6D describe the embodiment of the R-R tag strategy.

Illustrative diagrams of this exemplary embodiment are shown in FIGS. 6A-6D. The lever is a preferably a modified tRNA molecule, with a "codon loop" and a relatively long and rigid arm, connected to a "hinge". This can be engineered to stem out of a single strand rRNA loop. The ribosomal RNA has numerous stretches of single strands, extending from a few bases to a few dozen bases. These single strand loops are convenient for placing an extension that has the required biochemical and physical characteristics. The pseudo-anticodon part of the lever is constructed to bind weakly to a specific nucleotide pair, such as GC in the example. In FIG. 6A the mechanism is shown in the "non-recognition" configuration. 100 and 102 are the small and large ribosome subunits, 110, 111 and 112 are the A, P and E sites respectively. Only the A site 110 and P site 111 are occupied in this diagram.

A tRNA-like lever 120, connected in this illustrative example to large ribosomal subunit 102, does not bind (binding taken here to signify at least the creation of Watson-Crick pairs) to the nucleotides on mRNA 104, which passes between large subunit 102 and small subunit 100. This lack of binding is because the corresponding bases on the mRNA 104 and pseudo-anticodon 120 are not complementary pairs (in the Watson-Crick sense). Therefore lever 120 stays relatively far removed from an acceptor fluorophore 152. Lever 120 carries a donor fluorophore 151, while the acceptor fluorophore 152 is attached at an appropriate location to the ribosome. When lever 120 remains in the "far" position, a small or null FRET signal is generated.

Figure 6B:
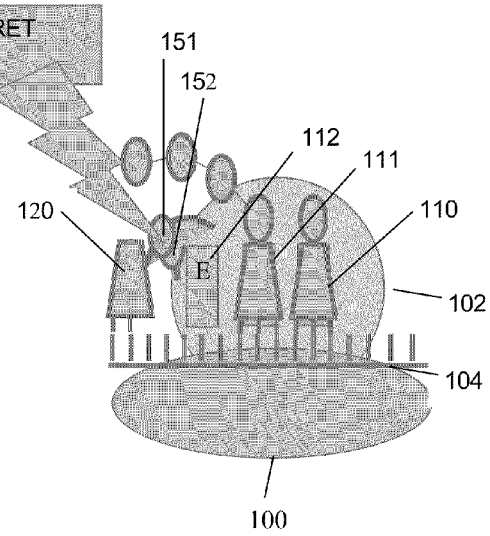

In FIG. 6B the mechanism is shown in a "recognition" configuration, where the pseudo-anticodon on tRNA-like lever 120 does match the nucleotides on mRNA 104, in the sense of Watson-Crick pairing. Therefore lever 120 moves relatively near to mRNA 104, causing donor fluorophore 151 and acceptor fluorophore 152 to come into close proximity and to emit a large FRET signal. The FRET signal thus marks the advance of the mRNA with a bimodal response—for example, detection of a large signal versus small signal. Thus, as the ribosome processes the mRNA, an on-off signal is generated that is characteristic of the protein being synthesized, allowing it to be identified.

Figure 6C:
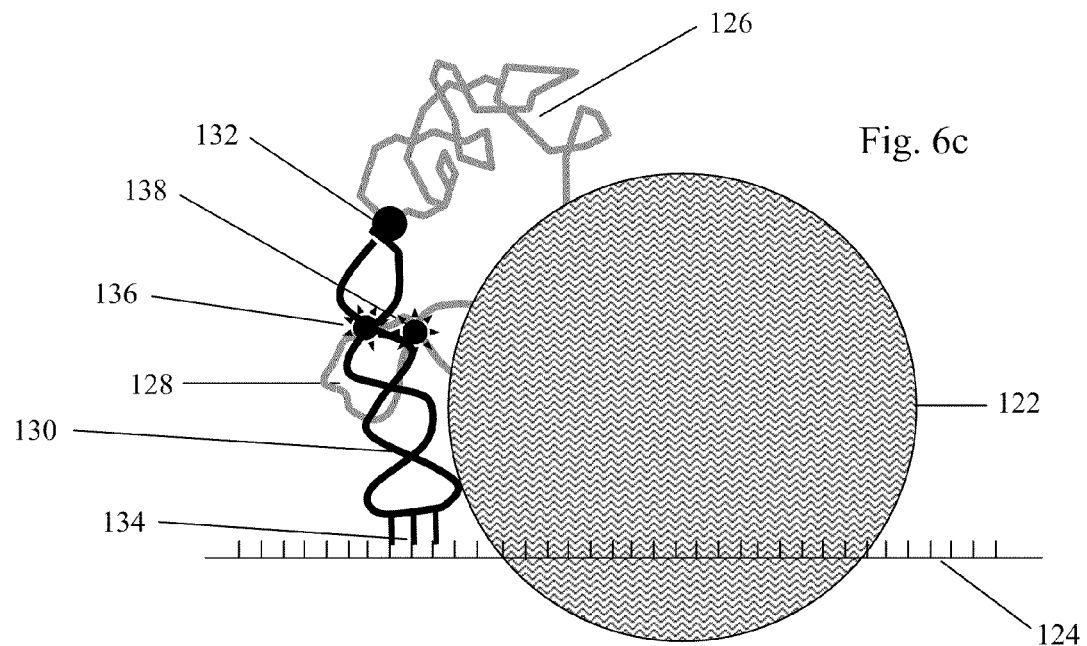
Figure 6D:
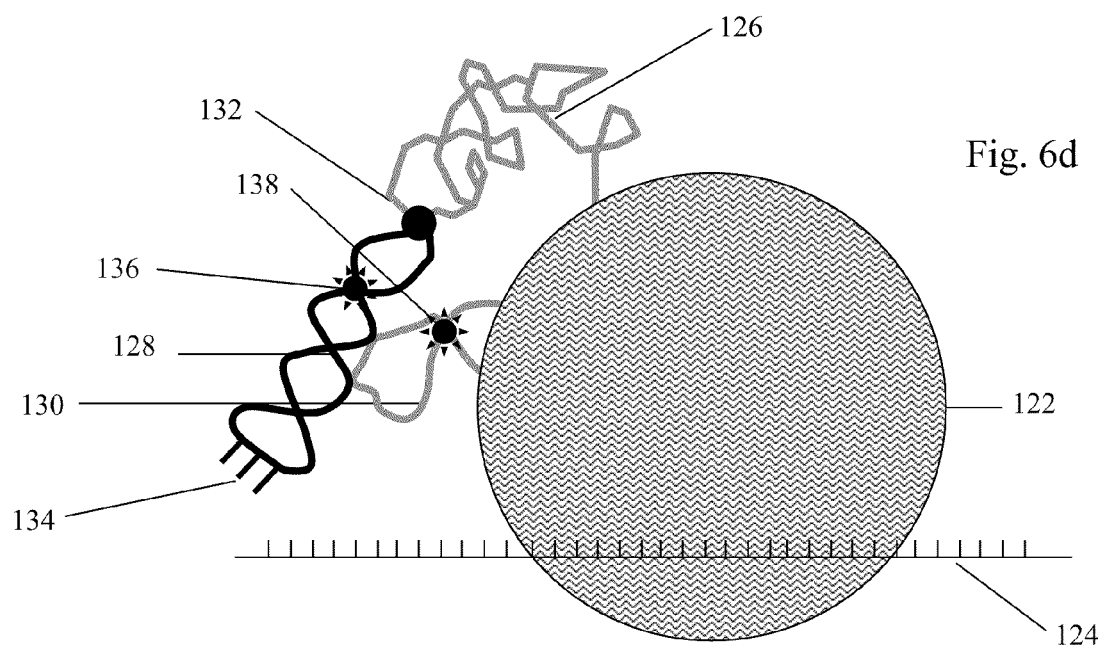

In FIGS. 6C and 6D this mechanism is shown in greater detail. Ribosome 122 has protruding chains 126 and 128 (shown in grey). The mRNA being translated 124 is shown with nucleotides spaced on it. Static label 138 is attached to a location on one of these protruding chains. Artificially engineered RNA chain ("lever") 130 (shown in black) is attached at point 132 to form a movable hinge. The main part of RNA chain 130 has a helical structure and therefore is physically rigid. The part farthest away from hinge 132 has an anticodon nucleotide sequence 134. On the chain 130 a fluorescent label 136 is attached. FIG. 6C shows the lever in recognition configuration, where the anticodon 134 recognizes a codon on mRNA 124. In this case the lever assumes a position where the fluorescent labels 136 and 138 are in close proximity, allowing a FRET signal to be emitted. In FIG. 6D, the lever is in a non-recognition configuration, where the anticodon 134 does not recognize the codon on mRNA 124. In this case the lever assumes a position where the fluorescent labels 136 and 138 are relatively far apart, and a FRET signal is not emitted, or else a much smaller FRET signal is emitted than in a recognition configuration.

Multicolor Labeling

In the preceding examples it was assumed that the labeling was of the "on/off" kind, that is, one type of label was either used or not used. Optionally and preferably, some preferred embodiments of the present invention use more than one type of label. For example, in the R-T labeling strategy, if each type of tRNA could be labeled with its own specific color, the system would have been simpler since database interrogation would have become a matter of a trivial search procedure and, indeed, de-novo protein sequencing would have been possible in-vivo. Again, such a label optionally forms part or all of the marker according to the present invention. Even if this optional scheme is difficult to achieve, labeling the tRNA species with more than one color increases the amount of information available. For example, if 10 tRNA species are labeled with two label types (5 with each) rather than one, an increase of $$\binom{10}{5} = 252$$

fold in the amount of information is obtained. In fact, with some of the labeling methods this becomes possible. For example, when acceptor fluorophore is a quantum dot, then its excitation spectrum is very wide (see above), while the emission spectra is very narrow and can be distinguished easily. In such a case one donor fluorophore can excite several acceptors, resulting in additional sequence information.

Additional PSM Strategies

In one preferred embodiment, a plurality or even all tRNAs, amino acids or codons are labeled, and not just a part of them. When this is done with one type of label, it is not possible to identify the protein being synthesized. However, this technique is useful for measuring synthesis rates, on/off FRET times, and for system calibration. When the labeling is done with several types of fluorophores, two, three or more, a large increase in the amount of information and confidence of the resulting identification is obtained when all items are labeled.

In one preferred embodiment, a quenching strategy is used instead of FRET, as noted previously. In this approach, instead of a fluorescent donor and acceptor, there is a fluorescent donor and an acceptor quencher that captures the donor energy without emission. In this strategy, donor fluorescence is detected as long as the quencher is not sufficiently near to the donor. In PSM, this would generate a signal of donor fluorescence intermitted by periods of quenching.

In another preferred embodiment, a combination of methods can be used. For example, some tRNAs may be labeled for R-T tagging strategy, as well as one or more amino acids that are labeled for R-A strategy. The ribosome is labeled in a way that allows both methods to be used. Preferably, the amino acids are labeled with fluorescent labels that are distinct from tRNA labels. The signal analysis system accepts both signals and uses both in order to identify more confidently the protein being synthesized. It is obvious to anyone skilled in the art of single molecule detection and analysis that this is just one example of a wide variety of methods that can be derived from this particular example.

In one optional but preferred embodiment of the present invention, the natural fluorescence of tRNAs and/or amino acids is utilized. In another optional embodiment of the present invention, a fluorophore is attached to some tRNAs and/or amino acids. It is clear to anyone skilled in this art that the donor and acceptor configurations could be switched. It is also clear to anyone skilled in the art that the embodiments described above are not mutually exclusive and any combination thereof can be used, which is another optional embodiment of the present invention. For example, the natural fluorescence of some amino acids together with artificially labeled tRNA species can be used in a combination system.

DD2 Fluorescent Labeling of Ribosome, Proteins and tRNA Ribosome Labeling.

A large body of research details fluorescent labeling techniques of ribosomes; such labeling may optionally be used with the present invention as a marker or a portion thereof. These include in vitro and in vivo labeling, labeling with naturally fluorescent proteins and with organic dyes. Other published techniques that are relevant include labeling with semiconductor quantum dots. Labeling strategies included labeling ribosomal proteins such as ribosomal proteins L1, S1, S21 and others; In addition, 3' and 5' ends of 5S, 16S and 23S rRNA have been labeled (Robbins and Hardesty, *Comparison of ribosomal entry and acceptor transfer ribonucleic acid binding sites on Escherichia coli 70S. ribosomes. Fluorescence energy transfer measurements from Phe-tRNA$^{Phe}$ to the 3' end of 16S. ribonucleic acid*. Biochemistry. 1983 Nov. 22; 22 (24):5675-9).

For in vitro labeling, there are several strategies. Organic dyes can be used to label ribosomal proteins using standard protein labeling techniques. Suppliers of these dyes publish detailed protocols describing their use. General procedures label proteins through their amino groups (lysine). Other procedures target cysteines which are sometimes available for precisely located labeling. In this way, ribosomal proteins S1 and S8 were labeled by coumarin (Bakin et al., *Spatial organization of template polynucleotides on the ribosome determined by fluorescence methods*. J Mol. Biol. 1991 Sep. 20; 221 (2):441-53), and ribosomal proteins were tagged with fluorescein attached to a cysteine residue (Odom et al., *Movement of tRNA but not the nascent peptide during peptide bond formation on ribosomes*. Biochemistry. 1990 Dec. 4; 29 (48): 10734-44).

A novel labeling strategy uses quantum dots, which are commercially available pre-conjugated with biotin or streptavidin. In such cases, proteins can be labeled with biotin, so the streptavidin conjugated qdots (commercially available as Qdot™525/Qdot™ 565/Qdot™ 605/Qdot™ 655 streptavidin conjugated quantum dots, from Quantum Dot Corporation, Hayward, Ca, USA; the numbers relate to maximal emission wavelength, m) bind specifically to them. One useful method of generating a biotin-labeled protein involves creating a fusion protein between the protein of choice and biotin carboxyl carrier protein (BCCP). In the fusion protein, the original protein sequence is fused optionally to the last 87 (or 110) codons of the *E. coli* BCCP. When the fusion protein is translated, it has the biotin tag attached to it and binds specifically to streptavidin (cf. Surrey et al., *Proc. Natl. Acad. Sci. USA*, Vol. 95, pp. 4293-4298, April 1998). This method is also useful in-vivo, since both organic dyes and quantum dots can be engineered to be attached to streptavidin and have membrane permeable characteristics (see, for example, Miyawaki, et al., Nat Cell Biol. 2003 September; Suppl:S1-7. Review; and Akerman et al., PNAS, 99:12617-12621, 2002)

Another method that is useful for in-vivo labeling of ribosomal proteins is the well known strategy of fusing the protein of choice with a naturally fluorescent protein, such as green fluorescent protein, yellow/cyan/blue fluorescent proteins or any other naturally fluorescent protein. An example where L1 was labeled by fusing it with a naturally fluorescent protein is described in (Mascarenhas et al., *Specific polar localization of ribosomes in Bacillus subtilis depends on active transcription*. EMBO Rep. 2001 August; 2 (8):685-9). Yet another novel method of in-vivo labeling involves the rare sequence CCXXCC(C=cystein). The protein to be labeled is genetically fused to a short peptide containing a CCXXCC motif. The fluorescent label, FlAsH, a derivative of fluorescein that contains two arsenoxide groups, is membrane-permeant and non-fluorescent, acquiring fluorescence only on binding to the CCXXCC motif.

Numerous additional strategies for ribosome labeling were tested and others are clearly possible.

In particular embodiments, the density of labeled ribosomes in the system is less than about 10 labeled ribosomes per cubic micron, or less than about 5 labeled ribosomes per cubic micron, less than about 0.1 labeled ribosomes per cubic micron, or less than about 0.02 labeled ribosomes per cubic micron.

Such a density may be advantageous, for example by providing a distance of several pixels between a labeled ribosome and the nearest other labeled ribosome. This may facilitate determination of the signals emitted from a single ribosome, for example by minimizing or avoiding interference with signals emitted from other ribosomes.

tRNA Labeling

Labeling a tRNA molecule is sensitive, since the molecule is small, and since it interacts in intricate ways with the aminoacyl synthetases on the one hand and with the ribosomal machinery on the other. As a tRNA molecule docks onto (binds to) the ribosome-mRNA complex, it is bound with elongation factor EF-TU and a GTP molecule. Tagging should also be compatible with this complex. Further, tRNA tag should have a high binding rate, so that preferably above 90% of the labeled tRNA species is actually labeled.

Experiments have shown that tRNA molecules can be tagged while retaining their interaction with the aminoacyl synthetases as well as retaining their functionality with the ribosome. tRNAs have been tagged with fluorescein (Watson et al., *Macromolecular arrangement in the aminoacyl-tRNA. elongation factor Tu.GTP ternary complex. A fluorescence energy transfer study*, Biochemistry. 1995 Jun. 20; 34 (24): 7904-12; Plumbridge et al., *Characterisation of a new, fully active fluorescent derivative of E. coli tRNA Phe*. Nucleic Acids Res. 1980 Feb. 25; 8 (4):827-43), tetra methyl rhodamine (Jia et al., *Nonexponential kinetics of a single tRNAPhe molecule under physiological conditions*. Proc Natl Acad Sci USA. 1997 Jul. 22; 94 (15):7932-6), with the dye IAEDANS (5-((((2-iodoacetyl)amino)ethyl)amino)naphthalene-1-sulfonic acid (1,5-IAEDANS)) (Johnson et al., *Distance moved by transfer RNA during translocation from the A site to the P site on the ribosome*, J. Mol. Biol. (1982) 156, 113-140), with proflavine and ethidium bromide (Wintermeyer and Zachau, *Replacement of Y base, dihydrouracil, and 7-methylguanine in tRNA by artificial odd bases*. FEBS Lett. 1971 Nov. 1; 18 (2):214-218). Numerous other labeling strategies have been studied.

For the present invention, some optional but preferred embodiments include but are not limited to labeling the tRNA with small organic dyes attached to the "shoulder" region of the tRNA, such as in positions 8 and 47 of *E. Coli* tRNAs which have been often used for this purpose. Note that both the anticodon region and the amino acid carrying region are sensitive, both in charging and in discharging. The dyes with which most experience has been gained are FITC and TMR. Detailed protocols for tRNA labeling with these dyes are presented below.

In numerous published experiments *E. Coli* tRNA$^{Phe}$ has been labeled by attaching a small organic dye either to the 4-thiouridine at position 8, where the sulfur atom offers the required reactive handle, or to the X-base (3-(3-amino-3-carboxypropyl)uridine) at position 47, which has a primary reactive amine group coupled to the ribonucleic base by an aliphatic handle. Out of the 45 *E. Coli* tRNA species, 21 species have 4-thiouridine at position 8, and 7 have an X-base at position 47. Thus, ample opportunities for tRNA tagging strategies are possible. The list of *E. Coli* tRNAs with these special bases at positions 8 and 47 is shown in the table below. Also shown are the amino acids carried by the tRNA molecule and the 3 base anticodon sequences. The legend for the anticodon base symbols are as follows:

U-uridine, C-cytidine, A-adenosine, G-guanosine, T-thymine, H-unknown modified adenosine, 1-inosine, M-N4-acetylcytidine, Q-queuosine, 4-4-thiouridine, V-uridine 5-oxyacetic acid, X-3-(3-amino-3-carboxypropyl) uridine.

TABLE 1 tRNA amino acids

| Amino acid | Anticodon sequence | Base at position 8 | Amino acid | Anticodon sequence | Base at position 47 |
|---|---|---|---|---|---|
| Ala | VGC | 4 | Phe | GAA | X |
| Cys | GCA | 4 | Ile | GAU | X |
| Asp | QUC | 4 | Ile | }AU | X |
| Phe | GAA | 4 | Lys | SUU | X |
| Gly | CCC | 4 | Met | MAU | X |
| His | QUG | 4 | Arg | ICG | X |
| Ile | }AU | 4 | Val | GAC | X |
| Leu | HAA | 4 | | | |
| Met | MAU | 4 | | | |
| Asn | QUU | 4 | | | |
| Gln | CUG | 4 | | | |
| Gln | NUG | 4 | | | |
| Arg | ICG | 4 | | | |
| Ser | GCU | 4 | | | |
| Ser | GGA | 4 | | | |
| Ser | VGA | 4 | | | |
| Val | GAC | 4 | | | |
| Val | VAC | 4 | | | |
| Trp | CCA | 4 | | | |
| Ini | CAU | 4 | | | |
| Tyr | QUA | 4 | | | |

A complete database of tRNA sequences can be found at url www.uni-bayreuth.de/departments/biochemie/trna/. A database of known RNA modifications can be found at url medstat.med.utah.edu/RNAmods/, both of which are hereby incorporated by reference as if fully set forth herein.

Another preferred and optional embodiment relies on the natural fluorescence of some tRNA species. For example, E. Coli tRNA$^{Phe}$ contains the highly modified Y base (wybutosine) in position 37 (Langlois, R., Kim, S H and C R A Cantor. *A Comparison of the Fluorescence of the Y Base of Yeast tRNA Phe in Solution and in Crystals,* 1975, Biochemistry 14: 2554-2558; Huang, K. H. and Cantor, C. R., *Studies of 30 S Escherichia Coli Ribosome Reassembly Using Individual Proteins Labeled with an Environmentally Sensitive Fluorescent Probe,* 1975, J. Mol. Biology. 97, 423-441). In this particular embodiment, only the donor fluorophores need to be specially engineered onto the ribosome. However, this strategy has the disadvantage that the natural fluorescence of tRNA molecules is weaker than that of other specific labels.

AA Labeling

There are three general approaches for fluorescent labeling of amino acids. The first is to rely on the natural fluorescence of tryptophan, tyrosine and phenylalanine Tryptophan and tyrosine are highly fluorescent and can be used without modifications. Phenylalanine is slightly less so. The fluorescence properties of these amino acids are summarized in the table below.

TABLE 2 fluorescent properties of some amino acids

| amino acid | Lifetime (Nanoseconds) | Excitation | | Emission | |
|---|---|---|---|---|---|
| | | Wavelength | Molar absorptivity | Wavelength | Quantum yield |
| Tryptophan | 2.6 | 280 | 5,600 | 348 | 0.20 |
| Tyrosine | 3.6 | 274 | 1,400 | 303 | 0.14 |
| Phenylalanine | 6.4 | 257 | 200 | 282 | 0.04 |

The use of naturally fluorescent biomolecules is attractive as it requires less intervention and produces an engineered cell that is similar to a wild-type cell. The disadvantages are that the natural fluorescence is not as high as in naturally fluorescent proteins or organic dyes, and the excitation and emission peaks are fixed and cannot be changed. For the present invention, the fact that the excitation is in the UV region makes them more suitable as donors.

The second approach is using prelabled amino acids. Various alternatives exist for fluorescent labeling of amino acids. One example is The FluoroTect™ Green$_{Lys}$ in-vitro Translation Labeling System, available from Promega (Italy), which allows the fluorescent labeling of in-vitro translation products through the use of a modified charged lysine transfer RNA labeled with the fluorophore BODIPY®-FL. Using this system, fluorescently labeled lysine residues are incorporated into nascent proteins during translation.

The third alternative makes use of unnatural amino acids. These are incorporated into a protein by clever use of site-specific, unnatural amino acid mutagenesis, combined with use of the amber suppressor tRNA (Cornish et al., "Site specific incorporation of biophysical probes into proteins", Proc. Natl. Acad. Sci. USA, Bol. 91 2910-2914, 1994). In this method, a highly fluorescent unnatural amino acid (such as 7-azatyptophan) is charged onto an amber suppressor tRNA. In parallel, the gene of interest is mutated to include one or more amber codons in predetermined sites. This is loaded into an in-vivo or in-vitro translation system, and the protein synthesis system incorporates the unnatural amino acid wherever the amber codon is present in the mRNA sequence. This method suffers from several drawbacks, including the inability of recharging the suppressor tRNA and the need for interfering with the original protein sequence. However, it is useful for verifying the proper functionality of a PSM system, both in-vitro and in-vivo, as disclosed in detail below.

DD3 Optical Apparatus, Data Acquisition, Signal Generation and Analysis Scanning Versus Wide-Field Microscopy There are two general classes of fluorescence microscopic tools for single-molecule fluorescence studies, either of which may optionally be used with the present invention. The first class involves point detection with detectors that have single elements (photomultiplier tube (PMT) or silicon avalanche photodiode (APD)) used in combination with a confocal scanning optical microscope (CSOM) or near-field scanning optical microscope. The second class uses wide-field microscopy with two-dimensional detectors such as a CCD camera. One advantage of wide-field microscopy is that hundreds of single-molecules can be detected simultaneously, effectively performing hundreds of single-molecule experiments in parallel. This is especially useful for irreversible reactions or for very rare biological events. However, because an arrayed detector has to be used, the time resolution and the sensitivity are not as good as those of point detection cases.

Wide-field microscopy can be done either through epi-illumination or through prism type evanescent field excitation. In epi-illumination, the excitation light is sent through the epi-illumination port of a conventional fluorescence microscope. Unlike in CSOM, autofluorescence generated from the microscope optics and sample cannot be removed, resulting in an inferior signal/noise ratio. In contrast, evanescent field excitation does not permit excitation light to propagate toward the detector and hence can reduce the autofluorescence to an undetectable level. Such an evanescent field excitation is generated by total internal reflection of the excitation light at the glass—water interface; therefore, we call this microscope a total internal reflection microscope (TIRM).

Confocal Microscopy

Confocal microscopy allows the excitation and measurement of signals from a localized region with volume of less than $10^{-15}$ Liter. With appropriately labeled proteins there is a low chance of finding more than one tagged molecule in this volume. Confocal microscopes can be equipped with scanning laser illumination. The laser scans the focal plane a spot at a time, allowing images to be formed. The resulting instrument is called confocal scanning optical microscope (CSOM). In CSOM, laser excitation light is focused to a diffraction-limited spot using a high-numerical-aperture (NA) objective and the fluorescence coming from a single-molecule under the spot is collected using the same objective. A pinhole is used to block the out-of-focus autofluorescence signal to achieve single-molecule sensitivity. Unlike a commercial CSOM that raster-scans the laser beam for high-speed imaging, single-molecule CSOM typically scans the sample because the imaging speed is limited by the photon counts rather than by scanning speed. Two detectors are needed to detect donor and acceptor emissions simultaneously after their separation using a dichroic beam splitter. Computer-controlled data acquisition allows the accumulation of a large quantity of single molecule data by identifying individual molecules on the surface and taking the time records of single-molecule fluorescence signals.

Total Internal Reflection Fluorescent Microscopy (TIR-FM)

TIR-FM is a widely used technique for single molecule detection both in-vitro and in-vivo. TIR-FM, originally developed to observe the interface between two media with different diffractive indices, uses an electromagnetic field called the 'evanescent field' to excite fluorophores. As the evanescent field diminishes exponentially with distance from the interface, the excitation depth in TIR-FM is limited to a very narrow range—typically one hundred to several hundreds of nanometers. Using such a narrow excitation depth is an effective way to overcome the background noise problem.

Figure 7:
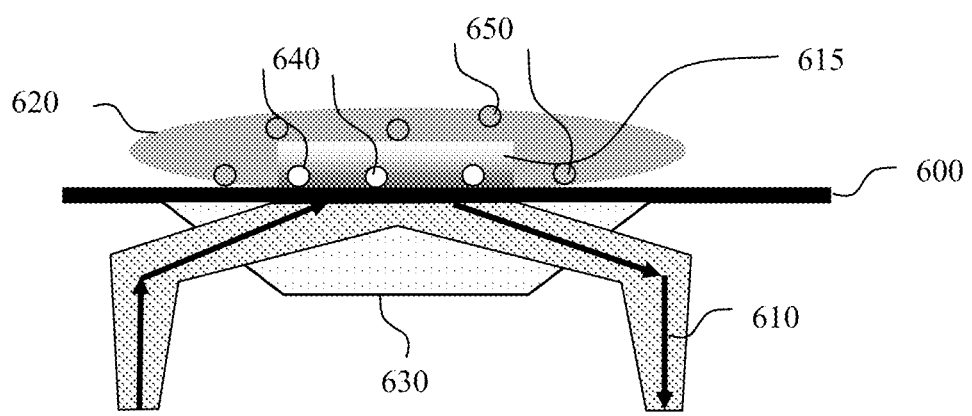
FIG. 7 shows the principle of total internal reflection (TIR) illumination.

In FIG. 7, the principle of total internal reflection fluorescence microscopy (TIR-FM) is shown. Light beam 610 passing through a TIR objective or a dove prism 630 illuminates the meniscus of two media, glass slide 600 and cell 620, obliquely from a high (n1) to a low (n2) refractive index with an incident angle that is greater than the critical angle of total internal reflection for these indices. An electromagnetic field called the 'evanescent field' (615) rises from the interface into the medium with a lower diffractive index. The evanescent field diminishes exponentially with distance from the interface. The decay length of the evanescent field is dependent on incident angle. In objective-type TIR-FM, a laser beam illuminates the specimen through the objective lens. As the critical angle of total internal reflection from glass (n1=1.52) to water (n2=1.33) is 61°, an objective lens that has a numerical aperture larger than 1.33 should be used for objective-type TIR-FM. Specially designed objective lenses that have an NA of 1.45 (for a use with regular 1.52 glass and oil) or 1.65 (for a use with high refractive index glass and oil) are now available. The typical decay length of an evanescent field is one hundred to several hundreds nanometers, whereas the thickness of various regions of a typical cell is between 0.1 µm in lamellipodia to ~10 µm at the nucleus. Typical distances between the ventral cell surface and the glass surface are ten to a few hundred nanometers. The circles represent fluorescent molecules that, in TIR-FM, are visible (640) and invisible (650).

Although TIR-FM provides superior contrast compared with other far-field microscopy techniques, its application is limited to the proximity of the cell surface that is, to studying parameters in two dimensions. To observe single molecules deep inside cells in three dimensions, the methods of confocal or two-photon microscopy are applicable.

Only sparsely labeled samples (<10 particles/µm$^2$) can be visualized as single molecules using TIR-FM or confocal fluorescence microscopy owing to the low spatial resolution. Additional information can be found in Sako, Y. & Uyemura, T., *Total internal reflection fluorescence microscopy for single-molecule imaging in living cells*. Cell Struct. Funct. 27, 205-213 (2002), and Funatsu, T., Harada, Y., Tokunaga, M., Saito, K. & Yanagida, T., *Imaging of single fluorescent molecules and individual ATP turnover by single myosin molecules in aqueous solution*. Nature 374, 555-559 (1995).

Two-Photon Microscopy (TPM)

Two-photon microscopy (TPM) is a form of laser-scanning microscopy that uses excitation that has about half the energy required to excite the fluorescent label. This type of excitation is termed two-photon excitation (TPE). The technique relies on the phenomenon of near simultaneous absorption of two photons by the same molecule. When this event occurs, the fluorophore is excited, and subsequently relaxes while emitting a photon with its standard emission characteristics. Obviously, for two photons to be absorbed simultaneously (within $10^{-16}$ second), the flux of photons must be very high. This special situation produces the unique characteristics of two-photon microscopy: the fact that the excitation depends on the square of the energy ensures that excitation occurs only in a very small sample volume, in the beam's focus, with practically zero background excitation; the long wavelength enables deep penetration into cells, tissues and even live organisms (Zipfel W R, Williams R M, Webb W W. *Nonlinear magic: multiphoton microscopy in the biosciences*. Nat. Biotechnol. 2003 November; 21 (11):1369-77, Heinze, K. G., Koltermann, A., and Schwille, P., *Simultaneous two-photon excitation of distinct labels for dual-color fluorescence cross-correlation analysis,* 2000, PNAS 97 (19), 10377-10382). Additionally, the unique spectral characteristics of the TPE spectra allow the simultaneous excitation of several different fluorophores with the same two-photon illumination.

Since its discovery in 1990 (Denk, W. et al., *Two-photon laser scanning fluorescence microscopy*, science 248, 73-76 (1990)), TPM has been used in a variety of applications, from measuring calcium dynamics in brain slices and live animals, to in-vivo studies of angiogenesis and metastasis, to studies of hamster embryo development.

The high intensity of photons required for TPE is basically achieved in two ways. First, a laser beam is focused through a confocal laser-scanning microscope. In the focal plane, this yields the order of $5\times10^{24}$ photons per cm$^2$ per second. This creates some TPE, but coupled with the low detection efficiency it is insufficient for imaging. The next level of intensity concentration is achieved by a mode-locked titanium sapphire (Ti:S) laser, that produces about 80 million pulses a second, each with about 100 $f_s$ duration. Thus, with the same average intensity, maximal intensity is increased drastically and the intensity of TPE is increased by about 5 orders of magnitude. In view of these properties, the focal point of a TPM image is very sharp, and the light impinging on it is well structured. The emission photons, on the other hand, are scattered, sometimes considerably. Thus, a primary consideration in detector choice is the collection angle, and direct detectors such as large area photomultiplier tubes (PMT) close to the objective lens are appropriate.

Most types of fluorophores have been used with TPM, starting from molecules that have a relatively small action cross-section such as NADH, and ending with quantum dots that allow TPM with a few microwatts of laser power.

The main advantages of TPM are due to localized excitation, expanded wavelength accessibility of most fluorophores and the complete alleviation of out-of-focus photobleaching and photodamage. In addition, the ability of TPM to simultaneously excite different types of fluorophores with the same laser is important in many applications as well as in PSM.

Since 1996, TPM instruments are available from several manufacturers: Biorad Microscience (Hemel Hampstead, UK), Zeiss (Oberkochen, Germany) and Leica (Wetzlar, Germany). Commercial Ti:S lasers for TPM are available from Spectra-Physics (Mountain View, Calif.) and Coherent (Sunnyvale, Calif.).

Additional Microscopy Techniques

In this section several additional microscopy techniques are mentioned, that are applicable in certain embodiments to the present invention.

Fluorescent lifetime imaging (FLIM) is a technique in which the fluorescent lifetime, rather than intensity, is measured. (Emptage, N J, "*Fluorescent imaging in living systems*", Curr Opin Pharmacol. 2001 October; 1 (5):521-4, Bastiaens P I, Squire A., "*Fluorescence lifetime imaging microscopy: spatial resolution of biochemical processes in the cell*", Trends Cell Biol. 1999 February; 9 (2):48-52. Review). The fluorescence lifetime is the typical time that the fluorophore remains in the excited state. These lifetimes are usually in the order of nanoseconds. Microscopes equipped with FLIM can differentiate between different fluorophores that have different average lifetimes. Commercial FLIM microscopes are available, for example, from PicoQuant GmbH (Berlin, Germany). Model "MicroTime 200" is capable of single molecule detection, and can operate also in fluorescence correlation (FCS) mode.

Second harmonic imaging microscopy (SHIM) is a microscopy technique that relies on special organic crystals (Campagnola P J, Loew L M. "*Second-harmonic imaging microscopy for visualizing biomolecular arrays in cells, tissues and organisms*", Nat. Biotechnol. 2003 November; 21 (11):1356-60. SHIM is based on a nonlinear optical effect of frequency doubling. This effect requires intense laser light to pass through a special material—usually an inorganic crystal. The light emerging from the crystal has precisely half the wavelength of the incoming light. In contrast with two-photon microscopy, no fluorescence occurs, and the coherence of the laser light is preserved.

There are a vast and growing number of additional microscopy techniques, including those using fluorescent labels, techniques with non-fluorescent labels, and non-imaging techniques such as atomic force microscopy and photon tunneling microscopy, any of which may optionally be used with the present invention.

Cameras and Detectors

According to the microscopy system used, a point detector such as PMT may optionally used, or an area detector such as a camera, for example. When PMTs are required, it is recommended to use a large-area PMT with high gain and low readout noise. Recently GaAsP photocathode PMTs are commercially available (Hamamatsu H7422P) which offer high quantum efficiency in the 400-650 nm range. This makes them well suited for TPM fluorescent work and in particular to PSM applications.

When wide-field microscopy is used, an imaging device is preferable for simultaneous observation of a relatively large area (100×100 microns) with a large number of pixels (1000× 1000 or more). It is important to use a camera which has a high signal to noise ratio simultaneously with high frame rate. In order to achieve the high signal to noise, cooled CCD cameras are used such as available from Princeton Instruments, Vianen, Netherlands. Recently, intensified CCD cameras have been introduced such as the intensified digital CCD camera system IPentaMAX-512EFT, from Roper Scientific, Trenton, N.J. Such cameras allow the detection of individual fluorophores.

Signal Generation and Analysis

Figure 8:
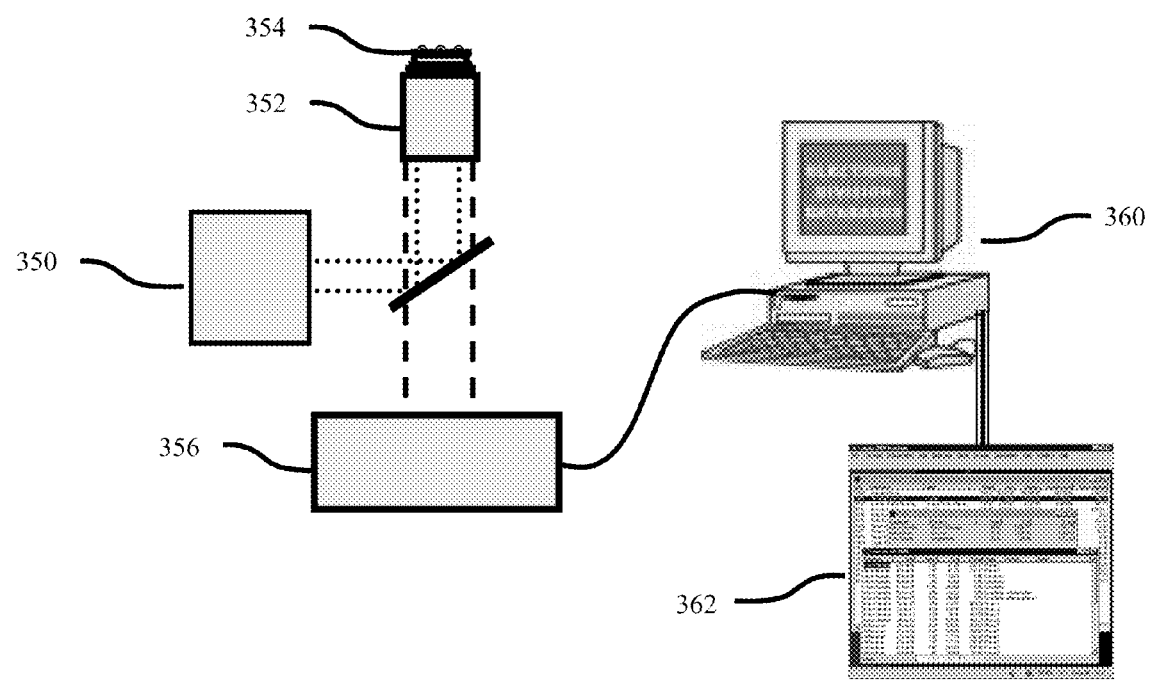
FIG. 8 describes the general setup of a PSM system.

In FIG. 8, an exemplary overview of one preferred embodiment for signal generation and analysis is presented. This example describes a general framework where each of the elements is described in more detail below. Illumination module 350 illuminates sample 354 through microscope 352, and the resulting signals are detected by detection module 356. The resultant image is then preferably transferred to computerized analysis station 360 which analyzes the images, preferably records the FRET donor and acceptor signals with their precise timing and coordinates in the image, and optionally and preferably correlates the resulting signal sequences with protein data from a database 362, to obtain protein identification data that is optionally presented on the computer screen and optionally stored in database 362 for further analysis.

Figure 9:
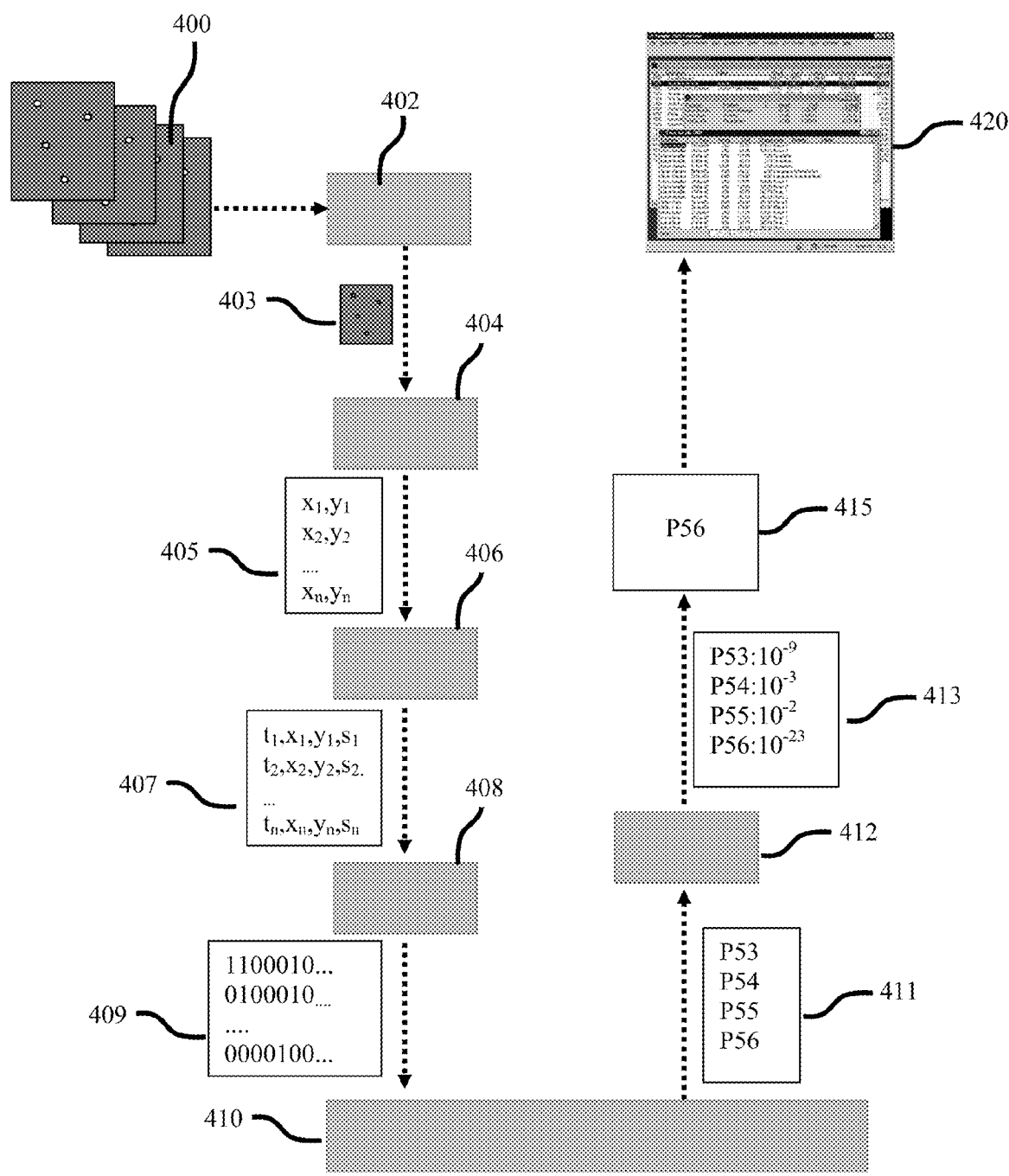
FIG. 9 describes the stages of the signal processing channel.

The optical data from detection module 356 is received by the computerized analysis station 360 as a sequence of images, preferably at a rate of 60-300 frames per second to ensure that the synthesis cycle, operating at a rate as high as 20 amino acids per second in bacteria (and at a much lower rate in eukaryotes) is properly sampled. An exemplary method that analyses this image sequence is shown with regard to FIG. 9. Image sequence 400 is first received by recording module 402. An image 403 is processed by preprocessing module 404 that identifies putative signals in the single image. These signals are output as a list of coordinates 405 to signal sequencer module 406 that tracks the signals and clusters them into a list of separated signal sequences 407. In this process random or otherwise unmatchable signals are filtered out. A signal sequence is preferably of the form $S=(t_1, x_1, y_1, s_1), (t_2, x_2, y_2, s_2), \ldots, (t_n, x_n, y_n, s_n), \ldots$. Where $t_i$ denotes a timing value, $x_i$, $y_i$ denote image coordinates, and $s_1$ denotes signal type or intensity (of both donor and acceptor). Signal sequencer module 406 updates this list of sequences S and each updated sequence is sent to sequence analyzer 408 which transforms the sequence S into one or more datastream 409 of FRET on/off signals, as further described in detail in the simulation experiment below (section entitled "data interpretation simulation").

Data stream 409 is preferably sent to protein identification module 410 that processes the data stream 409 and preferably retrieves a list 411 of protein sequences that putatively match data stream 409. A scorer module 412 preferably determines, for each candidate protein sequence from list 411, the probability that this protein is responsible for the observed signal sequence. The scored list 413 of scored protein candidates is optionally and preferably analyzed, and preferably each protein candidate 415 with a probability higher than a predetermined probability threshold is displayed on the screen. Each such protein candidate 415 is also preferably recorded in database 420. A more detailed description of data analysis is described in the data interpretation simulation detailed example below.

Multiple Ribosome Monitoring

In yet another preferred embodiment of the present invention, an optional, exemplary method is disclosed by which a plurality, tens, hundreds or even thousands of ribosomes can be monitored simultaneously. This method is important in order to ensure detection of rare or rarely synthesized proteins, such as proteins that have a very low copy number, sometimes less than one copy number per cell, on average. The size of the ribosome (along the mRNA) is approximately 20 nM. Along the mRNA strand, there are usually numerous ribosomes at various stages of translation. The distance between these ribosomes is about 40 nM. A typical mRNA may be attached to dozens of ribosomes, depending on the mRNA length. This means that it is sufficient to tag only about 10% of ribosomes. This level of tagging can be achieved by limiting the tag concentration with respect to the number of ribosomes in the assay. There are anywhere from 1000 to 20,000 ribosomes in a single cell, so that in order to identify single-copy number proteins it is required to image 10% of that number, i.e. 100-2000 ribosomes. This can be done either in one cell or in a cell culture with tens or hundreds of cells. An imaging device with pixel size of about 100 $nM^2$ and 1000×1000 pixels will have a field of view of 100 square microns, which holds 100 eukaryotic cells. Thus, monitoring 20 ribosomes per cell (as a non-limiting example) over a population of 100 cells results in 2000 ribosomes being monitored simultaneously. This enables such a system to identify single-copy proteins in real-time.

There is a tradeoff between the number of ribosomes monitored, the copy-number sensitivity, and the temporal response of the system. If only about 1% of ribosomes are monitored, then a single-copy protein is detected only once in 10 syntheses, and would be expected to require about 10 times longer to detect than when about 10% are monitored, for example.

Section II

Detailed Experimental Examples

This section provides a number of exemplary, illustrative, non-limiting examples of experiments that could optionally be performed with various preferred embodiments and optional implementations of the present invention. These examples are provided for the purpose of description only and are not intended to be limiting in any way.

E1 Labeling and Wet Setup for In-Vitro Protein Synthesis Monitoring

E1A Rhodamine-Fluorescein Labeling

General description. In this example the tRNA is the FRET donor. It is labeled with fluorescein isothiocyanate (FITC), a dye whose excitation and emission peaks are 494 and 520 nm, respectively. Ribosomal protein L1 is the acceptor and is labeled with TMR (tetra-methyl rhodamine), a dye whose and excitation and emission peaks are 550 and 573 nm, respectively. It has been shown (Plumbridge et al., NAR 8, 827-843, 1980) that tRNA labeled with this protocol retains its activity both in charging (with aminoacyl synthetases) and in the ribosomal synthesis cycle. The example shows labeling of $tRNA^{phe}$ but any tRNA with similar structure (X base) can be similarly labeled (see tRNA base modification table in the section entitled "tRNA labeling" above). The labeled tRNA and ribosomal protein are constituted into an in-vitro translation system, and used to translate an appropriate mRNA. In this system the tRNA species that is introduced is unique since after the salt-wash stage no tRNA remains. This enables verification of the system's functionality, by comparing signals in a system where all $tRNA^{phe}$ are labeled, as opposed to a similar system in which all $tRNA^{phe}$ are unlabeled. A poly-U mRNA is used as the translation template. Similar comparisons can be done with poly-U template versus other templates that do not code for phenylalanine. Obviously this illustrative system can be used in many additional forms, using additional tRNAs and various mRNAs to produce signals that can be predicted and compared with observation according to the present invention. Note: Instead of (or in addition to) labeling ribosomal protein L1, ribosomal protein S1 could also optionally be similarly labeled, and there are numerous additional labeling strategies that could optionally be adopted.

Donor labeling-$tRNA^{phe}$ labeling with FITC—Pure *E. coli* $tRNA^{phe}$ (Roche Applied Science, Mannheim, Germany) is labeled at the X base (position 47) with FITC (Sigma) (see for example Plumbridge et al., NAR 8, 827-843, 1980, and Robbins et al., Biochemistry 22, 5674-9, 1983). Approximately 1 ml of $tRNA^{phe}$ (130$A_{260}$ units) are dialyzed for 8 h against a solution of 1M NaCl and 50 mM Hepes-KOH (pH 8.0). After dialysis of the tRNA, a dimethylformamide solution containing 100 mM FITC is added to give a final dye concentration of 10 mM. The reaction mixture is incubated for 5 h at 37° C. and then brought to 100 mM KCl, and the tRNA is precipitated by addition of 2 volumes of ethanol and incubation for 2 h at −20° C. The labeled tRNA is further separated from unreacted dye by two additional ethanol precipitations.

Unlabeled tRNA is removed by passing the tRNA over a BD-cellulose (Serva) column equilibrated with a solution containing 400 mM NaCl, 50 mM NaOAc (pH 5.0), and 10 mM Mg(OAc)$_2$. The labeled tRNA is loaded in a minimal volume of the same solution. Then, a salt gradient of 0.4-2M NaCl is applied to the column. The unlabeled tRNA is eluted first, followed by elution of the $tRNA^{phe-X-F}$. The labeled tRNA is concentrated by ethanol precipitation in the presence of 2% NaOAc and subsequently dialyzed versus buffer containing 10 mM PIPES, 10 mM Mg(OAc)$_2$, 100 mM NH$_4$Cl, 150 mMKCl and 1 mM DTE. The tRNA that is used in all experiments is nearly 100% labeled. Where necessary, this is accomplished by isolation of the specific labeled tRNA species using HPLC, as described in [Odom et al., Methods Enzymol. 164, 174-187, 1988].

Acceptor labeling-ribosomal protein labeling with Tetramethyl rhodamine (TMR): cf protocol of supplier, molecular probes FluoReporter... Tetramethylrhodamine Protein Labeling Kit (F-6163).

Aminoacylation of labeled tRNAphe—Cell-free translation systems may include only the ribosomal machinery and whatever tRNAs are chosen to be introduced, or else they may include the entire enzymatic set including the 20 aminoacyl synthetases and the amino acids required for recharging the tRNAs. An example for the latter type of system is described in Shimizu et al., Nature Biotech. 19, 751-5, 2001. When the synthetases are not present, as described in this illustrative example, it is necessary to separately charge the labeled tRNA with the appropriate amino acid in order for the tRNA to function during protein synthesis. Note that in this illustrative example tRNA species that are present in the system are only those which are expressly introduced. Charging the labeled tRNA with phenylalanine proceeds according to the following protocol (Plumbridge et al., NAR 8, 827-843, 1980, Johnson et al., J. Mol. Biol. 156, 113-40, 1982) (additional, different protocols can also be found in Robbins et at Biochemistry 20, 5301-9, 1981, and in Janiak F et al, Biochem 29, 4268-77 1990.) The reaction mixture contains 20 μM phenylalanin, 2 mM ATP, 300 μg of 5100 enzymes (purified as described in Johnson et al., J. Mol. Biol. 156, 113-40, 1982) and approximately 0.2 μM tRNA in final volume of 5 ml buffer containing 100 mM Tris-HCl (pH 7.5), 10 mM Mg(OAc)$_2$, 20 mM KCl and 1 mM DTE. Following incubation of 30 min at 37° C., the Phe-$tRNA^{phe}$ is two times phenol extracted and two times ethanol precipitated. The Phe-$tRNA^{phe}$ is further purified by chromatography on a Sephadex G25 column (Pharmacia) at 4° C. in 1 mM potassium acetate (pH 5.0), and then reprecipitated. After resuspension in 1 mM potassium acetate (pH 5.0), the tRNA is dialyzed versus the same buffer before storage at −70° C.

Plasmid construction and overexpression of ribosomal proteins Ribosomal proteins L1 or S1 are amplified by PCR from *E. Coli* genome and cloned into vector pET21a (Novagen) to generate His-tagged protein plasmids (see for example Shimizu et al., Nature Biotech. 19, 751-5, 2001). The plasmids obtained are transformed into *E. coli* BL21/DE3 strains. His-tagged proteins are purified as follows: BL21 cells are grown to an OD$_{600}$ of 0.5-0.9 in Luria-Bertani (LB) broth. Isopropyl-β-D-thiogalactoside (IPTG) is added to a final concentration of 0.1 mM, and the cells are grown for an additional 4 h at 37° C. Collected cells are resuspended in a buffer [50 mM HEPES-KOH pH 7.6, 1M NH$_4$Cl, 10 mM MgCl$_2$, 0.3 mg/ml lysozyme, 0.1% Triton X-100, 0.2 mM phenylmethylsulfonyl fluoride (PMSF), and 7 mM β-mercaptoethanol] and are lysed by sonication. Cell debris is removed by centrifugation at 100,000 g for 1 h at 4° C., and the supernatant is applied to a Ni$^{2+}$ precharged Hi-trap chelating column (Amersham-Pharmacia-Biotech). The column is then washed with 10 volumes HT buffer [50 mM HEPES-KOH pH 7.6, 1M NH$_4$Cl, 10 mM MgCl$_2$, and 7 mM β-mercaptoethanol (βME)] containing 10 mM imidazole.

Proteins are eluted with a linear gradient from 10 mM to 400 mM imidazole in HT buffer. Fraction containing His-tagged proteins are dialyzed against stock buffer [50 mM HEPES-KOH pH 7.6, 100 mM KCl, 10 mM MgCl$_2$, 30% glycerol and 7 mM βME] and are frozen in small aliquots at −80° C. A general reference for purification of His-tag proteins can be found in Terpe K., Appl Microbiol Biotechnol. 2003 January; 60 (5):523-33.

Preparation of ribosomes and ribosomal 50S and 30S subunits (Bakin et al., J. Mol. Biol. 221, 441-453 1991)—Frozen *E. Coli* cells (150 g) are resuspended in 150 ml of buffer containing 20 mM Tris-HCl pH 7.2, 20 mM MgCl$_2$, 200 mM NH$_4$Cl, 2 mM βME, at 4° C. The cells are then broken by 3 passes through a French press at 1260 kg/cm$^2$. 401 μl of DNase I are added and the tube is centrifuged twice for 20 min at 18,000 revs/min. The supernatant is centrifuged for 3 h at 30,000 revs/min. The pellet of 70S ribosomes is resuspended in buffer A containing 20 mM Tris-HCl pH 7.2, 10 mM MgCl$_2$, 500 mM NH$_4$Cl, 2 mM βME, and centrifuged through 30% (w/v) sucrose for 15 h at 38,000 revs/min. The 70S pellet is resuspended in buffer A and centrifuged for 15 min at 18,000 revs/min. The supernatant is dialyzed against 100 volumes of buffer containing 20 mM Tris-HCl pH 7.2, 1 mM MgCl$_2$, 200 mM NH$_4$Cl, 2 mM βME, and centrifuged through a 10% to 30% (w/v) sucrose gradient for 16 h at 22,000 revs/min. Fraction corresponding to the 30S subunit peak are pooled and the MgCl$_2$ concentration is increased to 20 mM and then the 30S subunits are precipitated with 0.67 volume ethanol. The 50S subunits are precipitated with 100 mg/ml polyethylenglycol (M$_r$ 6000). The pellets of subunits are resuspended in buffer containing 20 mM Tris-HCl pH 7.2, 20 mM MgCl$_2$, 200 mM NH$_4$Cl, 2 mM βME, and dialyzed against the same buffer for 3 h at 4° C. Subunits are stored in −70° C.

Preparation of ribosomes and ribosomal 50S subunits lacking protein L1 from E. Coli—preparation of 50S subunits lacking protein L1 (50S-L1) from E. coli mutant strain, which does not contain ribosomal protein L1, is performed as described in Odom et al., Biochemistry 29, 10734-44, 1990, Odom et at Biochemistry 19 5947-54, 1980.

Incorporation of labeled L1 into 50S ribosomal subunit Labeled L1 is incorporated into 50S in a reaction mixture containing 400 pmol of 50S-L1, 440 pmol of labeled L1, 10 mM Tris-HCl pH 7.5, 8 mM Mg(OAc)$_2$, 150 mM NH$_4$Cl, and 5 mM βME, in final volume of 100 µl. Incubation is for 10 min at 35° C. Subunits isolated by centrifugation at 49,000 rpm for 4 h (see for example Odom et al., Biochemistry 29, 10734-44, 1990).

Poly(U)-dependent polyphenylalanine synthesis by TMR-labeled ribosomes and FITC-labeled Phe-tRNA$^{phe}$ In total volume of 100 µl: 25 mM Tris-HCl pH 7.5, 12-14 mM MgCl2, 25 mM NH4Cl, 100 mM KCl, 3 mM dithioerythritol, 4 mM βME, 0.8 mM ATP, 0.05 mM GTP, 5 mM phosphocreatine, 2.5 µg of creatine phosphokinase, 4 µg labeled phe-tRNA$^{phe}$, 20 µg poly(U), ~60 µg of E. coli postribosomal supernatant (prepared as described in Odom et al. Arch Biochem Biophys 230, 178-193, 1984), 5×10$^{-5}$M Phe (5 Ci/mol), and 30S and 50S ribosomal subunits, generally 0.8 A$_{260}$ units of 50S with optimal amount of 30S, usually 0.45-0.5 A$_{260}$ units. The reaction mixture is incubated for 30 min at 37° C. (see for example Odom et al Biochemistry 19 5947-54, 1980; alternative protocols can be found in Plumbridge et al., NAR 8, 827-843, 1980, and Shimizu et al., Nature Biotech. 19, 751-5, 2001).

E1B Quantum Dot-Rhodamine Labeling

General description. In this example Ribosomal protein L1 is the FRET donor. It is labeled with a quantum dot whose emission peaks at 525 nm. tRNA is the acceptor and it is labeled with TMR (tetra-methyl rhodamine), a dye whose excitation peaks at 550 nm and emission at 573 nm. tRNA could also be labeled with FITC as in the previous example, and a quantum dot with appropriate emission characteristics selected. tRNA labeled with this protocol retains its activity both in the aminoacyl synthetases and in the ribosomal synthesis cycle. The example shows labeling of tRNA$^{phe}$ but any tRNA with 4-thiouridine in position 8 can optionally be similarly labeled. There are about 20 such tRNAs in E. Coli, see complete list in the section entitled "tRNA labeling" above. The labeled tRNA and ribosomal protein are constituted into an in-vitro translation system, and used to translate an appropriate mRNA. Once the setup is ready, system testing can proceed as explained in the previous example. Note: Instead of labeling L1, ribosomal protein S1 could also be similarly labeled. Ribosomal protein S1 contains two cysteines, and therefore could be labeled with an appropriate protocol. For example, coumarin could be used as donor for a TMR acceptor. The labeling protocols are described in Odom et al. Arch Biochem Biophys 230, 178-193, 1984, or Bakin et al., J. Mol. Biol. 221, 441-453 1991.

Donor labeling—ribosomal protein L1 labeling with quantum dots (QD) L1 protein is first biotinylated using FluoReporter Biotin-XX protein labeling kit (Molecular Probes, cat# F-2610) according to manufacturer protocol. Then, the biotinylated protein is linked to Qdot™ 525 Streptavidin Conjugate (QuantumDot) according to manufacturer protocol.

Acceptor labeling—tRNA$^{phe}$ with TMR [cf. Yiwei et al., PNAS 94, 7932-7936, 1997, Johnson et al., J. Mol. Biol. 156, 113-40, 1982]—Pure E. coli tRNA$^{phe}$ (Roche Applied Science, Mannheim, Germany) is labeled at the 4-thiouridine (position 8) with tetramethylrhodamine-5-iodoacetamide—TMR (Molecular probes) 30 A$_{260}$ units of E. Coli tRNA$^{phe}$ are dissolved in 0.7 ml of 48 mM potassium phosphate pH 8.4 and mixed with 2.8 ml of MeSO containing 3.1 mg of TMR. After stirring in the dark for 7 h, the tRNA$^{phe}$ is removed by ethanol precipitation. The non-covalently bound dye is removed by two phenol extractions: the first is performed at pH 4.6 and a second after heat denaturation of tRNA$^{Phe}$-TMR in 10 mM Tris-HCl pH 7.0, 1 mM EDTA at 85° C. for 2 min. The labeled tRNA is then extracted with ether. After ethanol precipitation the labeled tRNA is dialyzed against 1 mM potassium acetate pH 5.0. The final tRNAPhe-TMR adducts are reactivated at 37° C. for 10 min prior to the experiment. In order to increase the activity of the TMR labeled tRNA$^{phe}$, it is sometimes recommended to attach the TMR label via a long tether. This attachment is made using bifunctional crosslinkers (Pierce Biotechnology, Rockford, Ill.).

All other processes described herein, including aminoacylation of labeled tRNAphe; plasmid construction and overexpression of ribosomal proteins; preparation of ribosomes and ribosomal 50S and 30S subunits; preparation of ribosomes and ribosomal 50S subunits lacking protein L1 from E. coli; incorporation of labeled L1 into 50S ribosomal subunit; and poly(U)-dependent polyphenylalanine synthesis by TMR-labeled ribosomes and FITC-labeled Phe-tRNA$^{phe}$; may optionally be performed as described in the previous illustrative example.

E2 Microscopy Setup

E2A Bulk In-Vitro Microscopy Setup

Bulk In-Vitro Monitoring of Protein Synthesis, Confocal Microscopy, and PMT Detector for Detecting PSM Signals.

Figure 10:
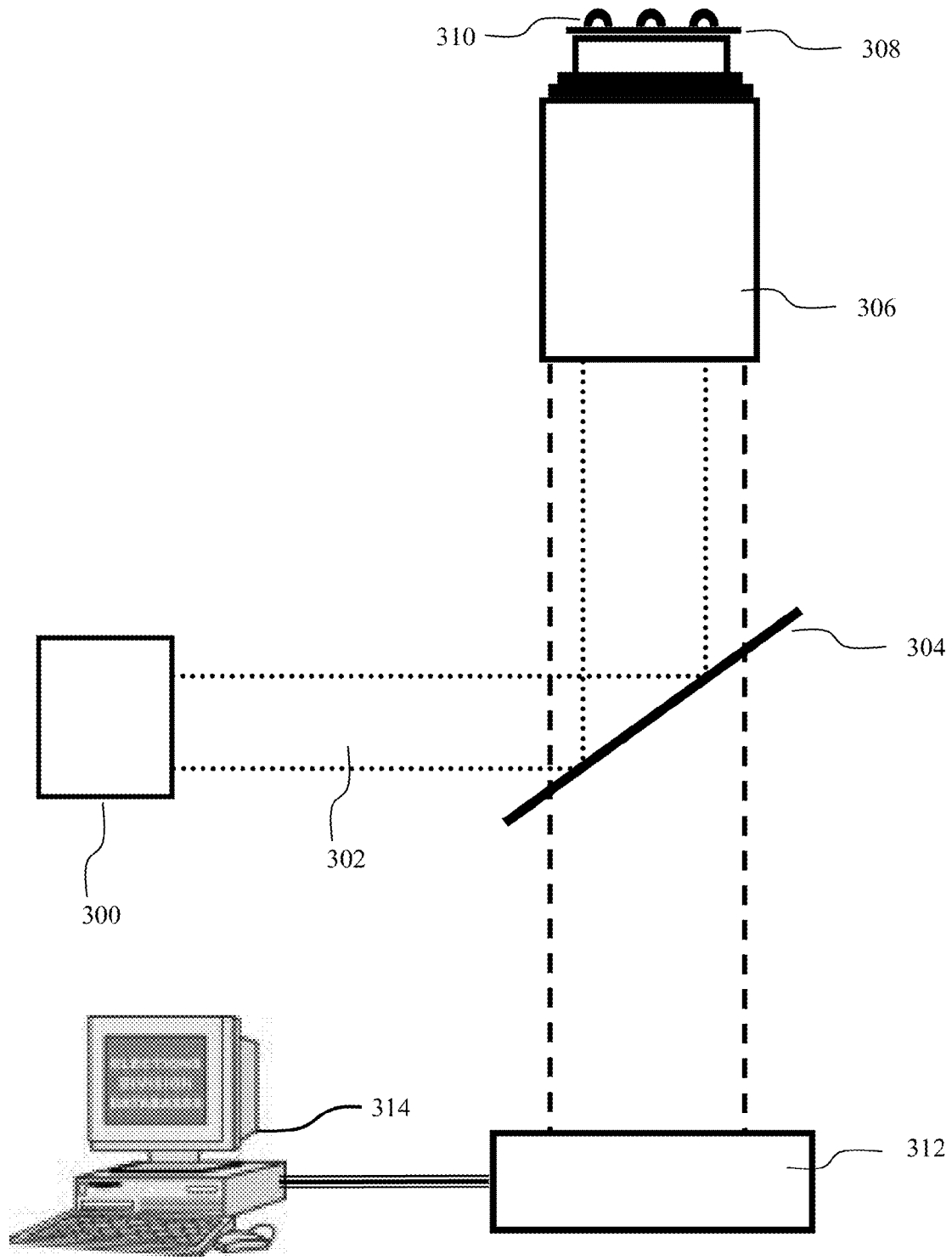
FIG. 10 describes a confocal microscopy setup for PSM.

FIG. 10 shows an illustrative apparatus for bulk in-vitro protein synthesis monitoring, where PSM signals are generated in solution. Scanning laser 300 with appropriate wavelength and energy impinges a light beam 302 optionally through dichroic mirror 304, preferably into an inverted upright confocal microscope 306, optionally and preferably focusing on a movable fused silica slide 308 on which sample wells 310 are located. The laser energy excites the donor fluorophores, which transfer energy without photon transfer to the acceptor fluorophores according to the scheme used. FRET energy transfer occurs when an acceptor tag is in sufficient proximity to a donor tag. When this FRET excitation occurs, the fluorescence signal emitted from the acceptor passes back through microscope 306 and dichroic mirror 304, to be collected by detector 312. An example of an available commercial system that embodies this type of optical design is the Olympus FluoView 500 confocal microscope available from Olympus America Inc., Melville, N.Y. The system enables a choice of laser illumination (Blue Argon (488 nm), Multi-line Argon (457 nm, 488 nm, 514 nm), Green Helium Neon (543 nm), Red Helium Neon (633 nm), Yellow Krypton (568 nm), 442 nm Helium Cadmium, 440 nm Diode, 405 nm Diode UV Argon (351 nm), 750 nm IR), a choice of PMTs with an option for several PMTs used in parallel, and several scanning modes (XY, XYZ, XYT etc). The PMT readout is transferred digitally to computer system 314 for image analysis, signal processing and subsequent identification of the proteins being synthesized.

Figure 11:
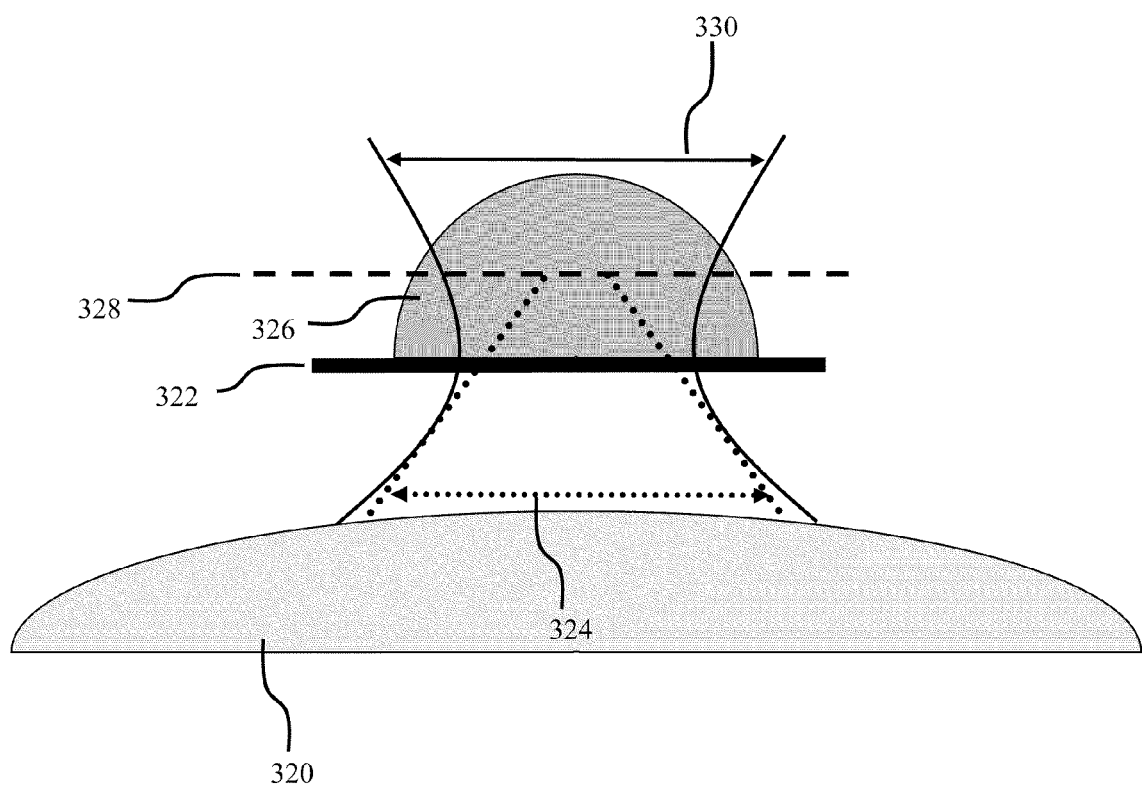
FIG. 11 describes confocal PSM optical setup at the sample scale.

FIG. 11 shows a close-up of the exemplary system shown in FIG. 10, at the sample level. Laser illumination passes through objective lens 320, which typically has a high numerical aperture such as NA=1.4 or more. The illuminated volume has the shape of a pinched cylinder, depicted by hyperbolic section 330. Movable microscope slide 322 supports well 326 in which the sample is enclosed. An imaged pixel lies in the image plane 328, bringing to a minimum the volume of illuminated sample, and thereby bringing to a minimum the number of ribosomes imaged at any one time. The FRET signals (both donor and acceptor) to be detected return along the same optical path between lines 324 and into objective lens 320, as described above.

E2B Single-Molecule In-Vitro Microscopy Setup

Single-Molecule In-Vitro Monitoring of Protein Synthesis, Immobilized Ribosomes, Wide-Field Microscopy, TIR Illumination, and ICCD Image Acquisition for Detecting PSM Signals.

Figure 12:
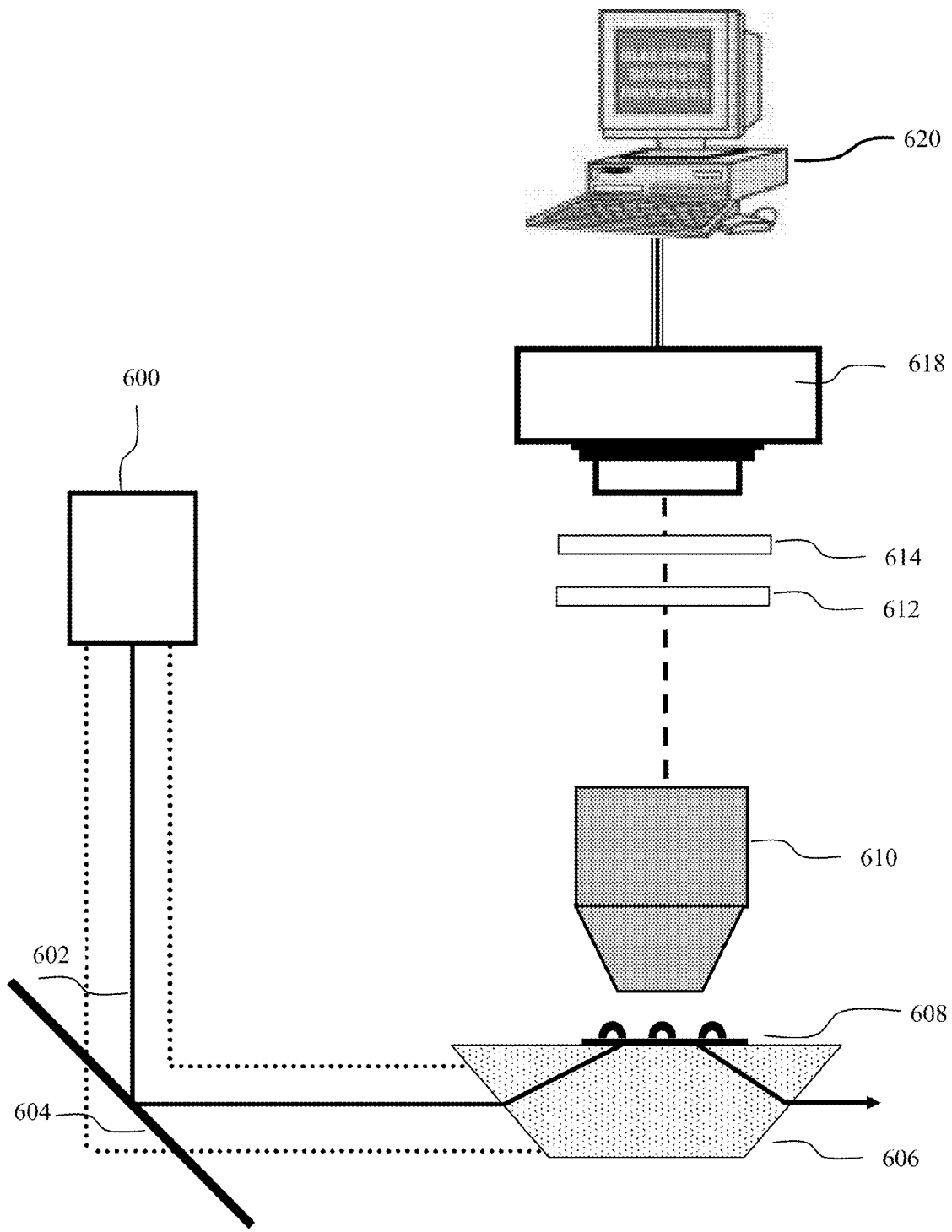
FIG. 12 describes a wide-field TIR microscopy setup for PSM.

FIG. 12 describes one optional but preferred embodiment for an exemplary optical apparatus for data acquisition, based on a wide-field microscope equipped with TIR illumination and intensified CCD camera. This setup is useful both for in-vitro single-molecule protein synthesis monitoring application, where the ribosomes are immobilized on the microscope slide, and for in-vivo PSM, where the ribosomes are monitored inside living bacteria or cells. Referring to FIG. 12, laser 600 is a diode-pumped doubled YAG laser (Crystalaser, Reno, Nev.) that can excite a wide range of dyes. Laser illumination 602 travels through a dichroic mirror 604 (Chroma Technology, Brattleboro, Vt.) and into a dove prism 606 such as a small Pellin Broca prism (CVI laser, http://www.cvilaser.com/) where the illumination undergoes TIR. The prism is optically coupled to the fused silica bottom of the sample chamber 608, so that evanescent waves illuminate up to 150 nm above the surface of the fused silica. The emitted fluorescence signals (both donor and acceptor fluorescence signals) pass through objective 610 (Olympus, DPLanApo 100UV 1.3oil, or PLAPO60XO, Plan APO 60× oil immersion, NA=1.4 working distance=0.15 mm), through a fluorescent filter 612 (Chroma Technology, Brattleboro, Vt.) and imaging lens 614 into intensified ccd (ICCD) camera 618 such as Cascade:512B available from Roper Scientific Photometrics, a camera that has on-chip multiplication gain and a back-illuminated CCD with dual amplifiers. In this type of camera, the impact-ionization process generates low-noise as multiplication of photon-generated charge takes place on the CCD, which undergoes deep thermoelectric cooling. This camera can be operated at 10 MHz for high-speed image visualization or more slowly for high-precision photometry. Supravideo frame rates are achievable through subregion readout. The camera readout is transferred digitally to computer system 620 for image analysis, signal processing and subsequent identification of the proteins being synthesized.

For in-vitro single molecule PSM, the synthesizing system must be immobilized on the microscope slide. There are two basic options for immobilization. One is to immobilize the ribosomes. Ribosomal complexes can be immobilized onto a mica surface, which is transparent and flat on a molecular size scale. Ribosomes, either labeled or unlabeled, undergo binding to mica in a few seconds, allowing the detection of single fluorescence images in aqueous buffer. A large excess of ribosomes and a short incubation period are employed for single molecule detection. The mica-bound ribosomes retain their activities, as shown in Sytnik et al., J. Mol. Biol. (1999), 285, 49-54, where detailed protocols are provided.

Another option is to immobilize the mRNA and allow the ribosomes to process the immobilized mRNA. The mRNA can be immobilized on a polyethylene glycol (PEG) coated surface with biotin-streptavidin linker. The mRNA should undergo 3'-end biotin labeling. Since protein synthesis will not end normally because of the linked 3' end, it is advisable to ensure that the template mRNA continues for at least 90 nucleotides beyond the stop codon.

E2C Single-Molecule In-Vivo Microscopy Setup

Single-Molecule In-Vivo Monitoring of Protein Synthesis, Live Cells, Confocal Scanning Optical Microscope (CSOM), Two-Photon Fluorescence Illumination, and GaAsP Photocathode PMT Detector for PSM Signals.

Figure 13:
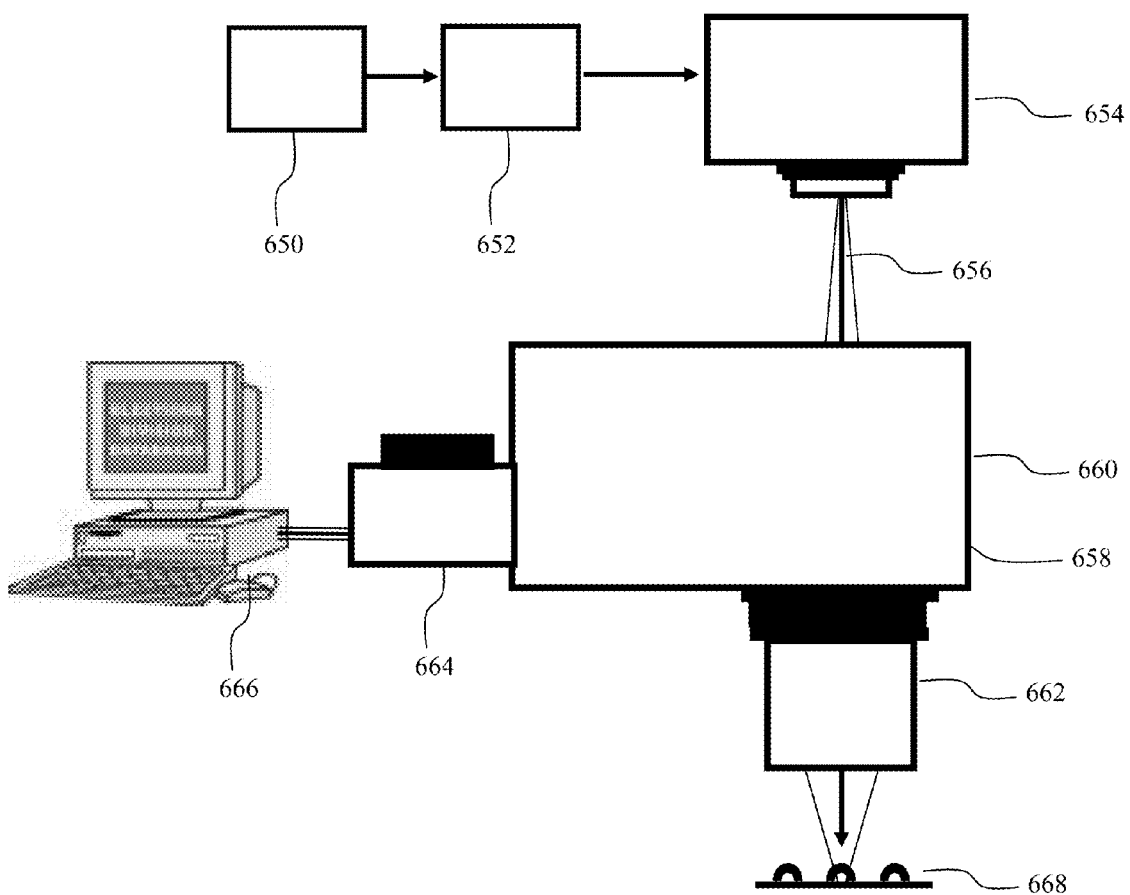
FIG. 13 describes a two-photon microscopy setup for PSM.

FIG. 13 describes one optional but preferred embodiment for an exemplary optical apparatus for data acquisition, based on a scanning two-photon microscopy system. This setup is useful for monitoring protein synthesis in single ribosomes in-vivo, in prokaryotic bacteria or cells of higher organisms. It is also optionally useful for in-vitro PSM assays according to the present invention. Referring to FIG. 13, laser 650 is a Nd:YVO$_4$ pump laser producing 10 W power that drives the mode-locked Ti:S pulsed laser 652. The Ti:S laser provides up to 1 W at the peak wavelengths of the laser. The pulsed beam from Ti:S laser 652 enters a beam scanner 654 that allows control of the beam intensity, as well as adjusting the size of the beam at the back aperture of the objective, thereby controlling the parameters of two-photon excitation spot geometry. The beam scanner, or beam-conditioning unit, provides the control of beam alignment, intensity and size and its main purpose is to optimize the filling of the objective lens by the scan beam. The main role of the beam scanner is to scan the beam over the image area and thereby produce the sampled image. The conditioned, scanned beam 656 now travels to microscope 660, through dichroic mirror 658 into objective 662 and focused onto the live cell sample in sample holder 668. The fluorescent signals are collected again by the objective, passed through the mirror and detected by PMT detector 664. The detected digital data is transferred digitally to computer system 666 for image analysis, signal processing and subsequent identification of the proteins being synthesized. An example of an available commercial system that embodies this type of optical design is the Radiance 2100™ MP multiphoton microscopy system available from Bio-Rad Laboratories, cell science division, Hercules, Calif. In this instrument, scanning speeds of 25 to 1800 Lines Per Second (LPS) and frame rates of 45 frames/sec can be obtained, with a wide choice of lasers, basic microscopes, and detectors, including true photon counting of up to 20M photons per second. Various scanning modes (XY, XYZ, XYT etc.) are also available.

E3 Monitoring of Protein Synthesis In-Vivo

E3A General Description of In-Vivo PSM.

This illustrative example describes the use of CHO cells but any other cell line or bacterial cell culture would do equally.

For in-vivo monitoring of protein synthesis, fluorescent tagging according to R-T, R-A or R-R strategies is performed. In this illustrative set of examples R-T tagging strategy is used and disclosed in detail. For R-T tagging to succeed in-vivo, ribosome tagging and tRNA tagging have to be properly handled. There are two preferred choices for tRNA labeling as FRET acceptor: FITC (excitation and emission peaks are 494 and 520 nm, respectively) and TMR (excitation and emission peaks at 550 and 573 nm, respectively). TMR is attached to the thiouridine at position 8, while FITC is attached to the X-base at position 47, as explained in detail previously. The ribosome is labeled as FRET donor on ribosomal protein L1 in this illustrative example. The particular choice of labeling fluorophore for L1 depends on the acceptor fluorophore chosen. Four exemplar illustrated donor/acceptor choices are shown in the following table:

TABLE 3

| L1 Donor fluorophore | tRNA acceptor fluorophore |
|---|---|
| L1-GFP fusion protein | TMR |
| L1-BFP fusion protein | FITC |
| L1-CCPGCC-FlAsH | TMR |
| L1-BCCP-Qdot ™ 525 | TMR |

It is important to ensure that when a certain tRNA species is labeled, practically all tRNAs of this species in an assayed cell are labeled. Each of the two methods below achieves this with a different approach. The first uses a unique (suppressor) tRNA for which there is no endogenous competition from unlabeled tRNA. In the second approach the production of unlabeled tRNA in the cell is actively down-regulated.

For ribosome tagging, optional but preferred fluorescent labeling of ribosomal protein L1 as FRET donor is described in detail. Three alternative methods for in-vivo tagging of L1 are described. All three require fusing L1 to an additional peptide or protein. This fusion is preferably performed by insertion of a vector encoding the fusion protein into the cells.

In a first exemplary method L1 is fused to a naturally fluorescent protein such as GFP or BFP, as described in Chalfie, M. & Kain, S. (1998), Preface in: *Green fluorescent protein: properties, applications, and protocols*, eds. Chalfie, M. & Kain, S. (Wiley-Liss, New York), pp. vii-ix, incorporated herein in its entirety.

In a second exemplary method L1 is fused to a short peptide of 6-20 amino acids containing a CCXXCC motif (for example CCPGCC). This motif binds specifically to a bi-arsenoxide group. Then FlAsH, a dye derivative of fluorescein, is added to the cells (Miyawaki et al., Nat Cell Biol. 2003 September; Suppl:S1-7, and references therein). The FlAsH label is membrane-permeant and non-fluorescent, and acquires fluorescence only on binding to the CCXXCC motif.

In a third exemplary method L1 is fused to a sequence tag derived from biotin carboxyl carrier protein (BCCP), thereby becoming biotinylated in-vivo (Nilsson et al., "*Affinity Fusion Strategies for Detection, Purification, and Immobilization of Recombinant Proteins*", Protein expression and purification 11, 1-16 (1997)). This allows streptavidin conjugated quantum dots to be attached to the biotinylated protein. Practically, Qdot™525 Streptavidin Conjugate (Quantum Dot Corporation, Hayward, Ca) is added to the cells according to manufacturer protocol. In-vivo labeling with Qdots are described in Jaiswal J K, Mattoussi H, Mauro J M, Simon S M, Nat. Biotechnol. 2003 January; 21 (1):47-51.

Because of resolution limits of microscopy systems, optionally and preferably only a relatively small percentage of ribosomes should be labeled. One exemplary method that achieves this goal requires placing the fusion L1 protein under the regulation of a very weak promoter, to ensure low expression levels. For the other two labeling methods, other than GFP-L1 or BFP-L1 fusion, careful control of the externally introduced dye (FlAsH or Qdots) amounts is an alternative, optional and simpler mechanism.

tRNAs are preferably labeled in-vitro and then delivered into the cells. tRNAs can be inserted into cells by one of at least the following three procedures: 1. by injection, as described in Ilegems, E., et al., Nucleic Acids Res. 2002 Dec. 1; 30 (23); 2. by using TransMessenger transfection reagent (Qiagen, Hilden, Germany) according to the manufacturer protocol. 3. by using TransIT-TKO transfection reagent (Mirus Corporation, Madison, Wis.) according to the manufacturer protocol.

It is well known that *C. elegans* can simply absorb RNAi from solution. This ability may imply that tRNA molecules can also be simply absorbed by cells, a strategy which is preferably tested individually in each cell-line and labeling strategy.

E3B In-Vivo Monitoring of Protein Synthesis Using Suppressor tRNA and Unnatural Amino Acids General description. In order to verify the proper functioning of the PSM assay according to the present invention, suppressor tRNA may optionally be used to ensure that native tRNA does not compete with labeled tRNA during the PSM assay. The suppressor tRNA is preferably the only tRNA species to be labeled, and therefore the only one to generate a PSM FRET signal. The suppressor tRNA introduced into the cells recognizes a codon that is usually recognized by the cell as a stop codon. The amber (UAG) codon is usually employed for this aim. The suppressor tRNA is preferably not a substrate for any of the cellular aminoacyl—tRNA synthetases.

This suppressor tRNA molecule is preferably subsequently aminoacylated with a highly fluorescent unnatural amino such as 7-azatryptophan, and a special template mRNA is introduced that is engineered to contain amber codons in prespecified locations. One optional choice for the template tRNA is based on bacteriophage T4 lyzosyme protein (T4L), as explained in Cornish et al., "*Site specific incorporation of biophysical probes into proteins*", Proc. Natl. Acad. Sci. USA, Bol. 91 2910-2914, 19. This fluorescent amino acid is preferably incorporated in a fluorescent protein wherever an amber codon was processed with the suppressor tRNA. Note that in this configuration the charged suppressor tRNA is doubly labeled, once as a FRET acceptor and once with the fluorescent amino acid it is charged with. In particular, the engineered T4L protein will be indicative of the functioning both of the suppressor tRNA and of the PSM assay. In this way it is possible to obtain independent verification of the results of the PSM assay. Additionally, the accuracy of the PSM method can optionally be correlated with detection of the fluorescent translation products. Important parameters such as quantitation accuracy of the PSM assay can be measured.

The suppressor tRNA is preferably constructed on the basis of the *E. coli* tRNA$^{Phe}$, *E. coli* tRNA$^{Asn}$, or *E. coli* tRNA$^{Asp}$, as described in the references below. All of these tRNAs have a 4-thiouridine in position 8 and so can be labeled with TMR, *E. Coli* tRNA$^{Phe}$ also has an X-base in position 47 and can therefore be labeled with FITC. Detailed labeling protocols were described previously in the section entitled "Labeling and wet setup for in-vitro protein synthesis monitoring".

Preparation of suppressor tRNA—details. A variety of suppressor tRNAs have been misacylated and tested for their ability to incorporate amino acids into proteins in response to an amber nonsense mutation. Chamberlain and coworkers focused their efforts on *E. coli* tRNA$^{Gly}$ (Bain et al., Biochemistry 1991, 30, 5411-5421). Schultz and coworkers determined that suppressor tRNA$^{Asn}$ from *E. coli* and tRNA$^{Gln}$ from *T. thermophila* showed the best overall suppression efficiency for amino acid incorporation into model proteins T4 lysozyme and chlorismate mutase (Cload et al, Chem. & Biol. 1996, 3, 1033-1038).

In view of the strategies described above, *E. coli* amber (UAG) suppressor is optionally and preferably prepared from *E. coli* tRNA$^{Phe}$ or tRNA$^{Asn}$ according to the protocols in the references above. The tRNA amber suppressor has a CUA anticodon sequence. Other tRNAs can also serve as a basis for engineering a suppressor tRNA for the amber codon for PSM, as long as they contain a 4-thiouridine in position 8 or an X-base in position 47, to allow labeling. Other tRNAs that do not have these modifications may also optionally be used but an appropriate labeling strategy compliant with amino-acylation and translation should be devised.

The stages of the experiment optionally and preferably include: Creation of the suppressor tRNAs; Fluorescent labeling of the suppressor tRNAs; Charging the suppressor tRNAs with 7-azatryptophan. (cf. Cornish et al., Proc. Natl. Acad. Sci. USA, Bol. 91 2910-2914, 19); Insertion of a vector that codes both for the L1 fusion protein (one of 3 choices) and the template mRNA encoding for the reporter protein (such as the amber-labeled bacteriophage T4L); Once the transfected vector undergoes transcription, the labeled, charged suppressor tRNAs and any additional dyes (FlAsH or Qdots) are inserted.

E3C In-Vivo Monitoring of Native Protein Synthesis

General description. In this non-limiting, illustrative example natural protein synthesis by ribosomes is monitored in-vivo. Labeling of a single tRNA species (tRNA$^{Phe}$) is described but multiple labeling is also possible.

Since the cell manufactures its own, unlabeled tRNA, its production is optionally and preferably stopped before the labeled tRNA is introduced. This stoppage ensures that nearly all tRNAs of the required species are indeed labeled. Thus endogenous unlabeled tRNAs that are part of the live cell are optionally and preferably replaced preferably fully by labeled tRNAs. Since endogenous tRNAs are necessary for cell viability, the tRNA species to be labeled is placed under induction control, so that their production can be stopped when the labeled tRNAs are introduced. The turnover rate of tRNAs, whether endogenous or externally introduced, is in the order of 1-2 days (Schlegel et al., "*The turnover of tRNAs microinjected into animal cells*", Nucleic Acids Research, Vol 5, Issue 10 3715-3729), so that the production of the endogenous tRNAs that have been placed under control needs to be stopped a sufficient amount of time before labeled tRNAs are introduced and the PSM assay starts operating.

Preparation of Cell Line

CHO-ind-tRNA$^{phe}$ cell-line is optionally and preferably established from CHO cells in which the endogenous gene coding for tRNA$^{Phe}$ is placed under the control of inducible POL III promoter. Such promoters are described in Wolfgang M. et al., (2001) NAR 29, 1672-1682; Tuschl T. (2002) Nature Biotechnol. 20, 446-448; Van de Wetering, M., et al, (2003) EMBO Rep 4, 609-15; Hurlstone, A., et al., (2002) EMBO L. 21, 2303-11. The replacement of the natural control elements of the required tRNA genes by inducible control is performed by gene targeting techniques as described in (Joyner, A L (ed), "*Gene Targeting: A Practical Approach*", Oxford University Press; 2nd edition, 2000).

The stages of the experiment optionally and preferably include: Establishing the cell-line CHO-ind-tRNA$^{phe}$; Fluorescent labeling of the *E. Coli* tRNA$^{Phe}$ molecules; Insertion of a vector that contains the L1 fusion protein (optionally according to one of three previously described choices); Down regulation of the POL III promoter driving the unlabeled tRNA$^{phe}$ transcription; and Introduction of L1 dyes (if required) and labeled tRNA$^{Phe}$.

E4 Data Interpretation Simulation

This Example describes a simulation of an illustrative method for signal processing according to the present invention. A specific, illustrative algorithm of data analysis that permits real-time identification of the protein being synthesized from raw FRET signals is described. The data processing proceeds by stages according to the following diagram (FIG. 14-A). The raw, or double signal 510 is the signal obtained simultaneously from donor and from acceptor of a single FRET pair, as is customary for FRET analysis. A typical graph of the double signal is shown in FIG. 14-B, with acceptor signal 520 and donor signal 521. These graphs were created by a simulation program written in C++ under Microsoft visual studio development suite. The model assumes that signals are generated with parameters as indicated below. Random number generation was used to create noise according to the prescribed parameters. Donor signal is shown in thin black line, acceptor signal in thick grey line. The simulated signal generation model assumes a sampling rate of 200 samples per second, a synthesis rate of 20 amino acids per second, average "off" signal of 1.2/0.1 relative brightness values for donor/acceptor, respectively, and an average "on" signal of 0.2/0.9 for donor/acceptor, respectively. The "on" and "off" values are assumed to have been previously calibrated by experimental measurements. Additional assumptions that underlie the simulation experiment model are the following: the FRET signal is "on" for 50% of the synthesis cycle time of a single amino acid, on average, with an average deviation of 10% from this value; the synthesis cycle time changes on average by 8% from the average cycle time; the signal noise level is 18% of maximal signal; and labeling efficiency is 95% (that is, at most 1:20 tRNAs that should have been labeled turn out to be unlabeled).

Once the simulated PSM signal is generated, the analysis process can begin its operation. As shown in FIG. 14A, the first stage in the analysis produces the FRET signal 511 from the double signal 510. This is a binary signal at the original sampling rate. A sample graph of this signal is shown in graph 530 (FIG. 14-C). Only the "on" periods are shown. In this example the computation of the FRET signal involves a simple subtraction of acceptor signal minus donor signal. If this is positive, an "on" FRET bit is output, else, an "off" bit. Note that the signals are calibrated for their "on" and "off" values. If the calibration values are different than the values shown in FIG. 14B, other decision schemes such as a weighted difference of the signals (a*acceptor-b*donor, with a and b some fixed positive weights) may optionally be required.

The next stage produces the synthesis signal 512, which provides a time reading for each "on" period. It is assumed that when a FRET signal is emitted, it takes place only during part of the synthesis cycle. Thus, it is easy to separate adjacent FRET periods. On the other hand, when the peptide sequence includes a several adjacent non-labeled sequence elements, separation of the units is not straightforward and has to be computed. The synthesis signal records the time points of the center of each FRET period. To compute this synthesis signal 512, the beginning and end points of each FRET period are recorded first. In the simulation experiment the initial three periods occurred at times 0.088-0.1126, 0.0233-0.0258, 0.284-0.308. The midpoints of these intervals, 0.1003, 0.245, 0.296 are the values that form the synthesis signal. All time values are given in seconds.

The next stage produces the label sequence tree 513. Suppose two consecutive "on" signals were recorded at times $t_1$ and $t_2$. The average synthesis time is known to be Ts and the standard deviation of synthesis cycles has been measured to be σ, in seconds, or $σ_c=σ/Ts$, in cycles, or intervals. The number Noff of "off" cycles between $t_1$ and $t_2$ can be computed with an uncertainty that can be evaluated as follows. The average time required for N synthesis cycles is $T_N=N·Ts$. The standard deviation of the accumulated time required for N cycles is therefore $\sqrt{N}·σ_c$, in interval units. The standard deviation $\sigma_{Nc}$ for N cycles in cycle units is therefore $\sigma N_c = \sqrt{N} \cdot \sigma_c$. The distribution of the total duration of N cycles can be assumed normal with standard deviation $\sigma_{Nc}$. The conditional probability that a sequence of N synthesis cycles will deviate by at least $\Delta I$ intervals from the expected interval duration is therefore $P(N, \Delta I) = P(x > \sigma_{Nc})$ and can easily be computed or found from normal distribution tables.

For example, for the time difference $0.245 - 0.1003 = 0.1447$ seconds between first and second "on" periods in the simulation experiment, given an average synthesis cycle time of $\frac{1}{20} = 0.05$ seconds and standard deviation of 0.27 intervals, the expected number of cycles is $0.1447/0.05 = 2.894$. Examination of the probabilities that 2, 3 or 4 cycles would require 0.1447 seconds yields the following values:

$P(2, 0.1447)$: $\sigma_{Nc} = 0.27 \cdot \sqrt{2} = 0.38$, $\Delta I = 0.1447/0.05 - 2 = 2.894 - 2 = 0.894$, $N(0.38, 0.894) = 0.019$ $P(3, 0.1447)$: $\sigma_{Nc} = 0.27 \cdot \sqrt{3} = 0.47$, $\Delta I = 0.1447/0.05 - 3 = 2.894 - 3 = -0.106$, $N(0.47, -0.106) = 0.973$ $P(4, 0.1447)$: $\sigma_{Nc} = 0.27 \cdot \sqrt{4} = 0.54$, $\Delta I = 0.1447/0.05 - 4 = 2.894 - 4 = -1.106$, $N(0.54, -1.106) = 0.04$ Intervals that are shorter than 2 or longer than 4 are discarded since the probability for their occurrence is negligible. In order to compute the probability of each of these intervals occurring, given the conditional probabilities above, the total probabilities are normalized as follows: $P_{Total} = 0.019 + 0.973 + 0.04 = 1.036$, and the final normalized probabilities are $P(2) = 0.019/1.036 = 0.018$ $P(3) = 0.973/1.036 = 0.939$ $P(4) = 0.04/1.036 = 0.043$, with all other probabilities set to zero.

In this way, given the synthesis signal 512, every additional "on" signal generates one or more labeled sequences. In the previous example, the label sequences that were generated, with their probabilities, are FN (0.018), FFN (0.939), FFFN (0.043), where "F" stands for "off" and "N" stands for "on". When the different labeled sequences are joined together, a data structure in the form a branched tree with probabilities attached to the nodes is obtained. Every newly computed labeled sequence is attached as a suffix to each one of the preceding sequences. The probability of the final branch is the product of the probabilities of the prefix and the newly added suffix. A branch whose probability falls below a prescribed value, such as 0.001, is discarded. This avoids exponential increase in the number of branches. In the simulation experiment, starting from the simulated labeled peptide FNFFNN-FFFNNNFFFFNNNN, the tree in FIG. 14-D is obtained.

Reading each branch from top to bottom and enumerating the resulting sequences 1-7 from left to right, the following sequences are obtained, as shown in Table 4 below:

TABLE 4

| ID | Sequence | Probability |
| --- | --- | --- |
| 1 | FNFNNFFFNNNFFFFNNNN | 0.011858 |
| 2 | FNFFNNFFNNNFFFFNNNN | 0.02108 |
| 3 | FNFFNNFFFNNNFFFNNNN | 0.050066 |
| 4 | FNFFNNFFFNNNFFFFNNNN | 0.814229 |
| 5 | FNFFNNFFFNNNFFFFFNNNN | 0.035573 |
| 6 | FNFFNNFFFFNNNFFFFNNNN | 0.047431 |
| 7 | FNFFFNNFFFNNNFFFFNNNN | 0.019763 |

Note that the sequence with highest probability (sequence 4) is identical to the original input sequence. As the process continues, branches can split and re-split; some branches are deleted since their probability falls below the acceptable threshold; and in this way the measured label sequence tree evolves. At every stage, each candidate sequence is sent for database interrogation and scoring (see below). Branches that do not appear in the database are deleted or otherwise marked for special consideration.

The final stage in the protein identification module is the database interrogation stage. For this, the database has to be compiled. Every protein sequence is simply transformed to a label sequence by marking each amino acid as "N" of "F" according to whether its synthesis will result in a FRET signal or not. Next, all subsequences of a given length (say, 100 cycles) that start with an "N" are determined. For an organism such as $E.$ $coli$ that contains under 5000 ORFs with average length of under 1000 bps yields proteins with 300 amino acid on average, so that the database for $E.$ $Coli$ will include less than $5000 \times (300 - 100) = 1$ million entries. This entire set of sequences is now built into a tree data structure (cf. Donald E. Knuth, The Art of Computer Programming, Addison-Wesley). In this tree, the sequences start from the top (null) node, and split according to the number of "F" cycles between every neighboring "N" cycles. In every node, the total number of (different) proteins covered by the branches stemming out of the node is noted. Once this number becomes lower than a prescribed number (for example 5), the set of proteins is retrieved for display or storage, together with the probabilities as discussed above. This can be done in real-time, resulting in a dynamic display of proteins as they are being synthesized.

The database can also take into account labeling efficiency. For example, if a given amino acid residue is considered to be labeled with an efficiency of, say, 90%, than every sequence where this residue appears is used to derive mis-labeled sequences at a rate of 10%. All these mislabeled sequences are stored in the database as well. This may mean that longer sequences are required to positively identify a protein.

It is possible to further analyze the relationship between the number of labeled versus non-labeled units. The R-A labeling scheme is herein analyzed as an example. The other two schemes, R-T and R-R labeling can easily be analyzed in a similar way. Suppose that k of the 20 amino acids are labeled and 20-k are unlabeled. Assume that a subsequence of total length l (both labeled and unlabeled) has been read. Assume uniform distribution of amino acids. In this case, $\alpha = k/20$ of the l residues can be expected to be labeled, so that there would be $p = \alpha l$ labeled residues and $l - p$ unlabeled residues. The number of possible sequences would then be $$N = \binom{l}{p} = \binom{l}{\alpha l}.$$

This number is maximal when k=10 (or $\alpha = \frac{1}{2}$). A realistic assumption is that for confident identification of a protein the random hit probability should be better than $1:10^6$, or, in other words, $$\binom{l}{\alpha l} > 10^6.$$

This is because there are at most several hundred thousand sequences in the database (see above). Thus, for confident protein identification, the formula $$\binom{l}{\alpha l} > 10^6$$

connects the ratio α of labeled amino acids with the length l of a polypeptide chain required for confident identification. The following table provides example values:

TABLE 5

| Number of labeled amino acids | Minimal number of residues (l) required for confident identification | Total synthesis time in bacteria (seconds) for confident identification |
|---|---|---|
| 1 | 80 | 4.0 |
| 3 | 42 | 2.0 |
| 5 | 28 | 1.4 |
| 6 | 26 | 1.3 |
| 10 | 23 | 1.06 |

Thus it is beneficial to partition the amino acids as equally as possible. It is also clear that protein identification can be obtained in under 2 seconds in bacteria (where synthesis rate is approximately 20 residues a second). Protein synthesis in eukaryotes is about an order of magnitude slower.

If codons rather than amino acids are labeled, than with the simplistic assumption of uniform codon distribution, the connection between number of labeled codons and identification is given in the table below.

TABLE 6

| Number of labeled codons | Minimal number of residues (l) required for confident identification | Total synthesis time in bacteria (seconds) for confident identification |
|---|---|---|
| 1 | 200 | 10.0 |
| 3 | 90 | 4.5 |
| 5 | 65 | 3.25 |
| 6 | 60 | 3.0 |
| 10 | 40 | 2.0 |

If probes with several different colors are used, rather than a single-colored probe, more information becomes available for identification of the synthesized protein. For example, assume that 10 amino acids are labeled with a single color probe, and the remaining 10 are unlabeled. For a peptide with N amino acids, there are $$\binom{N}{10} = N!/10! \cdot (N-10)!$$

possible PSM signal sequences out of the total of $20^l$ amino acid sequences. However, if the 10 labeled amino acids are labeled with 2 types of fluorescent probes, say 5 of each, than in this case the number of possible PSM signal sequences becomes $$\binom{N}{5}\binom{N-5}{5} = \frac{N!}{5! \cdot (N-5)!} \cdot \frac{(N-5)!}{5! \cdot (N-10)!} = \frac{N!}{5! \cdot 5! \cdot (N-10)!}.$$

The ratio of information content is therefore $$\left(\frac{10!}{5! \cdot 5!}\right) = 252$$

fold. This means that multi-labeling can require considerably less time to identify the protein being synthesized, with a higher confidence.

E4A Identification Strategies Using Key Computation from a Sequence of Data Packets (SDP)

An additional strategy for using a sequence of FRET signals for identifying a protein synthesized by a single ribosome, is based on compilation of a key from a sequence of data packets (SDP). The examples described in Sections E4A (i)-(iii) employ a currently preferred embodiment of this strategy, in which a ribosome is labeled with a donor fluorophore, and one or more tRNAs are labeled with one or more distinct acceptor fluorophores. However, it is to be understood that the SDP strategy may be used with other labeling modes, for example, in which a ribosome labeled with an acceptor fluorophore and one or more tRNA or amino acids labeled with donor fluorophore(s).

The analysis starts with detection and measurement of the sequence of FRET signals emitted from the protein translation system. The measurement of the FRET signal may include in some applications its timing as well as additional parameters such as for example signal duration, and amplitudes of donor and/or acceptor and/or FRET signals.

If more than a single label type is used for labeling the tRNAs, then the measurement of the FRET signal can include the type of label. For example, if the donor on the ribosome is Cy3 and the acceptors on the tRNAs are Cy5 and Cy5.5 then acceptor and FRET signals for the Cy5 labels would preferably be measured through one optical channel of the optical instrument, while FRET signals for the Cy5.5 labels would be measured through a second optical channel of the optical instrument, facilitating identification of the type of label currently on the ribosome. The output of the measurement system in such a case would include a determination of the type of label used, yielding a sequence of label types $(T_1, T_2, \ldots T_n)$ where each $T_i$ indicates the label type.

The process of protein identification by a computerized algorithm includes three steps that are shared by embodiments of the identification strategy. First, for each individual FRET signal, the entire data measured from that signal is extracted by the image analysis software and recorded as a packet of digital data. The data can include one or more of timing, amplitude and duration for each of the (two or more) optical channels employed. Then, consecutive packets of data detected at the same location (such as a pixel) are collected to form a sequence of data packets (SDP). Finally, the SDP is sent to the identification module to identify which protein or family of proteins could have yielded the specific SDP measured. This identification phase can be invoked when no more packets are added to the SDP, or when the SDP is sufficiently long, or every time a new packet is added, or any other suitable strategy, as evident to anyone skilled in the art of sequence analysis in bioinformatics.

For the identification stage, an identification algorithm implemented on a digital computer is used, in conjunction with a database previously compiled from protein sequences, and optionally, additional data. In all embodiments, the identification algorithm uses the SDP as a key.

With this key the algorithm interrogates the database to identify which protein(s) could have yielded the measured SDP. The database includes protein-specific data for the specific set of proteins expected to be expressed during the specific experiment. This "expected experimental proteome" can include the entire proteome of an organism; the proteome of a specific tissue or organ (e.g. fibroblasts, kidney, neurons); the proteome of a sub-cellular organelle (e.g. mitochondrion, chloroplast, endoplasmic reticulum, neuronal synapse), or any other set of proteins that is relevant to a specifically designed experiment.

The identification step can be performed using several alternative identification strategies. Disclosed herein are non-limiting examples, and additional strategies can be adapted using methods known to one of skill in the art of bioinformatics.

The description herein incorporates by reference the book "Biological Sequence Analysis: Probabilistic Models of Proteins and Nucleic Acids", by R Durbin, S Eddy, A Krogh and G. Mitchison, Cambridge University Press, 1998, (hereinafter referred to as "Durbin et al., 1998").

The following examples describe the identification strategy with respect to the contents of the database, and the nature of the identification algorithm, and for the purpose of illustration, relate to the specific protein proinsulin (NCBI Reference Sequence: NP_000198.1), having the amino acid sequence:

```
                                       (SEQ ID NO: 1)
MALWMRLLPL LALLALWGPD PAAAFVNQHL CGSHLVEALY

LVCGERGFFY TPKTRREAED LQVGQVELGG GPGAGSLQPL

ALEGSLQKRG IVEQCCTSIC SLYQLENYCN.
```

The following discussion includes use of the terms defined below.

The term "labeling sequence" as used herein refers to a sequence of numerical identifiers, based on both (i) the amino acid sequence of a protein, or its corresponding mRNA sequence, or a tRNA sequence as defined below, and (ii) a labeling strategy in which one or more amino acids or tRNAs are modified by attachment of one or more label(s). To produce the labeling sequence, numerical identifiers assigned to each type of labeled amino acid or tRNA ("sequence element") are sequentially arranged according to the sequence element expected to be processed by a ribosome in accordance with the amino acid sequence of the protein. Therefore, in the exemplary case of proinsulin, if amino acids A, L and P are labeled with Cy5 (assigned as the identifier 1) and W, C and T are labeled with Cy5.5 (assigned as the identifier 2), and unmodified residues are assigned as the identifier 0, then the labeling sequence of proinsulin will be: 0112001111 1111112010 1111000001 2000100110 1020000000 2102000100 1000000100 0101001011 1100010000 0000222002 0100100020.

The database can either contain the full labeling sequence or the labeling sequence which contains only the non-zero identifiers. If the zero identifier is deleted, than the labeling sequence of proinsulin as stored in the database will be: 1121111 11111121 11111 2111 12 2121 11 11111 111 2222 112.

The term "timing sequence" as used herein refers to the sequence of expected time differences between signals emitted from differently spaced fluorophores as a polypeptide chain is synthesized by the ribosome.

For example, a timing sequence for proinsulin where the fluorophore labeling is as above contains 47 labels and therefore 46 timing gaps, resulting in a timing sequence $t_1, t_2, t_3, \ldots, t_{46}$ of 46 timings.

The term "timing sequence with variance" as used herein refers to a timing sequence as above, with its variance, based either on a measurement or a model-based prediction. The variance of the timing allows computation of the likelihood that a measured timing was produced by a normal distribution $N(\mu, \sigma^2)$ defined by the timing value $\mu = t_i$ and the variance value $\sigma^2 = v_i$ that are stored in a database. Thus, a timing sequence with variance of proinsulin will consist of a sequence $t_1 \pm \delta t_1, t_2 \pm \delta t_2, t_3 \pm \delta t_3, \ldots, t_{46} \pm \delta t_{46}$ of durations and of timing variances.

The term "tRNA sequence" as used herein refers to the sequence of tRNA molecules that is expected to be used during processing of a particular mRNA by a ribosome during the synthesis of a particular protein. In humans, 49 specific tRNA molecules exist (including that carrying selenocysteine), wherein 1 to 5 different tRNA molecules may be charged with a specific amino acid. The combination of a particular amino acid, and the specific tRNA molecule which is charged with that amino acid is denoted herein as $X_i$, wherein X is the single letter identification of the amino acid and i identifies the specific tRNA for that amino acid, wherein $1 \leq i \leq 5$.

Identifiers for tRNAs (excluding that carrying selenocysteine) may be assigned according to those shown in Table 7.

TABLE 7

| # | tRNA id | anticodon | codon1 | codon2 (wobble) |
|---|---|---|---|---|
| 1. | $A_1$ | AGC | GCT | GCC |
| 2. | $A_2$ | CGC | GCG | |
| 3. | $A_3$ | TGC | GCA | |
| 4. | $G_1$ | GCC | GGC | GGT |
| 5. | $G_2$ | CCC | GGG | |
| 6. | $G_3$ | TCC | GGA | |
| 7. | $P_1$ | AGG | CCT | CCC |
| 8. | $P_2$ | CGG | CCG | |
| 9. | $P_3$ | TGG | CCA | |
| 10. | $T_1$ | AGT | ACT | ACC |
| 11. | $T_2$ | CGT | ACG | |
| 12. | $T_3$ | TGT | ACA | |
| 13. | $V_1$ | AAC | GTT | GTC |
| 14. | $V_2$ | CAC | GTG | |
| 15. | $V_3$ | TAC | GTA | |
| 16. | $S_1$ | AGA | TCT | TCC |
| 17. | $S_2$ | CGA | TCG | |
| 18. | $S_3$ | TGA | TCA | |
| 19. | $S_4$ | GCT | AGC | AGT |
| 20. | $R_1$ | ACG | CGT | CGC |
| 21. | $R_2$ | CCG | CGG | |
| 22. | $R_3$ | TCG | CGA | |
| 23. | $R_4$ | CCT | AGG | |
| 24. | $R_5$ | TCT | AGA | |
| 25. | $L_1$ | AAG | CTT | CTC |
| 26. | $L_2$ | CAG | CTG | |
| 27. | $L_3$ | TAG | CTA | |
| 28. | $L_4$ | CAA | TTG | |
| 29. | $L_5$ | TAA | TTA | |
| 30. | $F_1$ | GAA | TTC | TTT |
| 31. | $N_1$ | ATT | AAT | |

TABLE 7-continued

| # | tRNA id | anticodon | codon1 | codon2 (wobble) |
|---|---------|-----------|--------|-----------------|
| 32. | $N_2$ | GTT | AAT | AAC |
| 33. | $K_1$ | CTT | AAG | |
| 34. | $K_2$ | TTT | AAA | |
| 35. | $D_1$ | GTC | GAC | GAT |
| 36. | $E_1$ | CTC | GAG | |
| 37. | $E_2$ | TTC | GAA | |
| 38. | $H_1$ | GTG | CAC | CAT |
| 39. | $Q_1$ | CTG | CAG | |
| 40. | $Q_2$ | TTG | CAA | |
| 41. | $I_1$ | AAT | ATT | |
| 42. | $I_2$ | GAT | ATC | |
| 43. | $I_3$ | TAT | ATA | |
| 44. | $M_1$ | CAT | ATG | |
| 45. | $Y_1$ | ATA | TAT | |
| 46. | $Y_2$ | GTA | TAC | TAT |
| 47. | $C_1$ | GCA | TGC | TGT |
| 48. | $W_1$ | CCA | TGG | |

Using the tRNA identifiers shown in Table 7, the tRNA sequence of pro-insulin is given by $M_1A_1L_2W_1M_1R_1L_1L_2P_1L_2$ $L_2A_2L_2L_2A_1L_1W_1G_3P_1D_1$ $P_3A_1A_3A_1F_1V_2N_2Q_2H_1L_2$ $C_1G_1S_3H_1L_2V_2E_2A_1L_1Y_2$ $L_3V_2C_1G_2E_2R_3G_1F_1F_1Y_2$ $T_3P_1K_1T_1R_1R_2E_1A_3E_1D_1$ $L_2Q_1V_2G_2Q_1V_2E_1L_2G_1G_2$ $G_1P_1G_1A_3G_1S_4L_2Q_1P_1L_4$ $A_1L_2E_1G_2S_1L_2Q_1K_1R_1G_1$ $I_1V_2E_2Q_2C_1C_1T_1S_4I_2C_1$ $S_1L_1Y_2Q_1L_2E_1N_2Y_2C_1N_2$ The term "mRNA" refers to the sequence of mRNA nucleic acids according to which a protein is translated. The mRNA sequence of proinsulin is:

The protein database which is used for identification of the protein being synthesized may include one or more of the following types of information pertaining to the proteins stored in the database: labeling sequences, timing sequences, timing sequences, tRNA sequences, amino acid sequences and mRNA sequences.

The identification algorithm used in identifying the protein being synthesized may be based on a method of sequence alignment, such as for example, sequence alignment using dynamic programming; local sequence alignment (Smith-Waterman algorithm), local sequence alignment with complex scores; sequence alignment using Hidden Markov Models (HMMs), suboptimal alignment (see for example, Durbin et al., 1998), or other methods.

The above six examples of database construction, and five examples of identification algorithms may be used together in any combination to provide 30 examples of strategies for protein identification from the sequence of FRET signals produced by a PSM system. Additional strategies, methods, and variants can be developed, including specifically designed methods and/or adaptations of existing methods, as is clear to anyone skilled in the art of developing bioinformatic algorithms for analysis of biological sequence data.

To further elucidate the methods described above, Sections E4A (i)-(iii) provide specific strategies for construction of the database and design of protein identification algorithms.

E4A (i) Database Containing Labeling Sequence Only with Identification Using Local Sequence Alignment with Complex Scores.

In this example, the database contains labeling sequence only, and alignment is performed by local sequence alignment with complex scores. For this example, the fluorescent labeling has two distinct labels, so that the database contains for each protein entry a sequence of two symbols: 1 (first label) and 2 (second label), and the unlabeled codons were omitted. The measured sequence of data packets (SDP) constitutes a sequence of measured labels, expressed as a sequence of two symbols, 1 and 2. We denote the measured signal sequence by $G=g_1, g_2, \ldots g_k$. This sequence is the key that will be used for interrogating the database. We denote the model sequence by $M=m_1, m_2, \ldots, m_l$. Finding the optimal alignment proceeds according to the standard Smith-Waterman algorithm. For the score function, we begin by defining (SEQ ID NO: 2)

```
  1 agccctccag gacaggctgc atcagaagag gccatcaagc agatcactgt ccttctgcca
 61 tggccctgtg gatgcgcctc ctgcccctgc tggcgctgct ggccctctgg ggacctgacc
121 cagccgcagc ctttgtgaac caacacctgt gcggctcaca cctggtggaa gctctctacc
181 tagtgtgcgg ggaacgaggc ttcttctaca cacccaagac ccgccgggag gcagaggacc
241 tgcaggtggg gcaggtggag ctgggcgggg gccctggtgc aggcagcctg cagcccttgg
301 ccctggaggg gtccctgcag aagcgtggca ttgtggaaca atgctgtacc agcatctgct
361 ccctctacca gctggagaac tactgcaact agacgcagcc cgcaggcagc ccccacccg
421 ccgcctcctg caccgagaga gatggaataa agcccttgaa ccaacaaaaa aaaaaaaaaa
481 aaaaaaaaaa aaaaa
``` the local score for a matching between a signal data point and a model data point as follows $$S(g_i, m_j) = \begin{cases} a, & \text{if } g_i = m_j \\ b, & \text{otherwise} \end{cases}$$

Since we assume a low chance of misinterpreting the labels, we can set a=1 and b=−20, for example.

Next we define the update rule, using the linear scoring function (Durbin et al., 1998), where one obvious change is introduced. In classical sequence alignment the two sequences play a symmetric role. However in our case one sequence is a model sequence and the other is a measured sequence, so that in our case their roles are not symmetrical. A gap in the measured SDP means that some events were not detected. This can arise from incomplete labeling of the tRNA, competition with native (unlabeled) tRNA, or from missed detection, leading to a gap penalty of $d_{missed}$. On the other hand, a gap in the model sequence signifies a false positive, or a detected event that does not correspond to a real signal. This can arise from detection of a non-existing signal, and leads to a gap penalty of $d_{excess}$. The two values can be computed from the measured likelihood of each event. Usually the likelihood of an undetected signal is much higher than the likelihood of false detection, so that penalty in $d_{excess}$ is much higher than the penalty of $d_{missed}$. Thus our update rule is $$F(i, j) = \max \begin{cases} F(i-1, j-1) + s(g_{i-1}, m_{j-1}) \\ F(i-1, j) - d_{missed} \\ F(i, j-1) - d_{excess} \end{cases}$$

E4A (ii) Database Containing Labeling Sequence, Timing Sequences and Timing Sequences with Variances, with Identification Based on Local Sequence Alignment.

In this example, the database contains labeling sequences, timing sequences and timing sequences with variances, and alignment is performed by local sequence alignment. For this example, the fluorescent labeling has two distinct labels. Thus, each measured entry has two values, a symbol $g_i$ and timing $t_i$, $G=(g_1,t_1), (g_2,t_2), \ldots, (g_k,t_k)$. This sequence is the key that will be used for interrogating the database. Each database entry is a sequence of data sets, where each data set contains three values (m, s, v), where m is a symbol (1 or 2) indicating the label type, s is a timing value in seconds, and v is a timing variance value in sec², or $M=(m_1,s_1,v_1), (m_2,s_2,v_2), \ldots, (m_l,s_l,v_l)$.

The analysis proceeds similar to that described in E4A(i), with two modifications. First, the local score function now takes into account both data type (symbol identity) and the timing, so that $$S((g_i, t_i), (m_j, s_j, v_j)) = S_s(g_i, m_j) + S_t(t_i, s_j, v_j)$$

Where $$S_s(g_i, m_j) = \begin{cases} a, & \text{if } g_i = m_j \\ b, & \text{otherwise} \end{cases}$$

as in example A above, and $S_t(t_i,s_j,v_j)$ is the log odds ratio of timing $t_i$ being produced by a normal distribution $N(\mu, \sigma^2)$ with mean $\mu=s_j$ and variance $\sigma^2=v_j$ (cf. Durbin 1998, 2.2).

Next, because of our dependence on timing, the update function cannot be computed from just one step back but must backtrack to the last correct match in order to compute the timing correctly. Thus, $$F(i, j) = \max \begin{cases} F(i-1, j-1) + s(g_{i-1}, m_{j-1}) \\ \max F(i-k, j) - k \cdot d_{missed}, k < i \\ \max F(i, j-k) - k \cdot d_{excess}, k < j \end{cases}$$

Here, $$F(i, j-k) = S\left((g_i, t_i), \left(m_{j-k}, \sum_{n=j-k}^{j} s_n, \sum_{n=j-k}^{j} v_n\right)\right),$$

Since we are comparing the symbol $g_i$ with the symbol $m_{j-k}$, the timing $t_i$ with the total timing difference from j−k to j, and the total variance from j−k to j (as variance is additive).

E4A (iii) Database Containing tRNA Sequences with Identification Based on the Method of Hidden Markov Models (HMM).

For this example, the database contains tRNA sequences only, and alignment is performed by the method of Hidden Markov Models (HMM). The measured sequence includes both label and timing data. For this example, the fluorescent labeling has two distinct labels. Thus, each measured entry has two values, a symbol $g_i$ and timing $t_i$, $G=(g_1,t_1), (g_2,t_2), \ldots, (g_k,t_k)$. This sequence is the key that will be used for interrogating the database. Each database entry is a sequence of tRNAs, identified as a running index with values ranging from 1 to 49 (we assume the database relates to human proteins).

The analysis algorithm is based on the method of alignment using HMMs (Durbin et al., 1988, see chapter 4). In addition to the information stored in the database, the analysis algorithm uses three data tables: a table of tRNA labeling (label type 1, type 2, or unlabeled), a table of expected timing (TET) and a table of expected timing variation (TETV), containing the expected timing variation for each tRNA type. In addition, the algorithm keeps track of the timing and variation since the last match between model and measured entries.

The identification algorithm proceeds as follows. First, the algorithm computes from the database tRNA sequence and the additional data tables a label, timing and variation sequence $M=(m_1,s_1,v_1), (m_2,s_2,v_2), \ldots, (m_l,s_l,v_l)$, where each $M_i$ has the values of 1 or 2, according to the label type; each $s_i$ is computed by summing the expected timing values given in the TET over the unlabeled tRNAs lying between adjacent labels; and each $v_i$ is computed by summing, over the unlabeled tRNAs between adjacent labels, the expected variation values given in the TETV. Next, we construct the HMM based on the example provided in (Durbin 1988, sec. 4.1). We have three states: a match state, a gap state (corresponding to unlabeled tRNAs in the model sequence), and an excess state (an unexpected label was identified that does not match a model label). The scoring function is now adjusted so the score of a match between model and SDP is a sum of the log-odds of the type match between model label $L_i$ and measured label $g_j$, and the log-odds of the measured timing being obtained from the algorithm's computed timing distribution, defined by the expected timing and expected timing variation.

The score of a gap is computed from the probability of missing a label in the detection process, where the main contribution can be the imperfection of the labeling process and competition with the native cellular, unlabeled tRNA. The score of an excess label is computed from the probability of detecting a false positive.

E5 Applications of the Present Invention

E5A Applications for High Throughput Screening Assays

Figure 15:
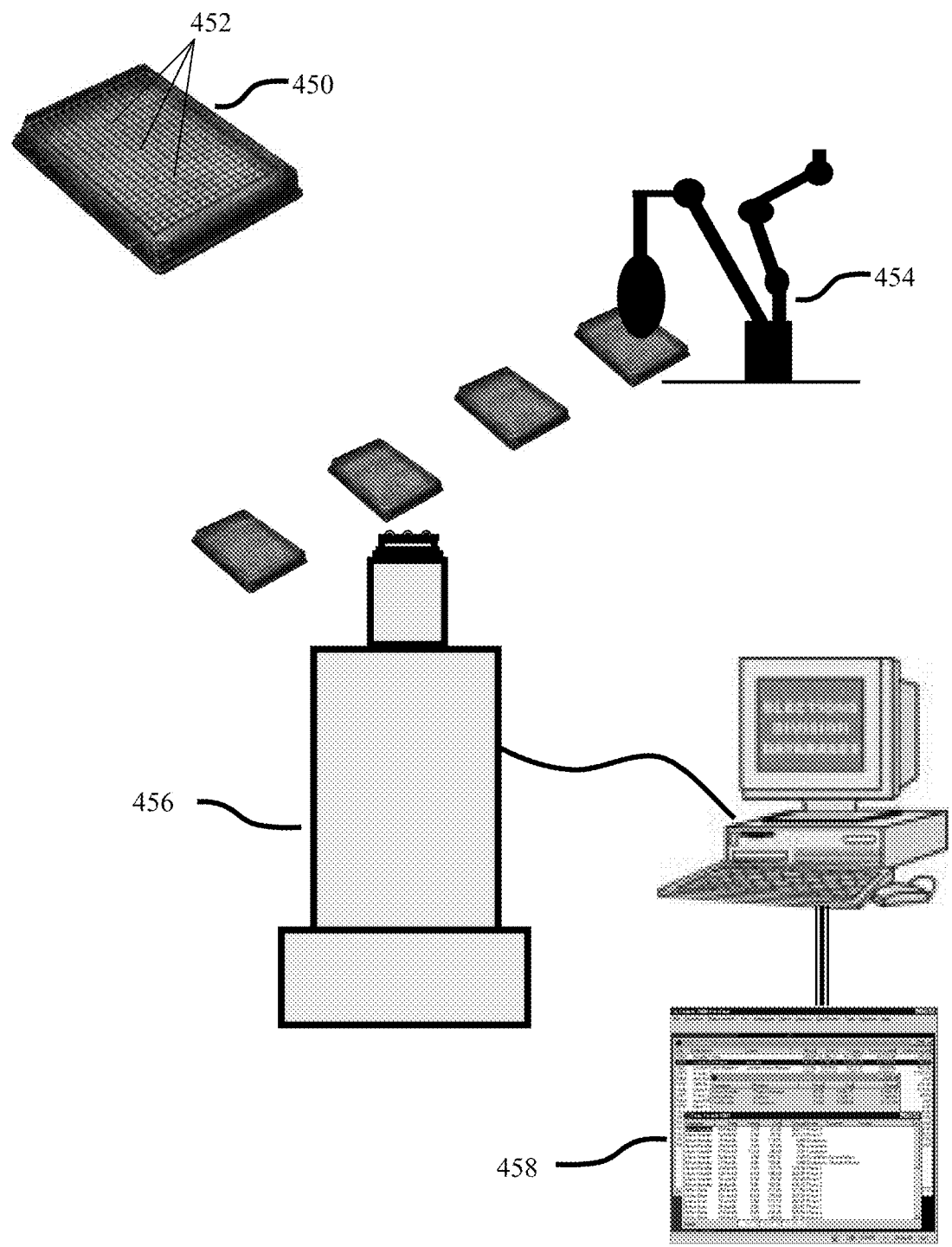
FIG. 15 shows an optional, illustrative strategy suitable for screening of a chemical compound library with the system and method disclosed herein.

This example describes how the methods disclosed herein can optionally be used for the screening of a large library of chemical compounds to determine their efficacy or their potential for use as drugs. High throughput screening is a method developed since the late 1980s. Today systems are available that can screen up to a million compounds in one day. High throughput screening requires an assay to be devised that is compatible with the screening instrument, an assay that enables quick rejection of most of the compounds as irrelevant, and approves only a small fraction for continued research. The present invention is suitable for a very thorough and informative assay, as explained above, in the sense that it provides information not only concerning binding of the screened compound to a single protein target, one that has been suspected to be related to the disease for which a drug is sought, but provides, for every compound tested, information about the full spectrum of proteins induced by the compound with their expression timing. Thus, functional activity of a compound on a specific cell type can be usefully studied by subjecting it to protein synthesis monitoring assay as disclosed herein only once for a given organism or cell-line. The optional, illustrative strategy suitable for screening of a chemical compound library with the system and method disclosed herein is depicted in FIG. 15. First, a cell line with tagged ribosomes is cultured and placed in a multiwell plate 450. This can have a 96 well plate format, a 384 well plate format or any other format compatible with automated screening. The wells 452 in the plate need to be optically amenable for microscopy as shown in FIGS. 7, 10, 11, 12 and 13. A robot 454 administers one compound out of the library being screened into each well and protein synthesis analysis is performed by a protein synthesis monitoring system 456. A suitable sampling regime should be adopted. As an illustrative example a protein synthesis monitoring measurement for 30 seconds every 10 minutes for a total of one hour. Other regimes may optionally be also used. The list of proteins synthesized by the cell together with the synthesis timing during the sampling period for the particular well are stored in screening database 458. A sampling regime as described allows screening of 20 compounds per hour per protein synthesis measurement unit. In this way, screening of a library with one million compounds can take one year with five protein synthesis monitoring units or one month with 50. Obviously many alternative regimes can also be used.

The data obtained for each compound through this PSM screening provides a list of the proteins induced by the compounds, together with the synthesis timing. Thus, the changes of the state of the cellular machine, caused by the administration of the compound, can be discerned. As an illustrative example, if the PSM assay of one compound shows a significant increase in the production of DNA repair enzymes, this may mean that the administered compound may cause DNA damage. This obviously means that the compound can never become a drug candidate. This type of information today is available only at toxicity studies stage in the drug development pipeline. Obtaining this kind of information at a very early stage of the process can save years of work and very large expenditures.

Bioinformatics analysis of the PSM data collected for each compound can further yield information concerning the main and side effects of a compound, the states of the cellular machinery that it creates, and the protein pathways that it triggers.

Though seemingly slow compared to other screening methods, the method disclosed here has numerous attractive advantages. First, the library needs to be screened only once. Thereafter, focused screening targeted at a specific receptor or disease model can be done in-silico, with the computer alone, analyzing the protein synthesis data collected. Second, only a tiny amount of compound is required since the library is screened only once. Most importantly, the data collected is orders of magnitude more informative and relevant to further research than single receptor binding assays or even cell-based assays. Thus, choice of drug leads and further development of drugs from these leads becomes much more of a research program and less of a guesswork. In this way, over a period of several months, a hitherto unobtainable amount of critical information is compiled about each of the compounds in the library. This is in contrast with the information obtained after a full run of customary screening. For example, a customary receptor-binding assay produces only one bit of information for each compound—"binds" or "doesn't bind". In fact, screening with the present invention is not so much a screening system (that rejects most of the candidates), as much as a system for assigning function for entire chemical libraries.

In this embodiment, the cells being monitored can be human cells, bacterial cultures, yeast or any other appropriate collection of cells or cell line.

E5B Applications for Drug Development and Manufacturing

Another important application of protein synthesis monitoring is as a tool for process optimization, process control and quality control of protein production, either in bio-reactors using bacteria or cell culture, or else in cell free translation systems. In these situations, the present invention can provide indispensable information about the precise amounts of the target protein being produced, as well as on the comprehensive structure of the proteome backdrop to this manufacturing, ensuring that the desired protein is produced in precisely the required environment and in the right amounts. This level of control, unavailable today, can create a revolution in the way proteins and protein drugs are produced and certified. This can lead to new protein production methods that are easier to control than current ones.

In another optional but preferred embodiment, the present invention is optionally and preferably used to monitor proteins being produced by bacteria, yeast, cell lines, cell-free translation system protein production systems or any other protein production processes. Numerous biopharmaceuticals are thus produced, including drugs and medical agents such as insulin, human growth hormone, erythropoietin, therapeutic antibodies, and other diagnostics and medical aids. The system disclosed herein can optionally be integrated into the production system, enabling production yields and rates to be measured, controlled, and optimized in real time. Moreover, PSM can help monitor precisely the cellular state and environment during the production of the target protein. This monitoring can ensure a hitherto unavailable level of control for protein production, and can also lead to new protein production methods that are easier to control than the customary methods. This new monitoring capability can make a large impact on the quality, quantity and cost of protein production, as well as allowing tighter regulatory control of protein production.

E5C Applications for Basic Biological Research

This example describes how the methods disclosed herein can be used for basic biological research. One important field of research is the understanding of protein and metabolic pathways in the cell. Numerous methods have been suggested and several technologies have been developed to try and decipher the complex net of protein interactions and pathways of bacteria and cells. These include protein-protein interaction mapping from assays, from computerized analysis of research papers, and from clever setups as described in (Shen-Orr, S. S., Milo, R., Mangan, S., and Alon, U., *Network motifs in the transcriptional regulation network of Escherichia coli.*, Nat Genet. 2002, 31 (1): 64-8). The present invention offers important advantages for pathway elucidation. Since the response of the cell to an external stimulus is instantly revealed by the monitoring of protein synthesis, the following methodology is suitable for discovering the pathways. As described in the screening application above and in FIG. 15, cells are cultured and placed in a suitable screening setup. The cells are then subjected to various external stimuli, such as temperature changes, chemical deprivation (such as phosphate starvation), administration of toxic agents, attack by phages or viruses and any other stimulus that is thought to be relevant to the pathway being investigated. The cells or bacteria are studied using the present invention for an appropriate duration before, during and after the stimulus, and the response of the protein synthesis apparatus of the cell is tabled. A computerized analysis module analyzes the different responses, including the timing order of protein synthesis, which proteins tend to co-translate, what are their amounts, and what causality relationships occur between them. By virtue of having numerous different stimuli generating numerous different responses, pathway elements can be determined as explained, for example, in Rosen et al., FEMS Microbiol. Ecol. 2001, and Hecker et al., Int. J. Med. Microbiol. 2000. The dynamic information of cellular response to external stimulus is an extremely important probe of cellular behavior, which previously could not be measured.

In another optional but preferred embodiment, protein synthesis monitoring is used to identify protein pathways and protein-protein interaction maps. In this method, different chemical and environmental conditions are applied to cells or to cell lines, and protein synthesis is monitored for each one of these conditions. The protein synthesis patterns are indicative of the cellular pathways, and the protein synthesis data for the entire experiment is used to map the cells protein interaction, thereby enabling understanding of the intricate connections and functions of proteins in the cells.

E5D Other Applications

In view of the large number of possible applications and embodiments of the present disclosure it should be recognized that the illustrated embodiments are only particular examples and should not be taken as a limitation on the scope of the disclosure. Some of the possible additional applications which are clearly enabled by the present invention are clinical applications, diagnostic applications, production of food, cosmetics, and other bioproducts, military applications concerning biological warfare, and many more.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

---

What is claimed is:

1. A method for identifying one or more proteins synthesized in a protein synthesis system, the method comprising:
binding at least one first label to at least one ribosome or a fragment thereof in the protein synthesis system;
binding at least one second label to at least one tRNA or to at least one amino acid in the protein synthesis system;
wherein the at least one first label is a donor fluorophore, and the at least one second label is an acceptor fluorophore, and wherein the donor fluorophore and the acceptor fluorophore together form a Fluorescence Resonance Energy Transfer (FRET) pair;
detecting FRET signals emitted when the at least one first label and the at least one second label are in proximity;
compiling a key from the detected FRET signals by detecting at a single location consecutive packets of data, and collecting said data as a sequence of data packets; and
interrogating with the key a protein-specific database comprising labeling sequences, by aligning the measured sequence of data packets to the labeling sequences, and identifying the database entry that best matches the measured sequence of data to thereby identify the one or more proteins being synthesized in the system.

2. The method according to claim 1, wherein the first label is a donor fluorophore and the second label is an acceptor fluorophore.

3. The method according to claim 1, wherein the method comprises binding a donor fluorophore to a ribosome, and binding an acceptor fluorophore to at least one tRNA or to at least one amino acid; or binding an acceptor fluorophore to a ribosome, and binding a donor fluorophore to at least one tRNA or to at least one amino acid.

4. The method according to claim 3, comprising
binding a donor fluorophore to a ribosomal protein selected from the group consisting of ribosomal protein L1, ribosomal protein L11, ribosomal protein S1, ribosomal protein S21, and a combination thereof; or
binding a donor fluorophore to a ribosome at a location on the ribosome at or near at least one of the A site, the P site, the E site or the peptide exit channel site.

5. The method according to claim 4, wherein the location is significantly nearer to one of the A site, the P site, the E site or the peptide exit channel site, relative to the distances between said label and each of the other three sites.

6. The method according to claim 1, wherein the density of labeled ribosomes in the system is less than about 10 labeled ribosomes per cubic micron, or is less than about 5 labeled ribosomes per cubic micron; or wherein the density of labeled ribosomes in the system is at most 0.1 labeled ribosomes per cubic micron; or wherein the density of labeled ribosomes in the system is less than about 0.1 labeled ribosomes per cubic micron, or is less than about 0.02 labeled ribosomes per cubic micron.

7. The method according to claim 1, wherein the detecting comprises: detecting FRET signals emitted from a single ribosome; or detecting FRET signals emitted from a plurality of single ribosomes; or detecting FRET signals emitted in a single-molecule microscopy system.

8. The method according to claim 7, wherein the single-molecule microscopy system comprises at least one of: a resolution limit in the range from 0.1 to 1.0 μm; an observed volume in the range from 0.2 to 1.0 μm³; a sampling rate of at least 2 frames per second; a density of labeled ribosomes no greater than 0.1 per pixel; or a density of labeled ribosomes less than 0.02 per pixel.

9. The method according to claim 7, wherein the detecting comprises measuring at least one of: sequences of emitted FRET signals; timing of emitted FRET signals; duration of emitted FRET signals; amplitude of donor fluorophore signals; amplitude of acceptor fluorophore signals; amplitude of FRET signals, or a combination thereof.

10. The method according to claim 1, wherein the single location is a single pixel.

11. The method according to claim 1, wherein the protein-specific database further comprises at least one of: timing sequences; timing sequences with variances; tRNA sequences; protein amino acid sequences, or protein amino acid subsequences; and mRNA sequences.

12. The method according to claim 1, wherein the protein-specific database comprises data based on a proteome of at least one of: an organism; a cell type, a tissue, an organ; a sub-cellular organelle, a metabolic state, a disease state, or a stage of development.

13. The method according to claim 1, wherein the interrogating a protein-specific database comprises aligning the measured sequence of data packets (SDP) to the database sequences, and identifying the database entry that best matches the SDP.

14. The method according to claim 13, wherein the aligning comprises an alignment method selected from the group consisting of sequence alignment using dynamic programming; local sequence alignment; local sequence alignment with complex scores; sequence alignment using Hidden Markov Models; and suboptimal alignment.

15. The method according to claim 14, wherein the protein-specific database comprises labeling information, and the aligning is performed by local sequence alignment with complex scores; or wherein the protein-specific database comprises data based on all of labeling sequences, timing sequences, and timing sequences with variance, and the aligning is performed by local sequence alignment; or wherein the protein-specific database comprises data based on tRNA sequences, and the aligning is performed by sequence alignment using Hidden Markov Models.

16. The method according to claim 2, comprising binding a first label to a ribosome or a fragment thereof, and binding at least two different second labels to at least two different tRNAs.

\* \* \* \* \*

SEQUENCE LISTING

```
<160> NUMBER OF SEQ ID NOS: 2

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110
```

-continued

```
<210> SEQ ID NO 2
<211> LENGTH: 495
<212> TYPE: DNA
<213> ORGANISM: Homo sapiens

<400> SEQUENCE: 2
agccctccag gacaggctgc atcagaagag gccatcaagc agatcactgt ccttctgcca      60
tggccctgtg gatgcgcctc ctgcccctgc tggcgctgct ggccctctgg ggacctgacc     120
cagccgcagc ctttgtgaac caacacctgt gcggctcaca cctggtggaa gctctctacc     180
tagtgtgcgg ggaacgaggc ttcttctaca cacccaagac ccgccgggag gcagaggacc     240
tgcaggtggg gcaggtggag ctgggcgggg gccctggtgc aggcagcctg cagcccttgg     300
ccctggaggg gtccctgcag aagcgtggca ttgtggaaca atgctgtacc agcatctgct     360
ccctctacca gctggagaac tactgcaact agacgcagcc cgcaggcagc cccccacccg     420
ccgcctcctg caccgagaga gatggaataa agcccttgaa ccaacaaaaa aaaaaaaaaa     480
aaaaaaaaaa aaaaa                                                      495
```